US012797387B2

(12) United States Patent
Moline et al.

(10) Patent No.: US 12,797,387 B2
(45) Date of Patent: Nov. 17, 2026

(54) LEMBOREXANT FOR TREATING SLEEP ISSUES

(71) Applicant: EISAI R&D MANAGEMENT CO., LTD., Tokyo (JP)

(72) Inventors: Margaret Moline, White Plains, NY (US); Lynn Kramer, Woodcliff Lake, NJ (US); Shobha Dhadda, Woodcliff Lake, NJ (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 1133 days.

(21) Appl. No.: 17/597,074

(22) PCT Filed: Jun. 25, 2020

(86) PCT No.: PCT/US2020/039674
§ 371 (c)(1),
(2) Date: Dec. 23, 2021

(87) PCT Pub. No.: WO2020/264201
PCT Pub. Date: Dec. 30, 2020

(65) Prior Publication Data

US 2022/0305012 A1 Sep. 29, 2022

(30) Foreign Application Priority Data

Jun. 26, 2019 (WO) ................ PCT/US2019/039333
Dec. 20, 2019 (WO) ................ PCT/US2019/067955

(51) Int. Cl.
*A61K 31/506* (2006.01)
*A61P 25/20* (2006.01)

(52) U.S. Cl.
CPC ............ *A61K 31/506* (2013.01); *A61P 25/20* (2018.01)

(58) Field of Classification Search
CPC .................................................. A61K 31/506
See application file for complete search history.

(56) References Cited

U.S. PATENT DOCUMENTS 9,416,109 B2 8/2016 Moniz et al.
2011/0040266 A1 2/2011 Blondino et al.
2012/0095031 A1 4/2012 Terauchi et al.
2017/0252342 A1* 9/2017 Moline ................ A61K 9/0053
2019/0201399 A1 7/2019 Moline et al.
2020/0179382 A1 6/2020 Beuckmann et al.

FOREIGN PATENT DOCUMENTS

WO WO 2017/197160 A1 11/2017
WO WO 2019/024845 A1 2/2019

OTHER PUBLICATIONS

Moline et al., (2019) "Efficacy and Tolerability of Lemborexant in Female and Male Subjects with Insomnia" *Sleep*, vol. 42, Issue Supplement 1, p. A150 (0368).
Moline et al., (2019) "Effect of Lemborexant on Sleep Architecture in Older Adults with Insomnia Disorder" *Sleep*, vol. 42, Issue Supplement 1, p. A150 (0369).
Genn, "Lemborexant Shows Promise for Sleep Disorders" HCP Live Network: Jun. 12, 2019 https://www.mdmag.com/medical-news/lemborexant-shows-promise-for-sleep-disorders.
International Search Report and Written Opinion for PCT/US2019/039333 dated Sep. 20, 2019 (10 pages).
International Search Report and Written Opinion for PCT/US2019/067955 dated May 21, 2020 (27 pages).
International Search Report and Written Opinion for PCT/US2020/039674 dated Sep. 30, 2020 (20 pages).
Murphy et al., "Lemborexant, A Dual Orexin Receptor Antagonist (DORA) for the Treatment of Insomnia Disorder: Results from a Bayesian, Adaptive, Randomized, Double-Blind, Placebo-Controlled Study", Journal of Clinical Sleep Medicine, vol. 13, No. 11, pp. 1289-1299; Aug. 25, 2017.
Rosenberg et al., "Comparison of Lemborexant With Placebo and Zolpidem Tartrate Extended Release for the Treatment of Older Adults With Insomnia Disorder A Phase 3 Randomized Clinical Trial", JAMA Network Open; vol. 2 No. 12; pp. 1-16; Dec. 27, 2019.
Center for Behavioral Health Statistics and Quality (2016) "Impact of the DSM-IV to DSM-5 Changes on the National Survey on Drug Use and Health", Substance Abuse and Mental Health Services Administration, Rockville, MD (262 pages).
ClinicalTrials.gov ID NCT02783729 (2018) "Study of the Efficacy and Safety of Lemborexant in Subjects 55 Years and Older With Insomnia Disorder (SUNRISE 1)" (24 pages).

(Continued)

*Primary Examiner* — Paul V Ward
(74) *Attorney, Agent, or Firm* — Finnegan, Henderson, Farabow, Garrett & Dunner, LLP

(57) ABSTRACT

Methods of improving subjective sleep efficiency, reducing subjective sleep onset latency, and/or reducing subjective wake after sleep onset in subjects comprising administering to the subject 5 mg or 10 mg of lemborexant or an equivalent dose of a pharmaceutically acceptable salt thereof are disclosed herein. Also disclosed herein is lemborexant or a pharmaceutically acceptable salt thereof for use in improving subjective sleep efficiency, reducing subjective sleep onset latency, and/or reducing subjective wake after sleep onset in a subject comprising administering to the subject 5 mg or 10 mg of lemborexant or an equivalent dose of a pharmaceutically acceptable salt thereof.

21 Claims, 21 Drawing Sheets

(56) References Cited

OTHER PUBLICATIONS

Gillette (2022) "DSM-5 Criteria for Insomnia", PsychCentral, URL: https://psychcentral.com/disorders/insomnia-symptoms (9 pages).
Hoffman (2021) "Most Patients Report Positive Lemborexant Treatment Effect in Insomnia", NeurologyLive, URL: https://www.neurologylive.com/view/patients-positive-lemborexant-dayvigo-treatment-effect-insomnia (3 pages).
Levenson et al. (2015) "The Pathophysiology of Insomnia", Chest, 147(4):1179-1192.
Mayo Clinic Staff (2024) "Insomnia—Symptoms and Causes", Mayo Clinic, URL: https://www.mayoclinic.org/diseases-conditions/insomnia/symptoms-causes/syc-20355167 (9 pages).
Mind (2021) "Sleeping pills and minor tranquillisers", URL: https://www.mind.org.uk/information-support/drugs-and-treatments/sleeping-pills-and-minor-tranquillisers/about-sleeping-pills-and-minor-tranquillisers/ (4 pages).
Pfizer (2016) "HALCION® triazolam tablets, USP CIV", Label Reference ID: 4029674, AccessData (15 pages).
Sanofi-Aventis (2008) "Ambien® (zolpidem tartrate) tablets", Label URL:https://www.accessdata.fda.gov/drugsatfda_docs/label/2008/019908s027lbl.pdf (22 pages).
Vargas et al. (2020) "Acute and Chronic Insomnia: What Has Time and/or Hyperarousal Got to Do with It?", Brain Sciences, 10(2):71 (12 pages).
Moline et al. (2019) "Patient-Reported Sleep Onset and Sleep Maintenance: Pooled Analyses of Lemborexant Phase 3 Studies" Sleep, 42(1):A150-A151 (0370).

* cited by examiner

**** P<0.0001 VS PBO; ++P<0.01, +++P<0.001, ++++P<0.0001 VS ZOL

P-VALUES BASED ON MIXED EFFECT REPEATED MEASURES MODEL EVALUATING THE LEAST SQUARES MEAN TREATMENT DIFFERENCE; ERROR BARS REPRESENT STANDARD ERROR
LEM5 = LEMBOREXANT 5 mg; LEM10 = LEMBOREXANT 10 mg; LSM = LEAST SQUARES MEAN; PBO = PLACEBO; ZOL = ZOLPIDEM TARTRATE EXTENDED RELEASE 6.25 mg

* P<0.001 VS ZOL; †P<0.01 VS ZOL; ‡P<0.0001 VS PBO; §P<0.0001 VS ZOL
BL, BASELINE; CI, CONFIDENCE INTERVAL; LEM5, LEMBOREXANT 5 mg; LEM10, LEMBOREXANT 10 mg; LSM, LEAST SQUARES MEAN;
N1, NON-REM SLEEP STAGE 1; PBO, PLACEBO; ZOL, ZOLPIDEM TARTRATE EXTENDED RELEASE 6.25 mg

* P<0.001 VS PBO; †P<0.05 VS ZOL
BL, BASELINE; CI, CONFIDENCE INTERVAL; LEM5, LEMBOREXANT 5 mg; LEM10, LEMBOREXANT 10 mg; LSM, LEAST SQUARES MEAN; N2, NON-REM SLEEP STAGE 2; PBO, PLACEBO; ZOL, ZOLPIDEM TARTRATE EXTENDED RELEASE 6.25 mg

* P<0.01 VS PBO; †P<0.05 VS PBO; ‡P<0.05 VS ZOL
BL, BASELINE; CI, CONFIDENCE INTERVAL; LEM5, LEMBOREXANT 5 mg; LEM10, LEMBOREXANT 10 mg; LSM, LEAST SQUARES MEAN; N3, NON-REM SLEEP STAGE 3; PBO, PLACEBO; ZOL, ZOLPIDEM TARTRATE EXTENDED RELEASE 6.25 mg

* P<0.0001 VS PBO; †P<0.0001 VS ZOL; ‡P<0.01 VS ZOL
BL, BASELINE; CI, CONFIDENCE INTERVAL; LEM5, LEMBOREXANT 5 mg; LEM10, LEMBOREXANT 10 mg; LSM, LEAST SQUARES MEAN; PBO, PLACEBO; ZOL, ZOLPIDEM TARTRATE EXTENDED RELEASE 6.25 mg

* P<0.0001 VS PBO; †P<0.0001 VS ZOL; ‡P<0.01 VS ZOL
BL, BASELINE; CI, CONFIDENCE INTERVAL; LEM5, LEMBOREXANT 5 mg; LEM10, LEMBOREXANT 10 mg; LSM, LEAST SQUARES MEAN; PBO, PLACEBO; ZOL, ZOLPIDEM TARTRATE EXTENDED RELEASE 6.25 mg

* P<0.001 VS PBO; †P<0.05 VS ZOL
BL, BASELINE; LEM5, LEMBOREXANT 5 mg; LEM10, LEMBOREXANT 10 mg; LSM, LEAST SQUARES MEAN; PBO, PLACEBO; SD, STANDARD DEVIATION; ZOL, ZOLPIDEM TARTRATE EXTENDED RELEASE 6.25 mg

LEMBOREXANT FOR TREATING SLEEP ISSUES

The present application is a national stage filing under 35 U.S.C. § 371 of International Application No. PCT/US2020/039674, filed on Jun. 25, 2020, which claims the benefit of priority to International Application No. PCT/US2019/039333, filed on Jun. 26, 2019; and International Application No. PCT/US2020/067955, filed on Dec. 20, 2019; the entire contents of each are incorporated herein by reference.

Novel methods and uses of lemborexant for improving sleep parameters such as subjective sleep efficiency, reducing subjective sleep onset latency, and/or reducing subjective wake after sleep onset are disclosed herein.

Sleep disorders such as insomnia are characterized by difficulties with sleep onset, sleep maintenance, or early morning awakening, in association with a complaint of impairment during the daytime. Currently available pharmacological treatments include benzodiazepines, non-benzodiazepine γ-aminobutyric acid receptor agonists, suvorexant, a recently approved dual orexin receptor antagonist (DORA), sedating antidepressants, melatonin and melatonin agonists, antihistamines, and other prescription and non-prescription medications with sedative properties.

Orexin neuropeptides (orexin-A and orexin-B) have been recognized as critical upstream controllers of most wake-promoting neurotransmitters via 2 G protein-coupled receptors, the orexin-1 receptor and the orexin-2 receptor. Small molecule antagonism of orexin receptors, particularly both orexin receptors, has recently emerged as an alternative approach to treat sleep issues. There exists an unmet medical need for a safe and effective therapy that is conveniently administered to address insomnia.

Lemborexant, also known as E2006, is a dual orexin receptor antagonist. It has been studied in clinical trials and found to possess advantageous properties, for example, reducing wake after sleep onset, sleep onset latency, and/or improving sleep efficiency.

In some embodiments, disclosed herein is a method of reducing subjective sleep onset latency (sSOL) in a subject comprising administering to the subject 5 mg or 10 mg of lemborexant or an equivalent dose of a pharmaceutically acceptable salt thereof, wherein the sSOL is reduced, relative to baseline, for at least one month.

In some embodiments, disclosed herein is a method of improving subjective sleep efficiency (sSE) in a subject comprising administering to the subject 5 mg or 10 mg of lemborexant or an equivalent dose of a pharmaceutically acceptable salt thereof, wherein the sSE is increased, relative to baseline, for at least one month.

In some embodiments, disclosed herein is a method of reducing subjective wake after sleep onset (sWASO) in a subject comprising administering to the subject 5 mg or 10 mg of lemborexant or an equivalent dose of a pharmaceutically acceptable salt thereof, wherein the sWASO is reduced, relative to baseline, for at least one month.

In some embodiments, disclosed herein is a method of identifying a subject responsive to treatment with lemborexant or a pharmaceutically acceptable salt thereof, comprising: (a) determining a pre-treatment period subjective wake after sleep onset (sWASO) of the subject; (b) administering to the subject 5 mg or 10 mg of lemborexant or an equivalent dose of a pharmaceutically acceptable salt thereof for a treatment period if the pre-treatment period sWASO is 60 minutes or more; (c) determining the post-treatment period sWASO of the subject; and (d) administering to the subject 5 mg or 10 mg of lemborexant or an equivalent dose of a pharmaceutically acceptable salt thereof if the post-treatment period sWASO is less than 60 minutes and the post-treatment period sWASO is 10 or more minutes less than the pre-treatment period sWASO.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form is achievable on maintaining reduction a time to sleep onset in Subjective Sleep Onset Latency (sSOL) compared to placebo during the treatment for at least one month.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form is achievable on maintaining reduction a time to sleep onset in Subjective Sleep Onset Latency (sSOL) compared to placebo during the treatment through six months.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form may be administered to a patient for at least one month, and wherein the dosage form is achievable on maintaining reduction a time to sleep onset in Subjective Sleep Onset Latency (sSOL) compared to placebo during the treatment for at least one month.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form may be administered to a patient for six months, and wherein the dosage form is achievable on maintaining reduction a time to sleep onset in Subjective Sleep Onset Latency (sSOL) compared to placebo during the treatment through six months.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of sleep efficiency in Subjective Sleep Efficiency (sSE) compared to placebo during the treatment for at least one month.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of sleep efficiency in Subjective Sleep Efficiency (sSE) compared to placebo during the treatment through six months.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form may be administered to a patient for at least one month, and wherein the dosage form is achievable on maintaining improvement of sleep efficiency in Subjective Sleep Efficiency (sSE) compared to placebo during the treatment for at least one month.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form may be administered to a patient for six months, and wherein the dosage form is achievable on maintaining improvement of sleep efficiency in Subjective Sleep Efficiency (sSE) compared to placebo during the treatment through six months.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of Wake After Sleep Onset (sWASO) compared to placebo during the treatment for at least one month.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of Wake After Sleep Onset (sWASO) compared to placebo during the treatment through six months.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form may be administered to a patient for at least one month, and wherein the dosage form is achievable on maintaining improvement of Wake After Sleep Onset (sWASO) compared to placebo during the treatment for at least one month.

In some embodiments, disclosed herein is a method for treating insomnia, comprising administering orally a dosage form comprising lemborexant or a pharmaceutically acceptable salt thereof at a single daily dose ranging from about 5 to 10 mg, wherein the dosage form may be administered to a patient for six months, and wherein the dosage form is achievable on maintaining improvement of Wake After Sleep Onset (sWASO) compared to placebo during the treatment through six months.

In some embodiments, disclosed herein is a method for treating insomnia in a subject comprising administering to the subject 5 mg or 10 mg of lemborexant or an equivalent dose of a pharmaceutically acceptable salt thereof, wherein subjective sleep onset latency is reduced, relative to baseline, for at least one month.

In some embodiments, disclosed herein is a method for treating insomnia in a subject comprising administering to the subject 5 mg or 10 mg of lemborexant or an equivalent dose of a pharmaceutically acceptable salt thereof, wherein subjective sleep efficiency is increased, relative to baseline, for at least one month.

In some embodiments, disclosed herein is a method for treating insomnia in a subject comprising administering to the subject 5 mg or 10 mg of lemborexant or an equivalent dose of a pharmaceutically acceptable salt thereof, wherein subjective wake after sleep onset is reduced, relative to baseline, for at least one month.

In some embodiments, disclosed herein is a method for treating insomnia, comprising administering orally a dosage form comprising 5 mg or 10 mg of lemborexant or an equivalent dose of a pharmaceutically acceptable salt thereof, wherein the method comprises orally administering the 5 mg dose of lemborexant or a pharmaceutically acceptable salt thereof to a patient no more than once per night and within a few minutes before going to bed, with at least 7 hours remaining before the planned time of awakening, wherein if the 5 mg dose is well tolerated but not effective, then the dose can be increased to 10 mg once daily, wherein the dosage form is achievable on maintaining reduction a time to sleep onset in subjective Sleep Onset Latency (sSOL) during a treatment for at least one month, and wherein the sSOL is reduced by at least 15 minutes relative to baseline.

In some embodiments, disclosed herein is a method for treating insomnia, comprising administering orally a dosage form comprising 5 mg or 10 mg of lemborexant or an equivalent dose of a pharmaceutically acceptable salt thereof, wherein the method comprises orally administering the 5 mg dose of lemborexant or a pharmaceutically acceptable salt thereof to a patient no more than once per night, immediately before going to bed, with at least 7 hours remaining before the planned time of awakening, wherein the daily dose can be increased to 10 mg based on clinical response and tolerability, wherein the dosage form is achievable on maintaining reduction a time to sleep onset in subjective Sleep Onset Latency (sSOL) during a treatment for at least one month, and wherein the sSOL is reduced by at least 15 minutes relative to baseline.

In some embodiments, disclosed herein is a method for treating insomnia, comprising administering orally a dosage form comprising 5 mg or 10 mg of lemborexant or an equivalent dose of a pharmaceutically acceptable salt thereof, wherein the method comprises orally administering the 5 mg dose of lemborexant or a pharmaceutically acceptable salt thereof to a patient no more than once per night and within a few minutes before going to bed, with at least 7 hours remaining before the planned time of awakening, wherein if the 5 mg dose is well tolerated but not effective, then the dose can be increased to 10 mg once daily, wherein the dosage form is achievable on maintaining improvement of sleep efficiency in subjective Sleep Efficiency (sSE) during a treatment for at least one month, and wherein the sSE is improved by at least 4% relative to baseline.

In some embodiments, disclosed herein is a method for treating insomnia, comprising administering orally a dosage form comprising 5 mg or 10 mg of lemborexant or an equivalent dose of a pharmaceutically acceptable salt thereof, wherein the method comprises administering orally the 5 mg dose of lemborexant or a pharmaceutically acceptable salt thereof to a patient no more than once per night, immediately before going to bed, with at least 7 hours remaining before the planned time of awakening, wherein the daily dose may be increased to 10 mg based on clinical response and tolerability, wherein the dosage form is achievable on maintaining improvement of sleep efficiency in subjective Sleep Efficiency (sSE) during a treatment for at least one month, and wherein the sSE is improved by at least 4%, relative to baseline.

In some embodiments, disclosed herein is a method for treating insomnia, comprising administering orally a dosage form comprising 5 mg or 10 mg of lemborexant or an equivalent dose of a pharmaceutically acceptable salt thereof, wherein the method comprising orally administering the 5 mg dose of lemborexant or a pharmaceutically acceptable salt thereof to a patient no more than once per night and within a few minutes before going to bed, with at least 7 hours remaining before the planned time of awakening, wherein if the 5 mg dose is well tolerated but not effective, then the dose can be increased to 10 mg once daily, wherein the dosage form is achievable on maintaining improvement of subjective Wake After Sleep Onset (sWASO) during a treatment for at least one month, and wherein the sWASO is reduced by at least 29 minutes relative to baseline.

In some embodiments, disclosed herein is a method for treating insomnia, comprising administering orally a dosage form comprising 5 mg or 10 mg of lemborexant or an equivalent dose of a pharmaceutically acceptable salt thereof, wherein the method comprises administering orally the 5 mg dose of lemborexant or a pharmaceutically acceptable salt thereof to a patient no more than once per night, immediately before going to bed, with at least 7 hours remaining before the planned time of awakening, wherein the daily dose may be increased to 10 mg based on clinical response and tolerability, wherein the dosage form is achievable on maintaining improvement of subjective Wake After Sleep Onset (sWASO) during a treatment for at least one month, and wherein the sWASO is reduced by at least 29 minutes relative to baseline.

In some embodiments, disclosed herein is a method for treating insomnia, characterized by difficulties with sleep onset and/or sleep maintenance, with or without associated impairment in daily functioning, comprising administering to the subject 5 mg or 10 mg of lemborexant or an equivalent dose of a pharmaceutically acceptable salt thereof.

In some embodiments, administration of lemborexant or a pharmaceutically acceptable salt thereof does not significantly affect postural stability of the subject, relative to placebo.

Figure 1:
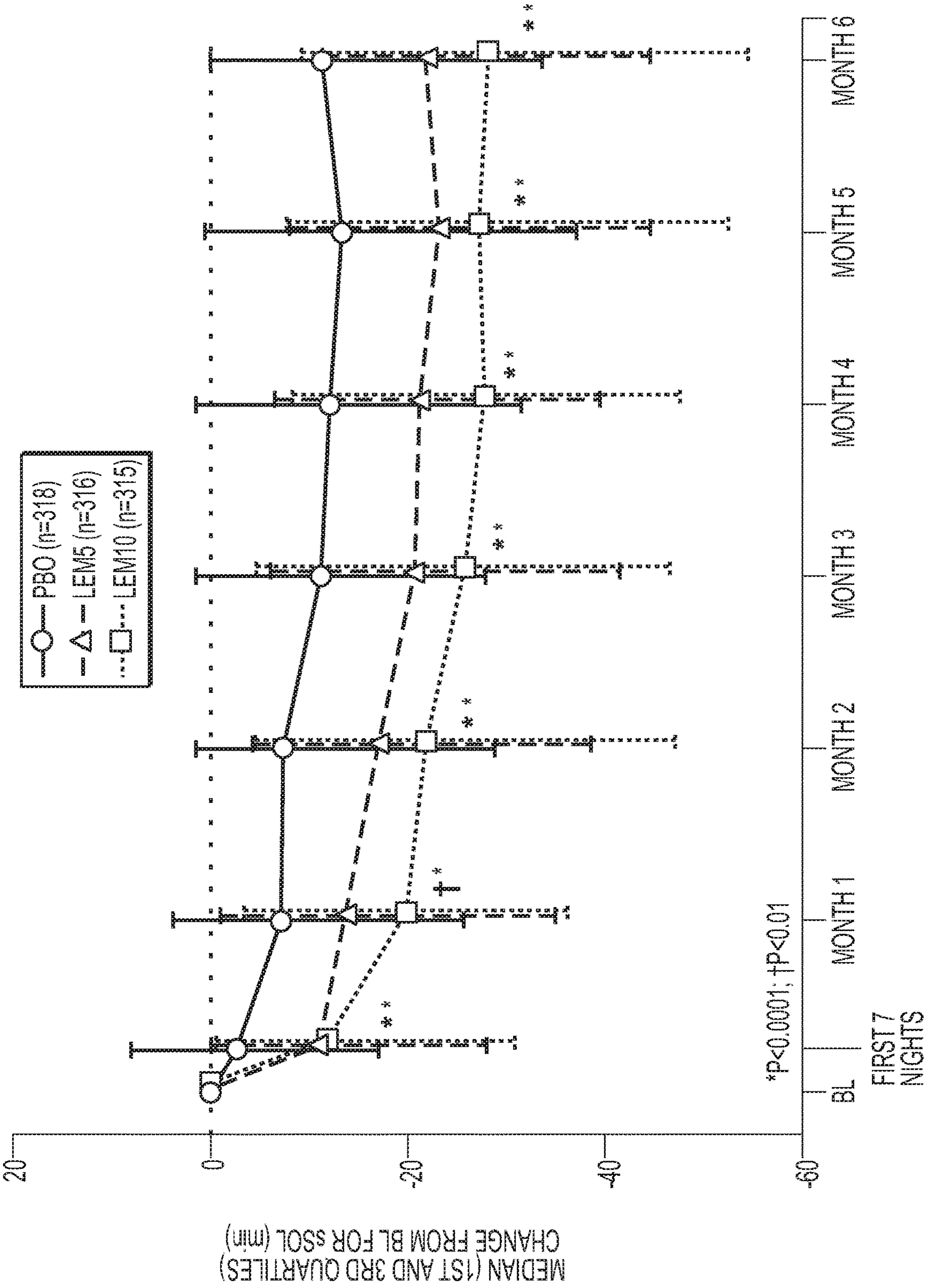
FIG. 1 shows the change from baseline in the $1^{st}$ and $3^{rd}$ quartile median time, as a function of treatment duration, for subjective sleep onset latency in patients treated with placebo, 5 mg of lemborexant, or 10 mg of lemborexant.

As used herein, the following definitions shall apply unless otherwise indicated.

As used herein, the term "a" refers to one or more.

As used herein, the term "lemborexant" refers to a compound having the structure:

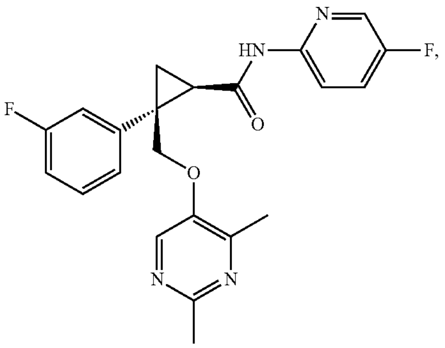 [SMILES: Cc1ncc(OC[C@@]2(c3cccc(F)c3)C[C@H]2C(=O)Nc2ccc(F)cn2)c(C)n1]

also known as (1R,2S)-2-(((2,4-dimethylpyrimidin-5-yl)oxy)methyl)-2-(3-fluorophenyl)-N-(5-fluoropyridin-2-yl)cyclopropanecarboxamide or (1R,2S)-2-(((2,4-dimethylpyrimidin-5-yl)oxy)methyl)-2-(3-fluorophenyl)-N-(5-fluoropyridin-2-yl)cyclopropane-1-carboxamide.

As used herein, the term "therapeutically effective amount" means an amount sufficient to effect an intended result including, but not limited to, a reduction in subjective sleep onset latency, an improvement in subjective sleep efficiency, a reduction in subjective wake after sleep onset, or improvement in insomnia. The present disclosures involve administration to a subject of a therapeutically effective amount of lemborexant or a pharmaceutically acceptable salt thereof. In some embodiments, the therapeutically effective amount is 5 mg of lemborexant or an equivalent dose of a pharmaceutically acceptable salt thereof. In some embodiments, the therapeutically effective amount is 10 mg of lemborexant or an equivalent dose of a pharmaceutically acceptable salt thereof.

As used herein, the term "pharmaceutically acceptable salt" is a salt that retains the desired biological activity of the parent compound and does not impart undesired toxicological effects. Examples of such salts include, but are not limited to: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes, et al., *J. Pharm. Sci.,* 2005, 94, 10; and Berge, et al., *J. Pharm. Sci.,* 1977, 66, 1, which are incorporated herein by reference.

In some embodiments, lemborexant or the pharmaceutically acceptable salt thereof is administered in the form of a composition. The compositions may be in any suitable dosage form. In some embodiments, lemborexant or the pharmaceutically acceptable salt thereof is in a solid dosage form, such as, for example, capsules, granules, lozenges, pellets, pills, powders, suspensions, and tablets.

In some embodiments, the composition further comprises at least one additional pharmaceutically acceptable component. In some embodiments, the at least one additional pharmaceutically acceptable component is chosen from pharmaceutically acceptable carriers, pharmaceutically acceptable vehicles, and pharmaceutically acceptable excipients.

As used herein, the term "pharmaceutically acceptable" means that a carrier, diluent, excipient, or vehicle is compatible with other components of a composition and is nontoxic non-toxic to a subject.

As used herein, the term "pharmaceutically acceptable excipient" means an inactive ingredient used as a vehicle (e.g., water, capsule shell, etc.), a diluent, or a component to constitute a dosage form or pharmaceutical composition comprising a drug such as a therapeutic agent. The term also encompasses an inactive ingredient that imparts cohesive function (e.g., binder), disintegrating function (e.g., disintegrator), lubricant function (e.g., lubricating agent), and/or the other function (e.g., solvent, surfactant, etc.) to the composition.

As used herein, the term "subject" means an animal subject, such as a mammalian subject, and for example, a human being. As used herein, the subject may be of any age. In some embodiments, the subject may be 18 years or older. In some embodiments, the subject may be 55 years or older.

As used herein, the terms "treatment" and "treating" refer to an approach for obtaining beneficial or desired results including, but not limited to, therapeutic benefit and/or prophylactic benefit.

As used herein, the term "subjective sleep onset latency", abbreviated as "sSOL", means the estimated number of minutes from the time that the subject attempted to sleep until sleep onset. In some embodiments, sSOL is derived from data entered in a subject's Sleep Diary.

As used herein, the term "subjective wake after sleep onset", abbreviated as "sWASO", means the sum of estimated minutes of wake during the night after initial sleep onset until the time the subject stopped trying to sleep for the night, operationalized as the time the subject got out of bed for the day. In some embodiments, sWASO is derived from data entered in a subject's Sleep Diary. As used herein, an "improvement of sWASO" means a reduction in sWASO.

As used herein, the term "subjective total sleep time", abbreviated as "sTST", means the derived minutes of sleep from sleep onset until the time the subject stopped trying to sleep for the night. In some embodiments, sTST is derived from data entered in a subject's Sleep Diary.

As used herein, the term "subjective sleep efficiency", abbreviated as "sSE", means the proportion of sTST per subjective time spent in bed, calculated as the interval from the time the subject reports attempting to sleep until the time the subject stopped trying to sleep for the night (operationalized as the time the subject got out of bed for the day), and time spent asleep derived from subjective time spent in bed minus sWASO. As used herein, an "improvement of sleep efficiency in Subjective Sleep Efficiency (sSE)" means an increase in sleep efficiency in Subjective Sleep Efficiency (sSE).

Subjective determinations of the aforementioned sleep parameters are known in the art. In some embodiments, the sleep parameter is determined by subjective measurements, such as, for example, asking the subject, maintaining a sleep diary, or assessment via a standardized questionnaire regarding how restorative and undisturbed sleep has been (e.g., Pittsburgh Sleep Quality Index (Buysse et al., Psychiatry Research (1989), 28(2), 193-213)).

In some embodiments, sleep diaries were used to assess sleep parameters reported by subjects (i.e., subjective assessments) including subjective sleep onset latency (sSOL), subjective sleep efficiency (sSE), subjective WASO (sWASO), and subjective total sleep time (sTST). Subjects were instructed to complete the Sleep Diary developed based on the consensus Sleep Diary as described in Carney et al., "The consensus sleep diary: standardizing prospective sleep self-monitoring," *Sleep* 2012; 35(2):287-302. In some embodiments, the Sleep Diary was used to assess the subject's global perception of quality of sleep on the previous night with the following question: "How would you rate the quality of your sleep last night?" Subjects rated the quality of their sleep on a scale from 1 to 9, with 1 being extremely poor and 9 being extremely good. In some embodiments, the Sleep Diary was used to assess subjective ratings of morning sleepiness with the following question: "How alert/sleepy do you feel this morning?" Subjects rated their sleepiness/alertness level on a Likert scale from 1 to 9, with 1 being extremely sleepy and 9 being extremely alert.

As used herein, the term "Insomnia Severity Index", abbreviated as "ISI", is an index calculated using a 7-item, self-report questionnaire assessing the nature, severity, and impact of insomnia (see Bastien, C. H., et al. "Validation of the Insomnia Severity Index as an outcome measure for insomnia research." *Sleep Med.* 2001; 2(4): 297-307). The questionnaire evaluates: (1) severity of sleep onset; (2) sleep maintenance; (3) early morning awakening problems; (4) sleep dissatisfaction; (5) interference caused by sleep difficulties with daytime functioning; (6) noticeability of sleep problems by others; and (7) distress caused by the sleep difficulties. A 5-point scale is used to rate each item (0=no problem to 4=very severe problem) yielding a total score from 0 to 28. Total ISI score (items (1)-(7)) and daytime functioning (items (4)-(7)) are analyzed separately.

As used herein, the term "insomnia" means a disorder defined by the Diagnostic and Statistical Manual of Mental Disorders, 5th Edition (2013; "DSM-V") having the following diagnostic criteria:

A. A predominant complaint of the subject is dissatisfaction with sleep quantity or quality, associated with one (or more) of the following symptoms:
   1. Difficulty initiating sleep (in children, this may manifest as difficulty initiating sleep without caregiver intervention).
   2. Difficulty maintaining sleep, characterized by frequent awakenings or problems returning to sleep after awakenings (in children, this may manifest as difficulty returning to sleep without caregiver intervention).
   3. Early-morning awakening with inability to return to sleep.

B. The sleep disturbances cause clinically significant distress or impairment in social, occupational, educational, academic, behavioral, or other important areas of functioning.

C. The sleep difficulty occurs at least 3 nights per week.

D. The sleep difficulty is present for at least 3 months.

E. The sleep difficulty occurs despite adequate opportunity for sleep.

F. The insomnia is not better explained by and does not occur exclusively during the course of another sleep-wake disorder (e.g., narcolepsy, breathing-related sleep disorder, circadian rhythm sleep-wake disorder, a parasomnia).

G. The insomnia is not attributable to the physiological effects of a substance (e.g., a drug of abuse, a medication).

H. Coexisting mental disorders and medical conditions do not adequately explain the predominant complaint of insomnia.

The term "insomnia" also means a sleep disorder characterized by symptoms including, but not limited to, difficulty in falling asleep, difficulty in staying asleep, intermittent wakefulness, and/or waking up too early. The term also encompasses daytime symptoms such as sleepiness, anxiety, impaired concentration, impaired memory, and irritability. Types of insomnia suitable for treatment with lemborexant or a pharmaceutically acceptable salt thereof include short-term insomnia and chronic insomnia.

As used herein, the term "latency to persistent sleep", abbreviated as "LPS." means the minutes from lights off to the first epoch of 20 consecutive epochs (10 minutes) of non-wakefulness.

In some embodiments, a sleep parameter is determined objectively using polysomnography. Polysomnography is the monitoring of multiple electrophysiological parameters during sleep and generally includes measurement of EEG activity, electro-oculographic activity and electromyographic activity, as well as other measurements. Using these results, along with observations, the following can be objectively measured: latency to persistent sleep (LPS), wake after sleep onset (WASO), wake after sleep onset in the second half of the night (WASO2H), sleep efficiency (SE), and total sleep time (TST).

As used herein, the term "about" means±10% of the recited value. For example, if an embodiment is directed to a method where subjective sleep onset latency is reduced by about 10 minutes, then the subjective sleep onset latency is reduced by an amount of time ranging from 9 minutes to 11 minutes.

As used herein, the term "immediately before going to bed" means within five minutes of commencing preparations for sleep or getting into bed. In some embodiments, a patient takes lemborexant or a pharmaceutically acceptable salt thereof within five minutes of commencing preparations for sleep. In some embodiments, a patient takes lemborexant or a pharmaceutically acceptable salt thereof within two minutes of commencing preparations for sleep. In some embodiments, a patient takes lemborexant or a pharmaceutically acceptable salt thereof within five minutes of getting into bed. In some embodiments, a patient takes lemborexant or a pharmaceutically acceptable salt thereof within two minutes of getting into bed. In some embodiments, a patient takes lemborexant or a pharmaceutically acceptable salt thereof once in bed.

Methods of Reducing Subjective Sleep Onset Latency (sSOL)

Provided herein is a method of reducing subjective sleep onset latency (sSOL) in a subject comprising administering to the subject 5 mg or 10 mg of lemborexant or an equivalent dose of a pharmaceutically acceptable salt thereof. Also disclosed herein is lemborexant or a pharmaceutically acceptable salt thereof for use in reducing sSOL in a subject comprising administering to the subject 5 mg or 10 mg of lemborexant or an equivalent dose of a pharmaceutically acceptable salt thereof.

In some embodiments, the sSOL is reduced for at least one week. In some embodiments, the sSOL is reduced for at least one month. In some embodiments, the sSOL is reduced for at least two months. In some embodiments, the sSOL is reduced for at least three months. In some embodiments, the sSOL is reduced for at least 6 months. In some embodiments, the sSOL is reduced for at least 9 months. In some embodiments, the sSOL is reduced for at least 12 months. In some embodiments, the sSOL is reduced for at least 18 months. In some embodiments, the sSOL is reduced for 2 years or more.

In some embodiments, the sSOL is reduced for at least one week, relative to baseline. In some embodiments, the sSOL is reduced for at least one month, relative to baseline. In some embodiments, the sSOL is reduced for at least two months, relative to baseline. In some embodiments, the sSOL is reduced for at least three months, relative to baseline. In some embodiments, the sSOL is reduced for at least 6 months, relative to baseline. In some embodiments, the sSOL is reduced for at least 9 months, relative to baseline. In some embodiments, the sSOL is reduced for at least 12 months, relative to baseline. In some embodiments, the sSOL is reduced for at least 18 months, relative to baseline. In some embodiments, the sSOL is reduced for 2 years or more, relative to baseline.

In some embodiments, lemborexant or salt thereof is administered to the subject for at least one month. In some embodiments, lemborexant or salt thereof is administered to the subject for at least two months. In some embodiments, lemborexant or salt thereof is administered to the subject for at least three months. In some embodiments, lemborexant or salt thereof is administered to the subject for at least 6 months. In some embodiments, lemborexant or salt thereof is administered to the subject for at least 9 months. In some embodiments, lemborexant or salt thereof is administered to the subject for at least 12 months. In some embodiments, lemborexant or salt thereof is administered to the subject for at least 18 months. In some embodiments, lemborexant or salt thereof is administered to the subject for two years or more.

In some embodiments, the sSOL is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to baseline. In some embodiments, the sSOL is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 31 minutes, at least 32 minutes, at least 33 minutes, at least 34 minutes, at least 35 minutes, at least 36 minutes, at least 37 minutes, at least 38 minutes, at least 39 minutes, at least 40 minutes, at least 41 minutes, at least 42 minutes, at least 43 minutes, at least 44 minutes, or at least 45 minutes, relative to baseline.

In some embodiments, the sSOL is reduced by at least 1 minute, relative to baseline. In some embodiments, the sSOL is reduced by at least 2 minutes, relative to baseline. In some embodiments, the sSOL is reduced by at least 3 minutes, relative to baseline. In some embodiments, the sSOL is reduced by at least 4 minutes, relative to baseline. In some embodiments, the sSOL is reduced by at least 5 minutes, relative to baseline. In some embodiments, the sSOL is reduced by at least 6 minutes, relative to baseline. In some embodiments, the sSOL is reduced by at least 7 minutes, relative to baseline. In some embodiments, the sSOL is reduced by at least 8 minutes, relative to baseline. In some embodiments, the sSOL is reduced by at least 9 minutes, relative to baseline. In some embodiments, the sSOL is reduced by at least 9 minutes, relative to baseline.

In some embodiments, the sSOL is reduced by at least 11 minutes, relative to baseline. In some embodiments, the sSOL is reduced by at least 12 minutes, relative to baseline. In some embodiments, the sSOL is reduced by at least 13 minutes, relative to baseline. In some embodiments, the sSOL is reduced by at least 14 minutes, relative to baseline. In some embodiments, the sSOL is reduced by at least 15 minutes, relative to baseline. In some embodiments, the sSOL is reduced by at least 16 minutes, relative to baseline. In some embodiments, the sSOL is reduced by at least 17 minutes, relative to baseline. In some embodiments, the sSOL is reduced by at least 18 minutes, relative to baseline. In some embodiments, the sSOL is reduced by at least 19 minutes, relative to baseline. In some embodiments, the sSOL is reduced by at least 20 minutes, relative to baseline.

In some embodiments, the sSOL is reduced by at least 21 minutes, relative to baseline. In some embodiments, the sSOL is reduced by at least 22 minutes, relative to baseline. In some embodiments, the sSOL is reduced by at least 23 minutes, relative to baseline. In some embodiments, the sSOL is reduced by at least 24 minutes, relative to baseline. In some embodiments, the sSOL is reduced by at least 25 minutes, relative to baseline. In some embodiments, the sSOL is reduced by at least 26 minutes, relative to baseline. In some embodiments, the sSOL is reduced by at least 27 minutes, relative to baseline. In some embodiments, the sSOL is reduced by at least 28 minutes, relative to baseline. In some embodiments, the sSOL is reduced by at least 29 minutes, relative to baseline.

In some embodiments, the sSOL is reduced by at least 30 minutes, relative to baseline. In some embodiments, the sSOL is reduced by at least 31 minutes, relative to baseline. In some embodiments, the sSOL is reduced by at least 32 minutes, relative to baseline. In some embodiments, the sSOL is reduced by at least 33 minutes, relative to baseline. In some embodiments, the sSOL is reduced by at least 34 minutes, relative to baseline. In some embodiments, the sSOL is reduced by at least 35 minutes, relative to baseline. In some embodiments, the sSOL is reduced by at least 36 minutes, relative to baseline. In some embodiments, the sSOL is reduced by at least 37 minutes, relative to baseline. In some embodiments, the sSOL is reduced by at least 38 minutes, relative to baseline. In some embodiments, the sSOL is reduced by at least 39 minutes, relative to baseline. In some embodiments, the sSOL is reduced by at least 40 minutes, relative to baseline.

In some embodiments, the sSOL is reduced by about 1 minute, relative to baseline. In some embodiments, the sSOL is reduced by about 2 minutes, relative to baseline. In some embodiments, the sSOL is reduced by about 3 minutes, relative to baseline. In some embodiments, the sSOL is reduced by about 4 minutes, relative to baseline. In some embodiments, the sSOL is reduced by about 5 minutes, relative to baseline. In some embodiments, the sSOL is reduced by about 6 minutes, relative to baseline. In some embodiments, the sSOL is reduced by about 7 minutes, relative to baseline. In some embodiments, the sSOL is reduced by about 8 minutes, relative to baseline. In some embodiments, the sSOL is reduced by about 9 minutes, relative to baseline. In some embodiments, the sSOL is reduced by about 9 minutes, relative to baseline.

In some embodiments, the sSOL is reduced by about 11 minutes, relative to baseline. In some embodiments, the sSOL is reduced by about 12 minutes, relative to baseline. In some embodiments, the sSOL is reduced by about 13 minutes, relative to baseline. In some embodiments, the sSOL is reduced by about 14 minutes, relative to baseline. In some embodiments, the sSOL is reduced by about 15 minutes, relative to baseline. In some embodiments, the sSOL is reduced by about 16 minutes, relative to baseline. In some embodiments, the sSOL is reduced by about 17 minutes, relative to baseline. In some embodiments, the sSOL is reduced by about 18 minutes, relative to baseline. In some embodiments, the sSOL is reduced by about 19 minutes, relative to baseline. In some embodiments, the sSOL is reduced by about 20 minutes, relative to baseline.

In some embodiments, the sSOL is reduced by about 21 minutes, relative to baseline. In some embodiments, the sSOL is reduced by about 22 minutes, relative to baseline. In some embodiments, the sSOL is reduced by about 23 minutes, relative to baseline. In some embodiments, the sSOL is reduced by about 24 minutes, relative to baseline. In some embodiments, the sSOL is reduced by about 25 minutes, relative to baseline. In some embodiments, the sSOL is reduced by about 26 minutes, relative to baseline. In some embodiments, the sSOL is reduced by about 27 minutes, relative to baseline. In some embodiments, the sSOL is reduced by about 28 minutes, relative to baseline. In some embodiments, the sSOL is reduced by about 29 minutes, relative to baseline.

In some embodiments, the sSOL is reduced by about 30 minutes, relative to baseline. In some embodiments, the sSOL is reduced by about 31 minutes, relative to baseline.

In some embodiments, the sSOL is reduced by about 32 minutes, relative to baseline. In some embodiments, the sSOL is reduced by about 33 minutes, relative to baseline. In some embodiments, the sSOL is reduced by about 34 minutes, relative to baseline. In some embodiments, the sSOL is reduced by about 35 minutes, relative to baseline. In some embodiments, the sSOL is reduced by about 36 minutes, relative to baseline. In some embodiments, the sSOL is reduced by about 37 minutes, relative to baseline. In some embodiments, the sSOL is reduced by about 38 minutes, relative to baseline. In some embodiments, the sSOL is reduced by about 39 minutes, relative to baseline. In some embodiments, the sSOL is reduced by about 40 minutes, relative to baseline.

In some embodiments, 5 mg of lemborexant or an equivalent dose of a pharmaceutically acceptable salt thereof is administered to a subject and the sSOL is reduced by about 20 minutes. In some embodiments, 5 mg of lemborexant or an equivalent dose of a pharmaceutically acceptable salt thereof is administered to a subject and the sSOL is reduced by about 25 minutes. In some embodiments, 5 mg of lemborexant or an equivalent dose of a pharmaceutically acceptable salt thereof is administered to a subject and the sSOL is reduced by about 30 minutes.

In some embodiments, 5 mg of lemborexant or an equivalent dose of a pharmaceutically acceptable salt thereof is administered to a subject and the sSOL is reduced by at least 20 minutes. In some embodiments, 5 mg of lemborexant or an equivalent dose of a pharmaceutically acceptable salt thereof is administered to a subject and the sSOL is reduced by at least 25 minutes. In some embodiments, 5 mg of lemborexant or an equivalent dose of a pharmaceutically acceptable salt thereof is administered to a subject and the sSOL is reduced at least 30 minutes.

In some embodiments, 10 mg of lemborexant or an equivalent dose of a pharmaceutically acceptable salt thereof is administered to a subject and the sSOL is reduced by about 25 minutes. In some embodiments, 10 mg of lemborexant or an equivalent dose of a pharmaceutically acceptable salt thereof is administered to a subject and the sSOL is reduced by about 30 minutes. In some embodiments, 10 mg of lemborexant or an equivalent dose of a pharmaceutically acceptable salt thereof is administered to a subject and the sSOL is reduced by about 35 minutes.

In some embodiments, 10 mg of lemborexant or an equivalent dose of a pharmaceutically acceptable salt thereof is administered to a subject and the sSOL is reduced by at least 24 minutes. In some embodiments, 10 mg of lemborexant or an equivalent dose of a pharmaceutically acceptable salt thereof is administered to a subject and the sSOL is reduced by about 27 minutes. In some embodiments, 10 mg of lemborexant or an equivalent dose of a pharmaceutically acceptable salt thereof is administered to a subject and the sSOL is reduced by about 32 minutes.

In some embodiments, sSOL is 1 minute or less, 2 minutes or less, 3 minutes or less, 4 minutes or less, 5 minutes or less, 5 minutes or less, 6 minutes or less, 7 minutes or less, 8 minutes or less, 9 minutes or less, 10 minutes or less, 11 minutes or less, 12 minutes or less, 13 minutes or less, 14 minutes or less, 15 minutes or less, 16 minutes or less, 17 minutes or less, 18 minutes or less, 19 minutes or less, 20 minutes or less, 21 minutes or less, 22 minutes or less, 23 minutes or less, 24 minutes or less, 25 minutes or less, 26 minutes or less, 27 minutes or less, 28 minutes or less, 29 minutes or less, 30 minutes or less, 31 minutes or less, 32 minutes or less, 33 minutes or less, 34 minutes or less, 35 minutes or less, 36 minutes or less, 37 minutes or less, 38 minutes or less, 39 minutes or less, 40 minutes or less, 41 minutes or less, 42 minutes or less, 43 minutes or less, 44 minutes or less, or 45 minutes or less.

In some embodiments, sSOL is 1 minute or less. In some embodiments, sSOL is 2 minutes or less. In some embodiments, sSOL is 3 minutes or less. In some embodiments, sSOL is 4 minutes or less. In some embodiments, sSOL is 5 minutes or less. In some embodiments, sSOL is 6 minutes or less. In some embodiments, sSOL is 7 minutes or less. In some embodiments, sSOL is 8 minutes or less. In some embodiments, sSOL is 9 minutes or less. In some embodiments, sSOL is 10 minutes or less.

In some embodiments, sSOL is 11 minutes or less. In some embodiments, sSOL is 12 minutes or less. In some embodiments, sSOL is 13 minutes or less. In some embodiments, sSOL is 14 minutes or less. In some embodiments, sSOL is 15 minutes or less. In some embodiments, sSOL is 16 minutes or less. In some embodiments, sSOL is 17 minutes or less. In some embodiments, sSOL is 18 minutes or less. In some embodiments, sSOL is 19 minutes or less.

In some embodiments, sSOL is 20 minutes or less. In some embodiments, sSOL is 21 minutes or less. In some embodiments, sSOL is 22 minutes or less. In some embodiments, sSOL is 23 minutes or less. In some embodiments, sSOL is 24 minutes or less. In some embodiments, sSOL is 25 minutes or less. In some embodiments, sSOL is 26 minutes or less. In some embodiments, sSOL is 27 minutes or less. In some embodiments, sSOL is 28 minutes or less. In some embodiments, sSOL is 29 minutes or less.

In some embodiments, sSOL is 30 minutes or less. In some embodiments, sSOL is 31 minutes or less. In some embodiments, sSOL is 32 minutes or less. In some embodiments, sSOL is 33 minutes or less. In some embodiments, sSOL is 34 minutes or less. In some embodiments, sSOL is 35 minutes or less. In some embodiments, sSOL is 36 minutes or less. In some embodiments, sSOL is 37 minutes or less. In some embodiments, sSOL is 38 minutes or less. In some embodiments, sSOL is 39 minutes or less.

In some embodiments, sSOL is 40 minutes or less. In some embodiments, sSOL is 41 minutes or less. In some embodiments, sSOL is 42 minutes or less. In some embodiments, sSOL is 43 minutes or less. In some embodiments, sSOL is 44 minutes or less. In some embodiments, sSOL is 45 minutes or less.

In some embodiments, sSOL is about 1 minute or less, about 2 minutes or less, about 3 minutes or less, about 4 minutes or less, about 5 minutes or less, about 6 minutes or less, about 7 minutes or less, about 8 minutes or less, about 9 minutes or less, about 10 minutes or less, about 11 minutes or less, about 12 minutes or less, about 13 minutes or less, about 14 minutes or less, about 15 minutes or less, about 16 minutes or less, about 17 minutes or less, about 18 minutes or less, about 19 minutes or less, about 20 minutes or less, about 21 minutes or less, about 22 minutes or less, about 23 minutes or less, about 24 minutes or less, about 25 minutes or less, about 26 minutes or less, about 27 minutes or less, about 28 minutes or less, about 29 minutes or less, about 30 minutes or less, about 31 minutes or less, about 32 minutes or less, about 33 minutes or less, about 34 minutes or less, about 35 minutes or less, about 36 minutes or less, about 37 minutes or less, about 38 minutes or less, about 39 minutes or less, about 40 minutes or less, about 41 minutes or less, about 42 minutes or less, about 43 minutes or less, about 44 minutes or less, or about 45 minutes or less.

In some embodiments, sSOL is about 1 minute or less. In some embodiments, sSOL is about 2 minutes or less. In some embodiments, sSOL is about 3 minutes or less. In some embodiments, sSOL is about 4 minutes or less. In some embodiments, sSOL is about 5 minutes or less. In some embodiments, sSOL is about 6 minutes or less. In some embodiments, sSOL is about 7 minutes or less. In some embodiments, sSOL is about 8 minutes or less. In some embodiments, sSOL is about 9 minutes or less. In some embodiments, sSOL is about 10 minutes or less.

In some embodiments, sSOL is about 11 minutes or less. In some embodiments, sSOL is about 12 minutes or less. In some embodiments, sSOL is about 13 minutes or less. In some embodiments, sSOL is about 14 minutes or less. In some embodiments, sSOL is about 15 minutes or less. In some embodiments, sSOL is about 16 minutes or less. In some embodiments, sSOL is about 17 minutes or less. In some embodiments, sSOL is about 18 minutes or less. In some embodiments, sSOL is about 19 minutes or less.

In some embodiments, sSOL is about 20 minutes or less. In some embodiments, sSOL is about 21 minutes or less. In some embodiments, sSOL is about 22 minutes or less. In some embodiments, sSOL is about 23 minutes or less. In some embodiments, sSOL is about 24 minutes or less. In some embodiments, sSOL is about 25 minutes or less. In some embodiments, sSOL is about 26 minutes or less. In some embodiments, sSOL is about 27 minutes or less. In some embodiments, sSOL is about 28 minutes or less. In some embodiments, sSOL is about 29 minutes or less.

In some embodiments, sSOL is about 30 minutes or less. In some embodiments, sSOL is about 31 minutes or less. In some embodiments, sSOL is about 32 minutes or less. In some embodiments, sSOL is about 33 minutes or less. In some embodiments, sSOL is about 34 minutes or less. In some embodiments, sSOL is about 35 minutes or less. In some embodiments, sSOL is about 36 minutes or less. In some embodiments, sSOL is about 37 minutes or less. In some embodiments, sSOL is about 38 minutes or less. In some embodiments, sSOL is about 39 minutes or less.

In some embodiments, sSOL is about 40 minutes or less. In some embodiments, sSOL is about 41 minutes or less. In some embodiments, sSOL is about 42 minutes or less. In some embodiments, sSOL is about 43 minutes or less. In some embodiments, sSOL is about 44 minutes or less. In some embodiments, sSOL is about 45 minutes or less.

In some embodiments, the subject has insomnia.

Methods of Reducing Subjective Wake After Sleep Onset (sWASO)

Provided herein is a method of reducing subjective wake after sleep onset (sWASO) in a subject comprising administering to the subject 5 mg or 10 mg of lemborexant or an equivalent dose of a pharmaceutically acceptable salt thereof. Also disclosed herein is lemborexant or a pharmaceutically acceptable salt thereof for use in reducing sWASO in a subject comprising administering to the subject 5 mg or 10 mg of lemborexant or an equivalent dose of a pharmaceutically acceptable salt thereof.

In some embodiments, the sWASO is reduced for at least one month. In some embodiments, the sWASO is reduced for at least two months. In some embodiments, the sWASO is reduced for at least three months. In some embodiments, the sWASO is reduced for at least 6 months. In some embodiments, the sWASO is reduced for at least 9 months. In some embodiments, the sWASO is reduced for at least 12 months. In some embodiments, the sWASO is reduced for at least 18 months. In some embodiments, the sWASO is reduced for 2 years or more.

In some embodiments, the sWASO is reduced for at least one month, relative to baseline. In some embodiments, the sWASO is reduced for at least two months, relative to baseline. In some embodiments, the sWASO is reduced for at least three months, relative to baseline. In some embodiments, the sWASO is reduced for at least 6 months, relative to baseline. In some embodiments, the sWASO is reduced for at least 9 months, relative to baseline. In some embodiments, the sWASO is reduced for at least 12 months, relative to baseline. In some embodiments, the sWASO is reduced for at least 18 months, relative to baseline. In some embodiments, the sWASO is reduced for 2 years or more, relative to baseline.

In some embodiments, lemborexant or salt thereof is administered to the subject for at least one month. In some embodiments, lemborexant or salt thereof is administered to the subject for at least two months. In some embodiments, lemborexant or salt thereof is administered to the subject for at least three months. In some embodiments, lemborexant or salt thereof is administered to the subject for at least 6 months. In some embodiments, lemborexant or salt thereof is administered to the subject for at least 9 months. In some embodiments, lemborexant or salt thereof is administered to the subject for at least 12 months. In some embodiments, lemborexant or salt thereof is administered to the subject for at least 18 months. In some embodiments, lemborexant or salt thereof is administered to the subject for two years or more.

In some embodiments, the sWASO is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to baseline. In some embodiments, the sWASO is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 31 minutes, at least 32 minutes, at least 33 minutes, at least 34 minutes, at least 35 minutes, at least 36 minutes, at least 37 minutes, at least 38 minutes, at least 39 minutes, at least 40 minutes, at least 41 minutes, at least 42 minutes, at least 43 minutes, at least 44 minutes, at least 45 minutes, at least 46 minutes, at least 47 minutes, at least 48 minutes, at least 49 minutes, at least 50 minutes, at least 51 minutes, at least 52 minutes, at least 53 minutes, at least 54 minutes, at least 55 minutes, at least 56 minutes, at least 57 minutes, at least 58 minutes, at least 59 minutes, or at least 60, relative to baseline.

In some embodiments, the sWASO is reduced by at least 1 minute, relative to baseline. In some embodiments, the sWASO is reduced by at least 2 minutes, relative to baseline. In some embodiments, the sWASO is reduced by at least 3 minutes, relative to baseline. In some embodiments, the sWASO is reduced by at least 4 minutes, relative to baseline. In some embodiments, the sWASO is reduced by at least 5 minutes, relative to baseline. In some embodiments, the sWASO is reduced by at least 6 minutes, relative to baseline. In some embodiments, the sWASO is reduced by at least 7 minutes, relative to baseline. In some embodiments, the sWASO is reduced by at least 8 minutes, relative to baseline. In some embodiments, the sWASO is reduced by at least 9 minutes, relative to baseline. In some embodiments, the sWASO is reduced by at least 9 minutes, relative to baseline.

In some embodiments, the sWASO is reduced by at least 11 minutes, relative to baseline. In some embodiments, the sWASO is reduced by at least 12 minutes, relative to baseline. In some embodiments, the sWASO is reduced by at least 13 minutes, relative to baseline. In some embodiments, the sWASO is reduced by at least 14 minutes, relative to baseline. In some embodiments, the sWASO is reduced by at least 15 minutes, relative to baseline. In some embodiments, the sWASO is reduced by at least 16 minutes, relative to baseline. In some embodiments, the sWASO is reduced by at least 17 minutes, relative to baseline. In some embodiments, the sWASO is reduced by at least 18 minutes, relative to baseline. In some embodiments, the sWASO is reduced by at least 19 minutes, relative to baseline. In some embodiments, the sWASO is reduced by at least 20 minutes, relative to baseline.

In some embodiments, the sWASO is reduced by at least 21 minutes, relative to baseline. In some embodiments, the sWASO is reduced by at least 22 minutes, relative to baseline. In some embodiments, the sWASO is reduced by at least 23 minutes, relative to baseline. In some embodiments, the sWASO is reduced by at least 24 minutes, relative to baseline. In some embodiments, the sWASO is reduced by at least 25 minutes, relative to baseline. In some embodiments, the sWASO is reduced by at least 26 minutes, relative to baseline. In some embodiments, the sWASO is reduced by at least 27 minutes, relative to baseline. In some embodiments, the sWASO is reduced by at least 28 minutes, relative to baseline. In some embodiments, the sWASO is reduced by at least 29 minutes, relative to baseline.

In some embodiments, the sWASO is reduced by at least 30 minutes, relative to baseline. In some embodiments, the sWASO is reduced by at least 31 minutes, relative to baseline. In some embodiments, the sWASO is reduced by at least 32 minutes, relative to baseline. In some embodiments, the sWASO is reduced by at least 33 minutes, relative to baseline. In some embodiments, the sWASO is reduced by at least 34 minutes, relative to baseline. In some embodiments, the sWASO is reduced by at least 35 minutes, relative to baseline. In some embodiments, the sWASO is reduced by at least 36 minutes, relative to baseline. In some embodiments, the sWASO is reduced by at least 37 minutes, relative to baseline. In some embodiments, the sWASO is reduced by at least 38 minutes, relative to baseline. In some embodiments, the sWASO is reduced by at least 39 minutes, relative to baseline. In some embodiments, the sWASO is reduced by at least 40 minutes, relative to baseline.

In some embodiments, the sWASO is reduced by at least 41 minutes, relative to baseline. In some embodiments, the sWASO is reduced by at least 42 minutes, relative to baseline. In some embodiments, the sWASO is reduced by at least 43 minutes, relative to baseline. In some embodiments, the sWASO is reduced by at least 44 minutes, relative to baseline. In some embodiments, the sWASO is reduced by at least 45 minutes, relative to baseline. In some embodiments, the sWASO is reduced by at least 46 minutes, relative to baseline. In some embodiments, the sWASO is reduced by at least 47 minutes, relative to baseline. In some embodiments, the sWASO is reduced by at least 48 minutes, relative to baseline. In some embodiments, the sWASO is reduced by at least 49 minutes, relative to baseline. In some embodiments, the sWASO is reduced by at least 50 minutes, relative to baseline. In some embodiments, the sWASO is reduced by at least 51 minutes, relative to baseline.

In some embodiments, the sWASO is reduced by at least 52 minutes, relative to baseline. In some embodiments, the sWASO is reduced by at least 53 minutes, relative to baseline. In some embodiments, the sWASO is reduced by at least 54 minutes, relative to baseline. In some embodiments, the sWASO is reduced by at least 55 minutes, relative to baseline. In some embodiments, the sWASO is reduced by at least 56 minutes, relative to baseline. In some embodiments, the sWASO is reduced by at least 57 minutes, relative to baseline. In some embodiments, the sWASO is reduced by at least 58 minutes, relative to baseline. In some embodiments, the sWASO is reduced by at least 59 minutes, relative to baseline. In some embodiments, the sWASO is reduced by at least 60 minutes, relative to baseline.

In some embodiments, the sWASO is reduced by about 1 minute, relative to baseline. In some embodiments, the sWASO is reduced by about 2 minutes, relative to baseline. In some embodiments, the sWASO is reduced by about 3 minutes, relative to baseline. In some embodiments, the sWASO is reduced by about 4 minutes, relative to baseline. In some embodiments, the sWASO is reduced by about 5 minutes, relative to baseline. In some embodiments, the sWASO is reduced by about 6 minutes, relative to baseline. In some embodiments, the sWASO is reduced by about 7 minutes, relative to baseline. In some embodiments, the sWASO is reduced by about 8 minutes, relative to baseline. In some embodiments, the sWASO is reduced by about 9 minutes, relative to baseline. In some embodiments, the sWASO is reduced by about 9 minutes, relative to baseline.

In some embodiments, the sWASO is reduced by about 11 minutes, relative to baseline. In some embodiments, the sWASO is reduced by about 12 minutes, relative to baseline. In some embodiments, the sWASO is reduced by about 13 minutes, relative to baseline. In some embodiments, the sWASO is reduced by about 14 minutes, relative to baseline. In some embodiments, the sWASO is reduced by about 15 minutes, relative to baseline. In some embodiments, the sWASO is reduced by about 16 minutes, relative to baseline. In some embodiments, the sWASO is reduced by about 17 minutes, relative to baseline. In some embodiments, the sWASO is reduced by about 18 minutes, relative to baseline. In some embodiments, the sWASO is reduced by about 19 minutes, relative to baseline. In some embodiments, the sWASO is reduced by about 20 minutes, relative to baseline.

In some embodiments, the sWASO is reduced by about 21 minutes, relative to baseline. In some embodiments, the sWASO is reduced by about 22 minutes, relative to baseline. In some embodiments, the sWASO is reduced by about 23 minutes, relative to baseline. In some embodiments, the sWASO is reduced by about 24 minutes, relative to baseline. In some embodiments, the sWASO is reduced by about 25 minutes, relative to baseline. In some embodiments, the sWASO is reduced by about 26 minutes, relative to baseline. In some embodiments, the sWASO is reduced by about 27 minutes, relative to baseline. In some embodiments, the sWASO is reduced by about 28 minutes, relative to baseline. In some embodiments, the sWASO is reduced by about 29 minutes, relative to baseline.

In some embodiments, the sWASO is reduced by about 30 minutes, relative to baseline. In some embodiments, the sWASO is reduced by about 31 minutes, relative to baseline. In some embodiments, the sWASO is reduced by about 32 minutes, relative to baseline. In some embodiments, the sWASO is reduced by about 33 minutes, relative to baseline. In some embodiments, the sWASO is reduced by about 34 minutes, relative to baseline. In some embodiments, the sWASO is reduced by about 35 minutes, relative to baseline. In some embodiments, the sWASO is reduced by about 36 minutes, relative to baseline. In some embodiments, the sWASO is reduced by about 37 minutes, relative to baseline.

In some embodiments, the sWASO is reduced by about 38 minutes, relative to baseline. In some embodiments, the sWASO is reduced by about 39 minutes, relative to baseline. In some embodiments, the sWASO is reduced by about 40 minutes, relative to baseline.

In some embodiments, the sWASO is reduced by about 41 minutes, relative to baseline. In some embodiments, the sWASO is reduced by about 42 minutes, relative to baseline. In some embodiments, the sWASO is reduced by about 43 minutes, relative to baseline. In some embodiments, the sWASO is reduced by about 44 minutes, relative to baseline. In some embodiments, the sWASO is reduced by about 45 minutes, relative to baseline. In some embodiments, the sWASO is reduced by about 46 minutes, relative to baseline. In some embodiments, the sWASO is reduced by about 47 minutes, relative to baseline. In some embodiments, the sWASO is reduced by about 48 minutes, relative to baseline. In some embodiments, the sWASO is reduced by about 49 minutes, relative to baseline. In some embodiments, the sWASO is reduced by about 50 minutes, relative to baseline. In some embodiments, the sWASO is reduced by about 51 minutes, relative to baseline.

In some embodiments, the sWASO is reduced by about 52 minutes, relative to baseline. In some embodiments, the sWASO is reduced by about 53 minutes, relative to baseline. In some embodiments, the sWASO is reduced by about 54 minutes, relative to baseline. In some embodiments, the sWASO is reduced by about 55 minutes, relative to baseline. In some embodiments, the sWASO is reduced by about 56 minutes, relative to baseline. In some embodiments, the sWASO is reduced by about 57 minutes, relative to baseline. In some embodiments, the sWASO is reduced by about 58 minutes, relative to baseline. In some embodiments, the sWASO is reduced by about 59 minutes, relative to baseline. In some embodiments, the sWASO is reduced by about 60 minutes, relative to baseline.

In some embodiments, 5 mg of lemborexant or an equivalent dose of a pharmaceutically acceptable salt thereof is administered to a subject and the sWASO is reduced by about 20 minutes, relative to baseline. In some embodiments, 5 mg of lemborexant or an equivalent dose of a pharmaceutically acceptable salt thereof is administered to a subject and the sWASO is reduced by about 25 minutes, relative to baseline. In some embodiments, 5 mg of lemborexant or an equivalent dose of a pharmaceutically acceptable salt thereof is administered to a subject and the sWASO is reduced by about 45 minutes, relative to baseline. In some embodiments, 5 mg of lemborexant or an equivalent dose of a pharmaceutically acceptable salt thereof is administered to a subject and the sWASO is reduced by about 55 minutes, relative to baseline.

In some embodiments, 5 mg of lemborexant or an equivalent dose of a pharmaceutically acceptable salt thereof is administered to a subject and the sWASO is reduced by at least 20 minutes, relative to baseline. In some embodiments, 5 mg of lemborexant or an equivalent dose of a pharmaceutically acceptable salt thereof is administered to a subject and the sWASO is reduced by at least 23 minutes, relative to baseline. In some embodiments, 5 mg of lemborexant or an equivalent dose of a pharmaceutically acceptable salt thereof is administered to a subject and the sWASO is reduced by at least 42 minutes, relative to baseline. In some embodiments, 5 mg of lemborexant or an equivalent dose of a pharmaceutically acceptable salt thereof is administered to a subject and the sWASO is reduced by at least 51 minutes, relative to baseline.

In some embodiments, 10 mg of lemborexant or an equivalent dose of a pharmaceutically acceptable salt thereof is administered to a subject and the sWASO is reduced by about 25 minutes, relative to baseline. In some embodiments, 10 mg of lemborexant or an equivalent dose of a pharmaceutically acceptable salt thereof is administered to a subject and the sWASO is reduced by about 30 minutes, relative to baseline. In some embodiments, 10 mg of lemborexant or an equivalent dose of a pharmaceutically acceptable salt thereof is administered to a subject and the sWASO is reduced by about 40 minutes, relative to baseline. In some embodiments, 10 mg of lemborexant or an equivalent dose of a pharmaceutically acceptable salt thereof is administered to a subject and the sWASO is reduced by about 50 minutes, relative to baseline.

In some embodiments, 10 mg of lemborexant or an equivalent dose of a pharmaceutically acceptable salt thereof is administered to a subject and the sWASO is reduced by at least 23 minutes, relative to baseline. In some embodiments, 10 mg of lemborexant or an equivalent dose of a pharmaceutically acceptable salt thereof is administered to a subject and the sWASO is reduced by at least 26 minutes, relative to baseline. In some embodiments, 10 mg of lemborexant or an equivalent dose of a pharmaceutically acceptable salt thereof is administered to a subject and the sWASO is reduced by at least 39 minutes, relative to baseline. In some embodiments, 10 mg of lemborexant or an equivalent dose of a pharmaceutically acceptable salt thereof is administered to a subject and the sWASO is reduced by at least 48 minutes, relative to baseline.

In some embodiments, the sWASO is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to placebo. In some embodiments, the sWASO is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, or at least 30 minutes, relative to placebo.

In some embodiments, the sWASO is reduced by at least 1 minute, relative to placebo. In some embodiments, the sWASO is reduced by at least 2 minutes, relative to placebo. In some embodiments, the sWASO is reduced by at least 3 minutes, relative to placebo. In some embodiments, the sWASO is reduced by at least 4 minutes, relative to placebo. In some embodiments, the sWASO is reduced by at least 5 minutes, relative to placebo. In some embodiments, the sWASO is reduced by at least 6 minutes, relative to placebo. In some embodiments, the sWASO is reduced by at least 7 minutes, relative to placebo. In some embodiments, the sWASO is reduced by at least 8 minutes, relative to placebo. In some embodiments, the sWASO is reduced by at least 9 minutes, relative to placebo. In some embodiments, the sWASO is reduced by at least 10 minutes, relative to placebo.

In some embodiments, the sWASO is reduced by at least 11 minutes, relative to placebo. In some embodiments, the sWASO is reduced by at least 12 minutes, relative to placebo. In some embodiments, the sWASO is reduced by at least 13 minutes, relative to placebo. In some embodiments, the sWASO is reduced by at least 14 minutes, relative to placebo. In some embodiments, the sWASO is reduced by at least 15 minutes, relative to placebo. In some embodiments, the sWASO is reduced by at least 16 minutes, relative to placebo. In some embodiments, the sWASO is reduced by at least 17 minutes, relative to placebo. In some embodiments, the sWASO is reduced by at least 18 minutes, relative to placebo. In some embodiments, the sWASO is reduced by at least 19 minutes, relative to placebo. In some embodiments, the sWASO is reduced by at least 20 minutes, relative to placebo.

In some embodiments, the sWASO is reduced by at least 21 minutes, relative to placebo. In some embodiments, the sWASO is reduced by at least 22 minutes, relative to placebo. In some embodiments, the sWASO is reduced by at least 23 minutes, relative to placebo. In some embodiments, the sWASO is reduced by at least 24 minutes, relative to placebo. In some embodiments, the sWASO is reduced by at least 25 minutes, relative to placebo. In some embodiments, the sWASO is reduced by at least 26 minutes, relative to placebo. In some embodiments, the sWASO is reduced by at least 27 minutes, relative to placebo. In some embodiments, the sWASO is reduced by at least 28 minutes, relative to placebo. In some embodiments, the sWASO is reduced by at least 29 minutes, relative to placebo. In some embodiments, the sWASO is reduced by at least 30 minutes, relative to placebo.

In some embodiments, the sWASO is reduced by about 1 minute, relative to placebo. In some embodiments, the sWASO is reduced by about 2 minutes, relative to placebo. In some embodiments, the sWASO is reduced by about 3 minutes, relative to placebo. In some embodiments, the sWASO is reduced by about 4 minutes, relative to placebo. In some embodiments, the sWASO is reduced by about 5 minutes, relative to placebo. In some embodiments, the sWASO is reduced by about 6 minutes, relative to placebo. In some embodiments, the sWASO is reduced by about 7 minutes, relative to placebo. In some embodiments, the sWASO is reduced by about 8 minutes, relative to baseline. In some embodiments, the sWASO is reduced by about 9 minutes, relative to baseline. In some embodiments, the sWASO is reduced by about 10 minutes, relative to placebo.

In some embodiments, the sWASO is reduced by about 11 minutes, relative to placebo. In some embodiments, the sWASO is reduced by about 12 minutes, relative to placebo. In some embodiments, the sWASO is reduced by about 13 minutes, relative to placebo. In some embodiments, the sWASO is reduced by about 14 minutes, relative to placebo. In some embodiments, the sWASO is reduced by about 15 minutes, relative to placebo. In some embodiments, the sWASO is reduced by about 16 minutes, relative to placebo. In some embodiments, the sWASO is reduced by about 17 minutes, relative to placebo. In some embodiments, the sWASO is reduced by about 18 minutes, relative to placebo. In some embodiments, the sWASO is reduced by about 19 minutes, relative to placebo. In some embodiments, the sWASO is reduced by about 20 minutes, relative to placebo.

In some embodiments, the sWASO is reduced by about 21 minutes, relative to placebo. In some embodiments, the sWASO is reduced by about 22 minutes, relative to placebo. In some embodiments, the sWASO is reduced by about 23 minutes, relative to placebo. In some embodiments, the sWASO is reduced by about 24 minutes, relative to placebo. In some embodiments, the sWASO is reduced by about 25 minutes, relative to placebo. In some embodiments, the sWASO is reduced by about 26 minutes, relative to placebo. In some embodiments, the sWASO is reduced by about 27 minutes, relative to placebo. In some embodiments, the sWASO is reduced by about 28 minutes, relative to placebo. In some embodiments, the sWASO is reduced by about 29 minutes, relative to placebo. In some embodiments, the sWASO is reduced by about 30 minutes, relative to placebo.

In some embodiments, 5 mg of lemborexant or an equivalent dose of a pharmaceutically acceptable salt thereof is administered to a subject and the sWASO is reduced by about 5 minutes, relative to placebo. In some embodiments, 5 mg of lemborexant or an equivalent dose of a pharmaceutically acceptable salt thereof is administered to a subject and the sWASO is reduced by about 15 minutes, relative to placebo. In some embodiments, 5 mg of lemborexant or an equivalent dose of a pharmaceutically acceptable salt thereof is administered to a subject and the sWASO is reduced by about 20 minutes, relative to placebo.

In some embodiments, 5 mg of lemborexant or an equivalent dose of a pharmaceutically acceptable salt thereof is administered to a subject and the sWASO is reduced by at least 5 minutes, relative to placebo. In some embodiments, 5 mg of lemborexant or an equivalent dose of a pharmaceutically acceptable salt thereof is administered to a subject and the sWASO is reduced by at least 13 minutes, relative to placebo. In some embodiments, 5 mg of lemborexant or an equivalent dose of a pharmaceutically acceptable salt thereof is administered to a subject and the sWASO is reduced by at least 14 minutes, relative to placebo. In some embodiments, 5 mg of lemborexant or an equivalent dose of a pharmaceutically acceptable salt thereof is administered to a subject and the sWASO is reduced by at least 17 minutes, relative to placebo.

In some embodiments, 10 mg of lemborexant or an equivalent dose of a pharmaceutically acceptable salt thereof is administered to a subject and the sWASO is reduced by about 5 minutes, relative to placebo. In some embodiments, 10 mg of lemborexant or an equivalent dose of a pharmaceutically acceptable salt thereof is administered to a subject and the sWASO is reduced by about 10 minutes, relative to placebo. In some embodiments, 10 mg of lemborexant or an equivalent dose of a pharmaceutically acceptable salt thereof is administered to a subject and the sWASO is reduced by about 15 minutes, relative to placebo.

In some embodiments, 10 mg of lemborexant or an equivalent dose of a pharmaceutically acceptable salt thereof is administered to a subject and the sWASO is reduced by at least 7 minutes, relative to placebo. In some embodiments, 10 mg of lemborexant or an equivalent dose of a pharmaceutically acceptable salt thereof is administered to a subject and the sWASO is reduced by at least 10 minutes, relative to placebo. In some embodiments, 10 mg of lemborexant or an equivalent dose of a pharmaceutically acceptable salt thereof is administered to a subject and the sWASO is reduced by at least 12 minutes, relative to placebo. In some embodiments, 10 mg of lemborexant or an equivalent dose of a pharmaceutically acceptable salt thereof is administered to a subject and the sWASO is reduced by at least 16 minutes, relative to placebo.

In some embodiments, the subject has insomnia.

Methods of Improving Subjective Sleep Efficiency (sSE)

Provided herein is a method of improving subjective sleep efficiency (sSE) in a subject comprising administering to the subject 5 mg or 10 mg of lemborexant or an equivalent dose of a pharmaceutically acceptable salt thereof. Also disclosed herein is lemborexant or a pharmaceutically acceptable salt thereof for use in improving sSE in a subject comprising administering to the subject 5 mg or 10 mg of lemborexant or an equivalent dose of a pharmaceutically acceptable salt thereof.

In some embodiments, the sSE is improved for at least one month. In some embodiments, the sSE is improved for at least two months. In some embodiments, the sSE is improved for at least three months. In some embodiments, the sSE is improved for at least 6 months. In some embodiments, the sSE is improved for at least 9 months. In some embodiments, the sSE is improved for at least 12 months. In some embodiments, the sSE is improved for at least 18 months. In some embodiments, the sSE is improved for 2 years or more.

In some embodiments, the sSE is improved for at least one month, relative to baseline. In some embodiments, the sSE is improved for at least two months, relative to baseline. In some embodiments, the sSE is improved for at least three months, relative to baseline. In some embodiments, the sSE is improved for at least 6 months, relative to baseline. In some embodiments, the sSE is improved for at least 9 months, relative to baseline. In some embodiments, the sSE is improved for at least 12 months, relative to baseline. In some embodiments, the sSE is improved for at least 18 months, relative to baseline. In some embodiments, the sSE is improved for 2 years or more, relative to baseline.

In some embodiments, lemborexant or salt thereof is administered to the subject for at least one month. In some embodiments, lemborexant or salt thereof is administered to the subject for at least two months. In some embodiments, lemborexant or salt thereof is administered to the subject for at least three months. In some embodiments, lemborexant or salt thereof is administered to the subject for at least 6 months. In some embodiments, lemborexant or salt thereof is administered to the subject for at least 9 months. In some embodiments, lemborexant or salt thereof is administered to the subject for at least 12 months. In some embodiments, lemborexant or salt thereof is administered to the subject for at least 18 months. In some embodiments, lemborexant or salt thereof is administered to the subject for two years or more.

In some embodiments, the sSE is improved by at least 1%, at least 5%, at least 10%, at least 15%, at least 20%, at least 25%, at least 30%, at least 40%, or at least 50%, relative to baseline. In some embodiments, the sSE is improved by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, or at least 25%, relative to baseline.

In some embodiments, the sSE is improved by at least 1%, relative to baseline. In some embodiments, the sSE is improved by at least 2%, relative to baseline. In some embodiments, the sSE is improved by at least 3%, relative to baseline. In some embodiments, the sSE is improved by at least 4%, relative to baseline. In some embodiments, the sSE is improved by at least 5%, relative to baseline. In some embodiments, the sSE is improved by at least 6%, relative to baseline. In some embodiments, the sSE is improved by at least 7%, relative to baseline. In some embodiments, the sSE is improved by at least 8%, relative to baseline. In some embodiments, the sSE is improved by at least 9%, relative to baseline.

In some embodiments, the sSE is improved by at least 10%, relative to baseline. In some embodiments, the sSE is improved by at least 11%, relative to baseline. In some embodiments, the sSE is improved by at least 12%, relative to baseline. In some embodiments, the sSE is improved by at least 13%, relative to baseline. In some embodiments, the sSE is improved by at least 14%, relative to baseline. In some embodiments, the sSE is improved by at least 15%, relative to baseline. In some embodiments, the sSE is improved by at least 16%, relative to baseline. In some embodiments, the sSE is improved by at least 17%, relative to baseline. In some embodiments, the sSE is improved by at least 18%, relative to baseline. In some embodiments, the sSE is improved by at least 19%, relative to baseline.

In some embodiments, the sSE is improved by at least 20%, relative to baseline. In some embodiments, the sSE is improved by at least 21%, relative to baseline. In some embodiments, the sSE is improved by at least 22%, relative to baseline. In some embodiments, the sSE is improved by at least 23%, relative to baseline. In some embodiments, the sSE is improved by at least 24%, relative to baseline. In some embodiments, the sSE is improved by at least 25%, relative to baseline.

In some embodiments, the sSE is improved by about 1%, relative to baseline. In some embodiments, the sSE is improved by about 2%, relative to baseline. In some embodiments, the sSE is improved by about 3%, relative to baseline. In some embodiments, the sSE is improved by about 4%, relative to baseline. In some embodiments, the sSE is improved by about 5%, relative to baseline. In some embodiments, the sSE is improved by about 6%, relative to baseline. In some embodiments, the sSE is improved by about 7%, relative to baseline. In some embodiments, the sSE is improved by about 8%, relative to baseline. In some embodiments, the sSE is improved by about 9%, relative to baseline.

In some embodiments, the sSE is improved by about 10%, relative to baseline. In some embodiments, the sSE is improved by about 11%, relative to baseline. In some embodiments, the sSE is improved by about 12%, relative to baseline. In some embodiments, the sSE is improved by about 13%, relative to baseline. In some embodiments, the sSE is improved by about 14%, relative to baseline. In some embodiments, the sSE is improved by about 15%, relative to baseline. In some embodiments, the sSE is improved by about 16%, relative to baseline. In some embodiments, the sSE is improved by about 17%, relative to baseline. In some embodiments, the sSE is improved by about 18%, relative to baseline. In some embodiments, the sSE is improved by about 19%, relative to baseline.

In some embodiments, the sSE is improved by about 20%, relative to baseline. In some embodiments, the sSE is improved by about 21%, relative to baseline. In some embodiments, the sSE is improved by about 22%, relative to baseline. In some embodiments, the sSE is improved by about 23%, relative to baseline. In some embodiments, the sSE is improved by about 24%, relative to baseline. In some embodiments, the sSE is improved by about 25%, relative to baseline.

In some embodiments, 5 mg of lemborexant or an equivalent dose of a pharmaceutically acceptable salt thereof is administered to a subject and the sSE is improved by at least 6%, relative to baseline. In some embodiments, 5 mg of lemborexant or an equivalent dose of a pharmaceutically acceptable salt thereof is administered to a subject and the sSE is improved by at least 7%, relative to baseline. In some embodiments, 5 mg of lemborexant or an equivalent dose of a pharmaceutically acceptable salt thereof is administered to a subject and the sSE is improved by at least 13%, relative to baseline. In some embodiments, 5 mg of lemborexant or an equivalent dose of a pharmaceutically acceptable salt thereof is administered to a subject and the sSE is improved by at least 15%, relative to baseline.

In some embodiments, 5 mg of lemborexant or an equivalent dose of a pharmaceutically acceptable salt thereof is administered to a subject and the sSE is improved by about 6%, relative to baseline. In some embodiments, 5 mg of lemborexant or an equivalent dose of a pharmaceutically acceptable salt thereof is administered to a subject and the sSE is improved by about 7%, relative to baseline. In some embodiments, 5 mg of lemborexant or an equivalent dose of a pharmaceutically acceptable salt thereof is administered to a subject and the sSE is improved by about 13%, relative to baseline. In some embodiments, 5 mg of lemborexant or an equivalent dose of a pharmaceutically acceptable salt thereof is administered to a subject and the sSE is improved by about 15%, relative to baseline.

In some embodiments, 10 mg of lemborexant or an equivalent dose of a pharmaceutically acceptable salt thereof is administered to a subject and the sSE is improved by at least 8%, relative to baseline. In some embodiments, 10 mg of lemborexant or an equivalent dose of a pharmaceutically acceptable salt thereof is administered to a subject and the sSE is improved by at least 9%, relative to baseline. In some embodiments, 10 mg of lemborexant or an equivalent dose of a pharmaceutically acceptable salt thereof is administered to a subject and the sSE is improved by at least 13%, relative to baseline. In some embodiments, 10 mg of lemborexant or an equivalent dose of a pharmaceutically acceptable salt thereof is administered to a subject and the sSE is improved by at least 15%, relative to baseline.

In some embodiments, 10 mg of lemborexant or an equivalent dose of a pharmaceutically acceptable salt thereof is administered to a subject and the sSE is improved by about 8%, relative to baseline. In some embodiments, 10 mg of lemborexant or an equivalent dose of a pharmaceutically acceptable salt thereof is administered to a subject and the sSE is improved by about 9%, relative to baseline. In some embodiments, 10 mg of lemborexant or an equivalent dose of a pharmaceutically acceptable salt thereof is administered to a subject and the sSE is improved by about 13%, relative to baseline. In some embodiments, 10 mg of lemborexant or an equivalent dose of a pharmaceutically acceptable salt thereof is administered to a subject and the sSE is improved by about 15%, relative to baseline.

In some embodiments, the sSE is improved by at least 1%, at least 5%, at least 10%, at least 15%, at least 20%, at least 25%, at least 30%, at least 40%, or at least 50%, relative to placebo. In some embodiments, the sSE is improved by at least 1%, at least 2%, at least 3%, at least 4%, at least 5%, at least 6%, at least 7%, at least 8%, at least 9%, or at least 10%, relative to placebo.

In some embodiments, the sSE is improved by at least 1%, relative to placebo. In some embodiments, the sSE is improved by at least 2%, relative to placebo. In some embodiments, the sSE is improved by at least 3%, relative to placebo. In some embodiments, the sSE is improved by at least 4%, relative to placebo. In some embodiments, the sSE is improved by at least 5%, relative to placebo.

In some embodiments, the sSE is improved by at least 6%, relative to placebo. In some embodiments, the sSE is improved by at least 7%, relative to placebo. In some embodiments, the sSE is improved by at least 8%, relative to placebo. In some embodiments, the sSE is improved by at least 9%, relative to placebo. In some embodiments, the sSE is improved by at least 10%, relative to placebo.

In some embodiments, the sSE is improved by about 1%, relative to placebo. In some embodiments, the sSE is improved by about 2%, relative to placebo. In some embodiments, the sSE is improved by about 3%, relative to placebo. In some embodiments, the sSE is improved by about 4%, relative to placebo. In some embodiments, the sSE is improved by about 5%, relative to placebo.

In some embodiments, the sSE is improved by about 6%, relative to placebo. In some embodiments, the sSE is improved by about 7%, relative to placebo. In some embodiments, the sSE is improved by about 8%, relative to placebo. In some embodiments, the sSE is improved by about 9%, relative to placebo. In some embodiments, the sSE is improved by about 10%, relative to placebo.

In some embodiments, 5 mg of lemborexant or an equivalent dose of a pharmaceutically acceptable salt thereof is administered to a subject and the sSE is improved by at least 2%, relative to placebo. In some embodiments, 5 mg of lemborexant or an equivalent dose of a pharmaceutically acceptable salt thereof is administered to a subject and the sSE is improved by at least 4%, relative to placebo.

In some embodiments, 5 mg of lemborexant or an equivalent dose of a pharmaceutically acceptable salt thereof is administered to a subject and the sSE is improved by at least 2%, relative to baseline. In some embodiments, 5 mg of lemborexant or an equivalent dose of a pharmaceutically acceptable salt thereof is administered to a subject and the sSE is improved by at least 4%, relative to baseline.

In some embodiments, 10 mg of lemborexant or an equivalent dose of a pharmaceutically acceptable salt thereof is administered to a subject and the sSE is improved by at least 3%, relative to placebo. In some embodiments, 10 mg of lemborexant or an equivalent dose of a pharmaceutically acceptable salt thereof is administered to a subject and the sSE is improved by at least 4%, relative to placebo. In some embodiments, 10 mg of lemborexant or an equivalent dose of a pharmaceutically acceptable salt thereof is administered to a subject and the sSE is improved by at least 5%, relative to placebo.

In some embodiments, 10 mg of lemborexant or an equivalent dose of a pharmaceutically acceptable salt thereof is administered to a subject and the sSE is improved by at least 3%, relative to placebo. In some embodiments, 10 mg of lemborexant or an equivalent dose of a pharmaceutically acceptable salt thereof is administered to a subject and the sSE is improved by at least 4%, relative to placebo. In some embodiments, 10 mg of lemborexant or an equivalent dose of a pharmaceutically acceptable salt thereof is administered to a subject and the sSE is improved by at least 5%, relative to placebo.

Methods of Reducing Latency to Persistent Sleep (LPS)

Provided herein is a method of reducing latency to persistent sleep (LPS) in a subject comprising administering to the subject 5 mg or 10 mg of lemborexant or an equivalent dose of a pharmaceutically acceptable salt thereof. Also disclosed herein is lemborexant or a pharmaceutically acceptable salt thereof for use in reducing LPS in a subject comprising administering to the subject 5 mg or 10 mg of lemborexant or an equivalent dose of a pharmaceutically acceptable salt thereof.

In some embodiments, the LPS is reduced for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days. In some embodiments, the LPS is reduced for at least 1 day. In some embodiments, the LPS is reduced for at least 2 days. In some embodiments, the LPS is reduced for at least 3 days. In some embodiments, the LPS is reduced for at least 4 days. In some embodiments, the LPS is reduced for at least 5 days. In some embodiments, the LPS is reduced for at least 6 days. In some embodiments, the LPS is reduced for at least 7 days. In some embodiments, the LPS is reduced for at least 8 days. In some embodiments, the LPS is reduced for at least 9 days. In some embodiments, the LPS is reduced for at least 10 days.

In some embodiments, the LPS is reduced for at least 11 days. In some embodiments, the LPS is reduced for at least 12 days. In some embodiments, the LPS is reduced for at least 13 days. In some embodiments, the LPS is reduced for at least 14 days. In some embodiments, the LPS is reduced for at least 15 days. In some embodiments, the LPS is reduced for at least 16 days. In some embodiments, the LPS is reduced for at least 17 days. In some embodiments, the LPS is reduced for at least 18 days. In some embodiments, the LPS is reduced for at least 19 days.

In some embodiments, the LPS is reduced for at least 20 days. In some embodiments, the LPS is reduced for at least 21 days. In some embodiments, the LPS is reduced for at least 22 days. In some embodiments, the LPS is reduced for at least 23 days. In some embodiments, the LPS is reduced for at least 24 days. In some embodiments, the LPS is reduced for at least 25 days. In some embodiments, the LPS is reduced for at least 26 days. In some embodiments, the LPS is reduced for at least 27 days. In some embodiments, the LPS is reduced for at least 28 days. In some embodiments, the LPS is reduced for at least 29 days. In some embodiments, the LPS is reduced for at least 30 days.

In some embodiments, the LPS is reduced for at least one month. In some embodiments, the LPS is reduced for at least two months. In some embodiments, the LPS is reduced for at least three months. In some embodiments, the LPS is reduced for at least 6 months. In some embodiments, the LPS is reduced for at least 9 months. In some embodiments, the LPS is reduced for at least 12 months. In some embodiments, the LPS is reduced for at least 18 months. In some embodiments, the LPS is reduced for 2 years or more.

In some embodiments, the LPS is reduced for at least one month. In some embodiments, the LPS is reduced for at least two months, relative to baseline. In some embodiments, the LPS is reduced for at least three months, relative to baseline. In some embodiments, the LPS is reduced for at least 6 months, relative to baseline. In some embodiments, the LPS is reduced for at least 9 months, relative to baseline. In some embodiments, the LPS is reduced for at least 12 months, relative to baseline. In some embodiments, the LPS is reduced for at least 18 months, relative to baseline. In some embodiments, the LPS is reduced for 2 years or more, relative to baseline.

In some embodiments, lemborexant or salt thereof is administered to the subject for at least one month. In some embodiments, lemborexant or salt thereof is administered to the subject for at least two months. In some embodiments, lemborexant or salt thereof is administered to the subject for at least three months. In some embodiments, lemborexant or salt thereof is administered to the subject for at least 6 months. In some embodiments, lemborexant or salt thereof is administered to the subject for at least 9 months. In some embodiments, lemborexant or salt thereof is administered to the subject for at least 12 months. In some embodiments, lemborexant or salt thereof is administered to the subject for at least 18 months. In some embodiments, lemborexant or salt thereof is administered to the subject for two years or more.

In some embodiments, the LPS is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to baseline. In some embodiments, the LPS is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 31 minutes, at least 32 minutes, at least 33 minutes, at least 34 minutes, at least 35 minutes, at least 36 minutes, at least 37 minutes, at least 38 minutes, at least 39 minutes, at least 40 minutes, at least 41 minutes, at least 42 minutes, at least 43 minutes, at least 44 minutes, or at least 45 minutes, relative to baseline.

In some embodiments, the LPS is reduced by at least 1 minute, relative to baseline. In some embodiments, the LPS is reduced by at least 2 minutes, relative to baseline. In some embodiments, the LPS is reduced by at least 3 minutes, relative to baseline. In some embodiments, the LPS is reduced by at least 4 minutes, relative to baseline. In some embodiments, the LPS is reduced by at least 5 minutes, relative to baseline. In some embodiments, the LPS is reduced by at least 6 minutes, relative to baseline. In some embodiments, the LPS is reduced by at least 7 minutes, relative to baseline. In some embodiments, the LPS is reduced by at least 8 minutes, relative to baseline. In some embodiments, the LPS is reduced by at least 9 minutes, relative to baseline. In some embodiments, the LPS is reduced by at least 10 minutes, relative to baseline.

In some embodiments, the LPS is reduced by at least 11 minutes, relative to baseline. In some embodiments, the LPS is reduced by at least 12 minutes, relative to baseline. In some embodiments, the LPS is reduced by at least 13 minutes, relative to baseline. In some embodiments, the LPS is reduced by at least 14 minutes, relative to baseline. In some embodiments, the LPS is reduced by at least 15 minutes, relative to baseline. In some embodiments, the LPS is reduced by at least 16 minutes, relative to baseline. In some embodiments, the LPS is reduced by at least 17 minutes, relative to baseline. In some embodiments, the LPS is reduced by at least 18 minutes, relative to baseline. In some embodiments, the LPS is reduced by at least 19 minutes, relative to baseline. In some embodiments, the LPS is reduced by at least 20 minutes, relative to baseline.

In some embodiments, the LPS is reduced by at least 21 minutes, relative to baseline. In some embodiments, the LPS is reduced by at least 22 minutes, relative to baseline. In some embodiments, the LPS is reduced by at least 23 minutes, relative to baseline. In some embodiments, the LPS is reduced by at least 24 minutes, relative to baseline. In some embodiments, the LPS is reduced by at least 25 minutes, relative to baseline. In some embodiments, the LPS is reduced by at least 26 minutes, relative to baseline. In some embodiments, the LPS is reduced by at least 27 minutes, relative to baseline. In some embodiments, the LPS is reduced by at least 28 minutes, relative to baseline. In some embodiments, the LPS is reduced by at least 29 minutes, relative to baseline.

In some embodiments, the LPS is reduced by at least 30 minutes, relative to baseline. In some embodiments, the LPS is reduced by at least 31 minutes, relative to baseline. In some embodiments, the LPS is reduced by at least 32 minutes, relative to baseline. In some embodiments, the LPS is reduced by at least 33 minutes, relative to baseline. In some embodiments, the LPS is reduced by at least 34 minutes, relative to baseline. In some embodiments, the LPS is reduced by at least 35 minutes, relative to baseline. In some embodiments, the LPS is reduced by at least 36 minutes, relative to baseline. In some embodiments, the LPS is reduced by at least 37 minutes, relative to baseline. In some embodiments, the LPS is reduced by at least 38 minutes, relative to baseline. In some embodiments, the LPS is reduced by at least 39 minutes, relative to baseline. In some embodiments, the LPS is reduced by at least 40 minutes, relative to baseline.

In some embodiments, the LPS is reduced by about 1 minute, relative to baseline. In some embodiments, the LPS is reduced by about 2 minutes, relative to baseline. In some embodiments, the LPS is reduced by about 3 minutes, relative to baseline. In some embodiments, the LPS is reduced by about 4 minutes, relative to baseline. In some embodiments, the LPS is reduced by about 5 minutes, relative to baseline. In some embodiments, the LPS is reduced by about 6 minutes, relative to baseline. In some embodiments, the LPS is reduced by about 7 minutes, relative to baseline. In some embodiments, the LPS is reduced by about 8 minutes, relative to baseline. In some embodiments, the LPS is reduced by about 9 minutes, relative to baseline. In some embodiments, the LPS is reduced by about 10 minutes, relative to baseline.

In some embodiments, the LPS is reduced by about 11 minutes, relative to baseline. In some embodiments, the LPS is reduced by about 12 minutes, relative to baseline. In some embodiments, the LPS is reduced by about 13 minutes, relative to baseline. In some embodiments, the LPS is reduced by about 14 minutes, relative to baseline. In some embodiments, the LPS is reduced by about 15 minutes, relative to baseline. In some embodiments, the LPS is reduced by about 16 minutes, relative to baseline. In some embodiments, the LPS is reduced by about 17 minutes, relative to baseline. In some embodiments, the LPS is reduced by about 18 minutes, relative to baseline. In some embodiments, the LPS is reduced by about 19 minutes, relative to baseline. In some embodiments, the LPS is reduced by about 20 minutes, relative to baseline.

In some embodiments, the LPS is reduced by about 21 minutes, relative to baseline. In some embodiments, the LPS is reduced by about 22 minutes, relative to baseline. In some embodiments, the LPS is reduced by about 23 minutes, relative to baseline. In some embodiments, the LPS is reduced by about 24 minutes, relative to baseline. In some embodiments, the LPS is reduced by about 25 minutes, relative to baseline. In some embodiments, the LPS is reduced by about 26 minutes, relative to baseline. In some embodiments, the LPS is reduced by about 27 minutes, relative to baseline. In some embodiments, the LPS is reduced by about 28 minutes, relative to baseline. In some embodiments, the LPS is reduced by about 29 minutes, relative to baseline.

In some embodiments, the LPS is reduced by about 30 minutes, relative to baseline. In some embodiments, the LPS is reduced by about 31 minutes, relative to baseline. In some embodiments, the LPS is reduced by about 32 minutes, relative to baseline. In some embodiments, the LPS is reduced by about 33 minutes, relative to baseline. In some embodiments, the LPS is reduced by about 34 minutes, relative to baseline. In some embodiments, the LPS is reduced by about 35 minutes, relative to baseline. In some embodiments, the LPS is reduced by about 36 minutes, relative to baseline. In some embodiments, the LPS is reduced by about 37 minutes, relative to baseline. In some embodiments, the LPS is reduced by about 38 minutes, relative to baseline. In some embodiments, the LPS is reduced by about 39 minutes, relative to baseline. In some embodiments, the LPS is reduced by about 40 minutes, relative to baseline.

In some embodiments, 5 mg of lemborexant or an equivalent dose of a pharmaceutically acceptable salt thereof is administered to a subject and the LPS is reduced by about 16 minutes. In some embodiments, 5 mg of lemborexant or an equivalent dose of a pharmaceutically acceptable salt thereof is administered to a subject and the LPS is reduced by about 19 minutes.

In some embodiments, 5 mg of lemborexant or an equivalent dose of a pharmaceutically acceptable salt thereof is administered to a subject and the LPS is reduced by at least 16 minutes. In some embodiments, 5 mg of lemborexant or an equivalent dose of a pharmaceutically acceptable salt thereof is administered to a subject and the LPS is reduced by at least 19 minutes.

In some embodiments, 10 mg of lemborexant or an equivalent dose of a pharmaceutically acceptable salt thereof is administered to a subject and the LPS is reduced by about 19 minutes. In some embodiments, 10 mg of lemborexant or an equivalent dose of a pharmaceutically acceptable salt thereof is administered to a subject and the LPS is reduced by about 21 minutes.

In some embodiments, 10 mg of lemborexant or an equivalent dose of a pharmaceutically acceptable salt thereof is administered to a subject and the LPS is reduced by at least 19 minutes. In some embodiments, 10 mg of lemborexant or an equivalent dose of a pharmaceutically acceptable salt thereof is administered to a subject and the LPS is reduced by at least 21 minutes.

In some embodiments, LPS is 1 minute or less, 2 minutes or less, 3 minutes or less, 4 minutes or less, 5 minutes or less, 5 minutes or less, 6 minutes or less, 7 minutes or less, 8 minutes or less, 9 minutes or less, 10 minutes or less, 11 minutes or less, 12 minutes or less, 13 minutes or less, 14 minutes or less, 15 minutes or less, 16 minutes or less, 17 minutes or less, 18 minutes or less, 19 minutes or less, 20 minutes or less, 21 minutes or less, 22 minutes or less, 23 minutes or less, 24 minutes or less, 25 minutes or less, 26 minutes or less, 27 minutes or less, 28 minutes or less, 29 minutes or less, 30 minutes or less, 31 minutes or less, 32 minutes or less, 33 minutes or less, 34 minutes or less, 35 minutes or less, 36 minutes or less, 37 minutes or less, 38 minutes or less, 39 minutes or less, 40 minutes or less, 41 minutes or less, 42 minutes or less, 43 minutes or less, 44 minutes or less, or 45 minutes or less.

In some embodiments, LPS is 1 minute or less. In some embodiments, LPS is 2 minutes or less. In some embodiments, LPS is 3 minutes or less. In some embodiments, LPS is 4 minutes or less. In some embodiments, LPS is 5 minutes or less. In some embodiments, LPS is 6 minutes or less. In some embodiments, LPS is 7 minutes or less. In some embodiments, LPS is 8 minutes or less. In some embodiments, LPS is 9 minutes or less. In some embodiments, LPS is 10 minutes or less.

In some embodiments, LPS is 11 minutes or less. In some embodiments, LPS is 12 minutes or less. In some embodiments, LPS is 13 minutes or less. In some embodiments, LPS is 14 minutes or less. In some embodiments, LPS is 15 minutes or less. In some embodiments, LPS is 16 minutes or less. In some embodiments, LPS is 17 minutes or less. In some embodiments, LPS is 18 minutes or less. In some embodiments, LPS is 19 minutes or less.

In some embodiments, LPS is 20 minutes or less. In some embodiments, LPS is 21 minutes or less. In some embodiments, LPS is 22 minutes or less. In some embodiments, LPS is 23 minutes or less. In some embodiments, LPS is 24 minutes or less. In some embodiments, LPS is 25 minutes or less. In some embodiments, LPS is 26 minutes or less. In some embodiments, LPS is 27 minutes or less. In some embodiments, LPS is 28 minutes or less. In some embodiments, LPS is 29 minutes or less.

In some embodiments, LPS is 30 minutes or less. In some embodiments, LPS is 31 minutes or less. In some embodiments, LPS is 32 minutes or less. In some embodiments, LPS is 33 minutes or less. In some embodiments, LPS is 34 minutes or less. In some embodiments, LPS is 35 minutes or less. In some embodiments, LPS is 36 minutes or less. In some embodiments, LPS is 37 minutes or less. In some embodiments, LPS is 38 minutes or less. In some embodiments, LPS is 39 minutes or less.

In some embodiments, LPS is 40 minutes or less. In some embodiments, LPS is 41 minutes or less. In some embodiments, LPS is 42 minutes or less. In some embodiments, LPS is 43 minutes or less. In some embodiments, LPS is 44 minutes or less. In some embodiments, LPS is 45 minutes or less.

In some embodiments, LPS is about 1 minute or less, about 2 minutes or less, about 3 minutes or less, about 4 minutes or less, about 5 minutes or less, about 6 minutes or less, about 7 minutes or less, about 8 minutes or less, about 9 minutes or less, about 10 minutes or less, about 11 minutes or less, about 12 minutes or less, about 13 minutes or less, about 14 minutes or less, about 15 minutes or less, about 16 minutes or less, about 17 minutes or less, about 18 minutes or less, about 19 minutes or less, about 20 minutes or less, about 21 minutes or less, about 22 minutes or less, about 23 minutes or less, about 24 minutes or less, about 25 minutes or less, about 26 minutes or less, about 27 minutes or less, about 28 minutes or less, about 29 minutes or less, about 30 minutes or less, about 31 minutes or less, about 32 minutes or less, about 33 minutes or less, about 34 minutes or less, about 35 minutes or less, about 36 minutes or less, about 37 minutes or less, about 38 minutes or less, about 39 minutes or less, about 40 minutes or less, about 41 minutes or less, about 42 minutes or less, about 43 minutes or less, about 44 minutes or less, or about 45 minutes or less.

In some embodiments, LPS is about 1 minute or less. In some embodiments, LPS is about 2 minutes or less. In some embodiments, LPS is about 3 minutes or less. In some embodiments, LPS is about 4 minutes or less. In some embodiments, LPS is about 5 minutes or less. In some embodiments, LPS is about 6 minutes or less. In some embodiments, LPS is about 7 minutes or less. In some embodiments, LPS is about 8 minutes or less. In some embodiments, LPS is about 9 minutes or less. In some embodiments, LPS is about 10 minutes or less.

In some embodiments, LPS is about 11 minutes or less. In some embodiments, LPS is about 12 minutes or less. In some embodiments, LPS is about 13 minutes or less. In some embodiments, LPS is about 14 minutes or less. In some embodiments, LPS is about 15 minutes or less. In some embodiments, LPS is about 16 minutes or less. In some embodiments, LPS is about 17 minutes or less. In some embodiments, LPS is about 18 minutes or less. In some embodiments, LPS is about 19 minutes or less.

In some embodiments, LPS is about 20 minutes or less. In some embodiments, LPS is about 21 minutes or less. In some embodiments, LPS is about 22 minutes or less. In some embodiments, LPS is about 23 minutes or less. In some embodiments, LPS is about 24 minutes or less. In some embodiments, LPS is about 25 minutes or less. In some embodiments, LPS is about 26 minutes or less. In some embodiments, LPS is about 27 minutes or less. In some embodiments, LPS is about 28 minutes or less. In some embodiments, LPS is about 29 minutes or less.

In some embodiments, LPS is about 30 minutes or less. In some embodiments, LPS is about 31 minutes or less. In some embodiments, LPS is about 32 minutes or less. In some embodiments, LPS is about 33 minutes or less. In some embodiments, LPS is about 34 minutes or less. In some embodiments, LPS is about 35 minutes or less. In some embodiments, LPS is about 36 minutes or less. In some embodiments, LPS is about 37 minutes or less. In some embodiments, LPS is about 38 minutes or less. In some embodiments, LPS is about 39 minutes or less.

In some embodiments, LPS is about 40 minutes or less. In some embodiments, LPS is about 41 minutes or less. In some embodiments, LPS is about 42 minutes or less. In some embodiments, LPS is about 43 minutes or less. In some embodiments, LPS is about 44 minutes or less. In some embodiments, LPS is about 45 minutes or less.

In some embodiments, the subject has insomnia.

Methods of Reducing Wake After Sleep Onset (WASO)

Provided herein is a method of reducing wake after sleep onset (WASO) in a subject comprising administering to the subject 5 mg or 10 mg of lemborexant or an equivalent dose of a pharmaceutically acceptable salt thereof. Also disclosed herein is lemborexant or a pharmaceutically acceptable salt thereof for use in reducing WASO in a subject comprising administering to the subject 5 mg or 10 mg of lemborexant or an equivalent dose of a pharmaceutically acceptable salt thereof.

In some embodiments, the WASO is reduced for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days. In some embodiments, the WASO is reduced for at least 1 day. In some embodiments, the WASO is reduced for at least 2 days. In some embodiments, the WASO is reduced for at least 3 days. In some embodiments, the WASO is reduced for at least 4 days. In some embodiments, the WASO is reduced for at least 5 days. In some embodiments, the WASO is reduced for at least 6 days. In some embodiments, the WASO is reduced for at least 7 days. In some embodiments, the WASO is reduced for at least 8 days. In some embodiments, the WASO is reduced for at least 9 days. In some embodiments, the WASO is reduced for at least 10 days.

In some embodiments, the WASO is reduced for at least 11 days. In some embodiments, the WASO is reduced for at least 12 days. In some embodiments, the WASO is reduced for at least 13 days. In some embodiments, the WASO is reduced for at least 14 days. In some embodiments, the WASO is reduced for at least 15 days. In some embodiments, the WASO is reduced for at least 16 days. In some embodiments, the WASO is reduced for at least 17 days. In some embodiments, the WASO is reduced for at least 18 days. In some embodiments, the WASO is reduced for at least 19 days.

In some embodiments, the WASO is reduced for at least 20 days. In some embodiments, the WASO is reduced for at least 21 days. In some embodiments, the WASO is reduced for at least 22 days. In some embodiments, the WASO is reduced for at least 23 days. In some embodiments, the WASO is reduced for at least 24 days. In some embodiments, the WASO is reduced for at least 25 days. In some embodiments, the WASO is reduced for at least 26 days. In some embodiments, the WASO is reduced for at least 27 days. In some embodiments, the WASO is reduced for at least 28 days. In some embodiments, the WASO is reduced for at least 29 days. In some embodiments, the WASO is reduced for at least 30 days.

In some embodiments, the WASO is reduced for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days, relative to baseline. In some embodiments, the WASO is reduced for at least 1 day, relative to baseline. In some embodiments, the WASO is reduced for at least 2 days, relative to baseline. In some embodiments, the WASO is reduced for at least 3 days, relative to baseline. In some embodiments, the WASO is reduced for at least 4 days, relative to baseline. In some embodiments, the WASO is reduced for at least 5 days, relative to baseline. In some embodiments, the WASO is reduced for at least 6 days, relative to baseline. In some embodiments, the WASO is reduced for at least 7 days, relative to baseline. In some embodiments, the WASO is reduced for at least 8 days, relative to baseline. In some embodiments, the WASO is reduced for at least 9 days, relative to baseline. In some embodiments, the WASO is reduced for at least 10 days, relative to baseline.

In some embodiments, the WASO is reduced for at least 11 days, relative to baseline. In some embodiments, the WASO is reduced for at least 12 days, relative to baseline. In some embodiments, the WASO is reduced for at least 13 days, relative to baseline. In some embodiments, the WASO is reduced for at least 14 days, relative to baseline. In some embodiments, the WASO is reduced for at least 15 days, relative to baseline. In some embodiments, the WASO is reduced for at least 16 days, relative to baseline. In some embodiments, the WASO is reduced for at least 17 days, relative to baseline. In some embodiments, the WASO is reduced for at least 18 days, relative to baseline. In some embodiments, the WASO is reduced for at least 19 days, relative to baseline.

In some embodiments, the WASO is reduced for at least 20 days, relative to baseline. In some embodiments, the WASO is reduced for at least 21 days, relative to baseline. In some embodiments, the WASO is reduced for at least 22 days, relative to baseline. In some embodiments, the WASO is reduced for at least 23 days, relative to baseline. In some embodiments, the WASO is reduced for at least 24 days, relative to baseline. In some embodiments, the WASO is reduced for at least 25 days, relative to baseline. In some embodiments, the WASO is reduced for at least 26 days, relative to baseline. In some embodiments, the WASO is reduced for at least 27 days, relative to baseline. In some embodiments, the WASO is reduced for at least 28 days, relative to baseline. In some embodiments, the WASO is reduced for at least 29 days, relative to baseline. In some embodiments, the WASO is reduced for at least 30 days, relative to baseline.

In some embodiments, the WASO is reduced for at least one month. In some embodiments, the WASO is reduced for at least two months. In some embodiments, the WASO is reduced for at least three months. In some embodiments, the WASO is reduced for at least 6 months. In some embodiments, the WASO is reduced for at least 9 months. In some embodiments, the WASO is reduced for at least 12 months. In some embodiments, the WASO is reduced for at least 18 months. In some embodiments, the WASO is reduced for 2 years or more.

In some embodiments, the WASO is reduced for at least one month, relative to baseline. In some embodiments, the WASO is reduced for at least two months, relative to baseline. In some embodiments, the WASO is reduced for at least three months, relative to baseline. In some embodiments, the WASO is reduced for at least 6 months, relative to baseline. In some embodiments, the WASO is reduced for at least 9 months, relative to baseline. In some embodiments, the WASO is reduced for at least 12 months, relative to baseline. In some embodiments, the WASO is reduced for at least 18 months, relative to baseline. In some embodiments, the WASO is reduced for 2 years or more, relative to baseline.

In some embodiments, lemborexant or salt thereof is administered to the subject for at least one month. In some embodiments, lemborexant or salt thereof is administered to the subject for at least two months. In some embodiments, lemborexant or salt thereof is administered to the subject for at least three months. In some embodiments, lemborexant or salt thereof is administered to the subject for at least 6 months. In some embodiments, lemborexant or salt thereof is administered to the subject for at least 9 months. In some embodiments, lemborexant or salt thereof is administered to the subject for at least 12 months. In some embodiments, lemborexant or salt thereof is administered to the subject for at least 18 months. In some embodiments, lemborexant or salt thereof is administered to the subject for two years or more.

In some embodiments, the WASO is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to baseline. In some embodiments, the WASO is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 31 minutes, at least 32 minutes, at least 33 minutes, at least 34 minutes, at least 35 minutes, at least 36 minutes, at least 37 minutes, at least 38 minutes, at least 39 minutes, at least 40 minutes, at least 41 minutes, at least 42 minutes, at least 43 minutes, at least 44 minutes, at least 45 minutes, at least 46 minutes, at least 47 minutes, at least 48 minutes, at least 49 minutes, at least 50 minutes, at least 51 minutes, at least 52 minutes, at least 53 minutes, at least 54 minutes, at least 55 minutes, at least 56 minutes, at least 57 minutes, at least 58 minutes, at least 59 minutes, at least 60 minutes, at least 61 minutes, at least 62 minutes, at least 63 minutes, at least 64 minutes, at least 65 minutes, at least 66 minutes, at least 67 minutes, at least 68 minutes, at least 69 minutes, or at least 70 minutes, relative to baseline.

In some embodiments, the WASO is reduced by at least 1 minute, relative to baseline. In some embodiments, the WASO is reduced by at least 2 minutes, relative to baseline. In some embodiments, the WASO is reduced by at least 3 minutes, relative to baseline. In some embodiments, the WASO is reduced by at least 4 minutes, relative to baseline. In some embodiments, the WASO is reduced by at least 5 minutes, relative to baseline. In some embodiments, the WASO is reduced by at least 6 minutes, relative to baseline. In some embodiments, the WASO is reduced by at least 7 minutes, relative to baseline. In some embodiments, the WASO is reduced by at least 8 minutes, relative to baseline. In some embodiments, the WASO is reduced by at least 9 minutes, relative to baseline. In some embodiments, the WASO is reduced by at least 10 minutes, relative to baseline.

In some embodiments, the WASO is reduced by at least 11 minutes, relative to baseline. In some embodiments, the WASO is reduced by at least 12 minutes, relative to baseline. In some embodiments, the WASO is reduced by at least 13 minutes, relative to baseline. In some embodiments, the WASO is reduced by at least 14 minutes, relative to baseline. In some embodiments, the WASO is reduced by at least 15 minutes, relative to baseline. In some embodiments, the WASO is reduced by at least 16 minutes, relative to baseline. In some embodiments, the WASO is reduced by at least 17 minutes, relative to baseline. In some embodiments, the WASO is reduced by at least 18 minutes, relative to baseline. In some embodiments, the WASO is reduced by at least 19 minutes, relative to baseline. In some embodiments, the WASO is reduced by at least 20 minutes, relative to baseline.

In some embodiments, the WASO is reduced by at least 21 minutes, relative to baseline. In some embodiments, the WASO is reduced by at least 22 minutes, relative to baseline. In some embodiments, the WASO is reduced by at least 23 minutes, relative to baseline. In some embodiments, the WASO is reduced by at least 24 minutes, relative to baseline. In some embodiments, the WASO is reduced by at least 25 minutes, relative to baseline. In some embodiments, the WASO is reduced by at least 26 minutes, relative to baseline. In some embodiments, the WASO is reduced by at least 27 minutes, relative to baseline. In some embodiments, the WASO is reduced by at least 28 minutes, relative to baseline. In some embodiments, the WASO is reduced by at least 29 minutes, relative to baseline.

In some embodiments, the WASO is reduced by at least 30 minutes, relative to baseline. In some embodiments, the WASO is reduced by at least 31 minutes, relative to baseline. In some embodiments, the WASO is reduced by at least 32 minutes, relative to baseline. In some embodiments, the WASO is reduced by at least 33 minutes, relative to baseline. In some embodiments, the WASO is reduced by at least 34 minutes, relative to baseline. In some embodiments, the WASO is reduced by at least 35 minutes, relative to baseline. In some embodiments, the WASO is reduced by at least 36 minutes, relative to baseline. In some embodiments, the WASO is reduced by at least 37 minutes, relative to baseline. In some embodiments, the WASO is reduced by at least 38 minutes, relative to baseline. In some embodiments, the WASO is reduced by at least 39 minutes, relative to baseline. In some embodiments, the WASO is reduced by at least 40 minutes, relative to baseline.

In some embodiments, the WASO is reduced by at least 41 minutes, relative to baseline. In some embodiments, the WASO is reduced by at least 42 minutes, relative to baseline. In some embodiments, the WASO is reduced by at least 43 minutes, relative to baseline. In some embodiments, the WASO is reduced by at least 44 minutes, relative to baseline. In some embodiments, the WASO is reduced by at least 45 minutes, relative to baseline. In some embodiments, the WASO is reduced by at least 46 minutes, relative to baseline. In some embodiments, the WASO is reduced by at least 47 minutes, relative to baseline. In some embodiments, the WASO is reduced by at least 48 minutes, relative to baseline. In some embodiments, the WASO is reduced by at least 49 minutes, relative to baseline. In some embodiments, the WASO is reduced by at least 50 minutes, relative to baseline. In some embodiments, the WASO is reduced by at least 51 minutes, relative to baseline.

In some embodiments, the WASO is reduced by at least 52 minutes, relative to baseline. In some embodiments, the WASO is reduced by at least 53 minutes, relative to baseline. In some embodiments, the WASO is reduced by at least 54 minutes, relative to baseline. In some embodiments, the WASO is reduced by at least 55 minutes, relative to baseline. In some embodiments, the WASO is reduced by at least 56 minutes, relative to baseline. In some embodiments, the WASO is reduced by at least 57 minutes, relative to baseline. In some embodiments, the WASO is reduced by at least 58 minutes, relative to baseline. In some embodiments, the WASO is reduced by at least 59 minutes, relative to baseline. In some embodiments, the WASO is reduced by at least 60 minutes, relative to baseline.

In some embodiments, the WASO is reduced by at least 61 minutes, relative to baseline. In some embodiments, the WASO is reduced by at least 62 minutes, relative to baseline. In some embodiments, the WASO is reduced by at least 63 minutes, relative to baseline. In some embodiments, the WASO is reduced by at least 64 minutes, relative to baseline. In some embodiments, the WASO is reduced by at least 65 minutes, relative to baseline. In some embodiments, the WASO is reduced by at least 66 minutes, relative to baseline. In some embodiments, the WASO is reduced by at least 67 minutes, relative to baseline. In some embodiments, the WASO is reduced by at least 68 minutes, relative to baseline. In some embodiments, the WASO is reduced by at least 69 minutes, relative to baseline. In some embodiments, the WASO is reduced by at least 70 minutes, relative to baseline.

In some embodiments, the WASO is reduced by about 1 minute, relative to baseline. In some embodiments, the WASO is reduced by about 2 minutes, relative to baseline. In some embodiments, the WASO is reduced by about 3 minutes, relative to baseline. In some embodiments, the WASO is reduced by about 4 minutes, relative to baseline. In some embodiments, the WASO is reduced by about 5 minutes, relative to baseline. In some embodiments, the WASO is reduced by about 6 minutes, relative to baseline. In some embodiments, the WASO is reduced by about 7 minutes, relative to baseline. In some embodiments, the WASO is reduced by about 8 minutes, relative to baseline. In some embodiments, the WASO is reduced by about 9 minutes, relative to baseline. In some embodiments, the WASO is reduced by about 10 minutes, relative to baseline.

In some embodiments, the WASO is reduced by about 11 minutes, relative to baseline. In some embodiments, the WASO is reduced by about 12 minutes, relative to baseline.

In some embodiments, the WASO is reduced by about 13 minutes, relative to baseline. In some embodiments, the WASO is reduced by about 14 minutes, relative to baseline. In some embodiments, the WASO is reduced by about 15 minutes, relative to baseline. In some embodiments, the WASO is reduced by about 16 minutes, relative to baseline. In some embodiments, the WASO is reduced by about 17 minutes, relative to baseline. In some embodiments, the WASO is reduced by about 18 minutes, relative to baseline. In some embodiments, the WASO is reduced by about 19 minutes, relative to baseline. In some embodiments, the WASO is reduced by about 20 minutes, relative to baseline.

In some embodiments, the WASO is reduced by about 21 minutes, relative to baseline. In some embodiments, the WASO is reduced by about 22 minutes, relative to baseline. In some embodiments, the WASO is reduced by about 23 minutes, relative to baseline. In some embodiments, the WASO is reduced by about 24 minutes, relative to baseline. In some embodiments, the WASO is reduced by about 25 minutes, relative to baseline. In some embodiments, the WASO is reduced by about 26 minutes, relative to baseline. In some embodiments, the WASO is reduced by about 27 minutes, relative to baseline. In some embodiments, the WASO is reduced by about 28 minutes, relative to baseline. In some embodiments, the WASO is reduced by about 29 minutes, relative to baseline.

In some embodiments, the WASO is reduced by about 30 minutes, relative to baseline. In some embodiments, the WASO is reduced by about 31 minutes, relative to baseline. In some embodiments, the WASO is reduced by about 32 minutes, relative to baseline. In some embodiments, the WASO is reduced by about 33 minutes, relative to baseline. In some embodiments, the WASO is reduced by about 34 minutes, relative to baseline. In some embodiments, the WASO is reduced by about 35 minutes, relative to baseline. In some embodiments, the WASO is reduced by about 36 minutes, relative to baseline. In some embodiments, the WASO is reduced by about 37 minutes, relative to baseline. In some embodiments, the WASO is reduced by about 38 minutes, relative to baseline. In some embodiments, the WASO is reduced by about 39 minutes, relative to baseline. In some embodiments, the WASO is reduced by about 40 minutes, relative to baseline.

In some embodiments, the WASO is reduced by about 41 minutes, relative to baseline. In some embodiments, the WASO is reduced by about 42 minutes, relative to baseline. In some embodiments, the WASO is reduced by about 43 minutes, relative to baseline. In some embodiments, the WASO is reduced by about 44 minutes, relative to baseline. In some embodiments, the WASO is reduced by about 45 minutes, relative to baseline. In some embodiments, the WASO is reduced by about 46 minutes, relative to baseline. In some embodiments, the WASO is reduced by about 47 minutes, relative to baseline. In some embodiments, the WASO is reduced by about 48 minutes, relative to baseline. In some embodiments, the WASO is reduced by about 49 minutes, relative to baseline. In some embodiments, the WASO is reduced by about 50 minutes, relative to baseline. In some embodiments, the WASO is reduced by about 51 minutes, relative to baseline.

In some embodiments, the WASO is reduced by about 52 minutes, relative to baseline. In some embodiments, the WASO is reduced by about 53 minutes, relative to baseline. In some embodiments, the WASO is reduced by about 54 minutes, relative to baseline. In some embodiments, the WASO is reduced by about 55 minutes, relative to baseline. In some embodiments, the WASO is reduced by about 56 minutes, relative to baseline. In some embodiments, the WASO is reduced by about 57 minutes, relative to baseline. In some embodiments, the WASO is reduced by about 58 minutes, relative to baseline. In some embodiments, the WASO is reduced by about 59 minutes, relative to baseline. In some embodiments, the WASO is reduced by about 60 minutes, relative to baseline.

In some embodiments, the WASO is reduced by about 61 minutes, relative to baseline. In some embodiments, the WASO is reduced by about 62 minutes, relative to baseline. In some embodiments, the WASO is reduced by about 63 minutes, relative to baseline. In some embodiments, the WASO is reduced by about 64 minutes, relative to baseline. In some embodiments, the WASO is reduced by about 65 minutes, relative to baseline. In some embodiments, the WASO is reduced by about 66 minutes, relative to baseline. In some embodiments, the WASO is reduced by about 67 minutes, relative to baseline. In some embodiments, the WASO is reduced by about 68 minutes, relative to baseline. In some embodiments, the WASO is reduced by about 69 minutes, relative to baseline. In some embodiments, the WASO is reduced by about 70 minutes, relative to baseline.

In some embodiments, 5 mg of lemborexant or an equivalent dose of a pharmaceutically acceptable salt thereof is administered to a subject and the WASO is reduced by about 44 minutes, relative to baseline. In some embodiments, 5 mg of lemborexant or an equivalent dose of a pharmaceutically acceptable salt thereof is administered to a subject and the WASO is reduced by about 50 minutes, relative to baseline.

In some embodiments, 5 mg of lemborexant or an equivalent dose of a pharmaceutically acceptable salt thereof is administered to a subject and the WASO is reduced by at least 43 minutes, relative to baseline. In some embodiments, 5 mg of lemborexant or an equivalent dose of a pharmaceutically acceptable salt thereof is administered to a subject and the WASO is reduced by at least 49 minutes, relative to baseline.

In some embodiments, 10 mg of lemborexant or an equivalent dose of a pharmaceutically acceptable salt thereof is administered to a subject and the WASO is reduced by about 46 minutes, relative to baseline. In some embodiments, 10 mg of lemborexant or an equivalent dose of a pharmaceutically acceptable salt thereof is administered to a subject and the WASO is reduced by about 60 minutes, relative to baseline.

In some embodiments, 10 mg of lemborexant or an equivalent dose of a pharmaceutically acceptable salt thereof is administered to a subject and the WASO is reduced by at least 46 minutes, relative to baseline. In some embodiments, 10 mg of lemborexant or an equivalent dose of a pharmaceutically acceptable salt thereof is administered to a subject and the sWASO is reduced by at least 59 minutes, relative to baseline.

In some embodiments, the WASO is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to placebo. In some embodiments, the WASO is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 31 minutes, at least 32 minutes, at least 33 minutes, at least 34 minutes, or at least 35 minutes, relative to placebo.

In some embodiments, the WASO is reduced by at least 1 minute, relative to placebo. In some embodiments, the WASO is reduced by at least 2 minutes, relative to placebo. In some embodiments, the WASO is reduced by at least 3 minutes, relative to placebo. In some embodiments, the WASO is reduced by at least 4 minutes, relative to placebo. In some embodiments, the WASO is reduced by at least 5 minutes, relative to placebo. In some embodiments, the WASO is reduced by at least 6 minutes, relative to placebo. In some embodiments, the WASO is reduced by at least 7 minutes, relative to placebo. In some embodiments, the WASO is reduced by at least 8 minutes, relative to placebo. In some embodiments, the WASO is reduced by at least 9 minutes, relative to placebo. In some embodiments, the WASO is reduced by at least 10 minutes, relative to placebo.

In some embodiments, the WASO is reduced by at least 11 minutes, relative to placebo. In some embodiments, the WASO is reduced by at least 12 minutes, relative to placebo. In some embodiments, the WASO is reduced by at least 13 minutes, relative to placebo. In some embodiments, the WASO is reduced by at least 14 minutes, relative to placebo. In some embodiments, the WASO is reduced by at least 15 minutes, relative to placebo. In some embodiments, the WASO is reduced by at least 16 minutes, relative to placebo. In some embodiments, the WASO is reduced by at least 17 minutes, relative to placebo. In some embodiments, the WASO is reduced by at least 18 minutes, relative to placebo. In some embodiments, the WASO is reduced by at least 19 minutes, relative to placebo. In some embodiments, the WASO is reduced by at least 20 minutes, relative to placebo.

In some embodiments, the WASO is reduced by at least 21 minutes, relative to placebo. In some embodiments, the WASO is reduced by at least 22 minutes, relative to placebo. In some embodiments, the WASO is reduced by at least 23 minutes, relative to placebo. In some embodiments, the WASO is reduced by at least 24 minutes, relative to placebo. In some embodiments, the WASO is reduced by at least 25 minutes, relative to placebo. In some embodiments, the WASO is reduced by at least 26 minutes, relative to placebo. In some embodiments, the WASO is reduced by at least 27 minutes, relative to placebo. In some embodiments, the WASO is reduced by at least 28 minutes, relative to placebo. In some embodiments, the WASO is reduced by at least 29 minutes, relative to placebo. In some embodiments, the WASO is reduced by at least 30 minutes, relative to placebo.

In some embodiments, the WASO is reduced by at least 31 minutes, relative to placebo. In some embodiments, the WASO is reduced by at least 32 minutes, relative to placebo. In some embodiments, the WASO is reduced by at least 33 minutes, relative to placebo. In some embodiments, the WASO is reduced by at least 34 minutes, relative to placebo. In some embodiments, the WASO is reduced by at least 35 minutes, relative to placebo.

In some embodiments, the WASO is reduced by about 1 minute, relative to placebo. In some embodiments, the WASO is reduced by about 2 minutes, relative to placebo. In some embodiments, the WASO is reduced by about 3 minutes, relative to placebo. In some embodiments, the WASO is reduced by about 4 minutes, relative to placebo. In some embodiments, the WASO is reduced by about 5 minutes, relative to placebo. In some embodiments, the WASO is reduced by about 6 minutes, relative to placebo. In some embodiments, the WASO is reduced by about 7 minutes, relative to placebo. In some embodiments, the WASO is reduced by about 8 minutes, relative to baseline. In some embodiments, the WASO is reduced by about 9 minutes, relative to baseline. In some embodiments, the WASO is reduced by about 10 minutes, relative to placebo.

In some embodiments, the WASO is reduced by about 11 minutes, relative to placebo. In some embodiments, the WASO is reduced by about 12 minutes, relative to placebo. In some embodiments, the WASO is reduced by about 13 minutes, relative to placebo. In some embodiments, the WASO is reduced by about 14 minutes, relative to placebo. In some embodiments, the WASO is reduced by about 15 minutes, relative to placebo. In some embodiments, the WASO is reduced by about 16 minutes, relative to placebo. In some embodiments, the WASO is reduced by about 17 minutes, relative to placebo. In some embodiments, the WASO is reduced by about 18 minutes, relative to placebo. In some embodiments, the WASO is reduced by about 19 minutes, relative to placebo. In some embodiments, the WASO is reduced by about 20 minutes, relative to placebo.

In some embodiments, the WASO is reduced by about 21 minutes, relative to placebo. In some embodiments, the WASO is reduced by about 22 minutes, relative to placebo. In some embodiments, the WASO is reduced by about 23 minutes, relative to placebo. In some embodiments, the WASO is reduced by about 24 minutes, relative to placebo. In some embodiments, the WASO is reduced by about 25 minutes, relative to placebo. In some embodiments, the WASO is reduced by about 26 minutes, relative to placebo. In some embodiments, the WASO is reduced by about 27 minutes, relative to placebo. In some embodiments, the WASO is reduced by about 28 minutes, relative to placebo. In some embodiments, the WASO is reduced by about 29 minutes, relative to placebo. In some embodiments, the WASO is reduced by about 30 minutes, relative to placebo.

In some embodiments, the WASO is reduced by about 31 minutes, relative to placebo. In some embodiments, the WASO is reduced by about 32 minutes, relative to placebo. In some embodiments, the WASO is reduced by about 33 minutes, relative to placebo. In some embodiments, the WASO is reduced by about 34 minutes, relative to placebo. In some embodiments, the WASO is reduced by about 35 minutes, relative to placebo.

In some embodiments, 5 mg of lemborexant or an equivalent dose of a pharmaceutically acceptable salt thereof is administered to a subject and the WASO is reduced by about 25 minutes, relative to placebo. In some embodiments, 5 mg of lemborexant or an equivalent dose of a pharmaceutically acceptable salt thereof is administered to a subject and the WASO is reduced by about 35 minutes, relative to placebo.

In some embodiments, 5 mg of lemborexant or an equivalent dose of a pharmaceutically acceptable salt thereof is administered to a subject and the WASO is reduced by at least 23 minutes, relative to placebo. In some embodiments, 5 mg of lemborexant or an equivalent dose of a pharmaceutically acceptable salt thereof is administered to a subject and the WASO is reduced by at least 33 minutes, relative to placebo.

In some embodiments, 10 mg of lemborexant or an equivalent dose of a pharmaceutically acceptable salt thereof is administered to a subject and the WASO is reduced by about 25 minutes, relative to placebo. In some embodiments, 10 mg of lemborexant or an equivalent dose of a pharmaceutically acceptable salt thereof is administered to a subject and the WASO is reduced by about 40 minutes, relative to placebo.

In some embodiments, 10 mg of lemborexant or an equivalent dose of a pharmaceutically acceptable salt thereof is administered to a subject and the WASO is reduced by at least 25 minutes, relative to placebo. In some embodiments, 10 mg of lemborexant or an equivalent dose of a pharmaceutically acceptable salt thereof is administered to a subject and the WASO is reduced by at least 42 minutes, relative to placebo.

In some embodiments, the WASO is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to zolpidem. In some embodiments, the WASO is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, relative to zolpidem.

In some embodiments, the WASO is reduced by at least 1 minute, relative to zolpidem. In some embodiments, the WASO is reduced by at least 2 minutes, relative to zolpidem. In some embodiments, the WASO is reduced by at least 3 minutes, relative to zolpidem. In some embodiments, the WASO is reduced by at least 4 minutes, relative to zolpidem. In some embodiments, the WASO is reduced by at least 5 minutes, relative to zolpidem. In some embodiments, the WASO is reduced by at least 6 minutes, relative to zolpidem. In some embodiments, the WASO is reduced by at least 7 minutes, relative to zolpidem. In some embodiments, the WASO is reduced by at least 8 minutes, relative to zolpidem. In some embodiments, the WASO is reduced by at least 9 minutes, relative to zolpidem. In some embodiments, the WASO is reduced by at least 10 minutes, relative to zolpidem.

In some embodiments, the WASO is reduced by at least 11 minutes, relative to zolpidem. In some embodiments, the WASO is reduced by at least 12 minutes, relative to zolpidem. In some embodiments, the WASO is reduced by at least 13 minutes, relative to zolpidem. In some embodiments, the WASO is reduced by at least 14 minutes, relative to zolpidem. In some embodiments, the WASO is reduced by at least 15 minutes, relative to zolpidem. In some embodiments, the WASO is reduced by at least 16 minutes, relative to zolpidem. In some embodiments, the WASO is reduced by at least 17 minutes, relative to zolpidem. In some embodiments, the WASO is reduced by at least 18 minutes, relative to zolpidem. In some embodiments, the WASO is reduced by at least 19 minutes, relative to zolpidem. In some embodiments, the WASO is reduced by at least 20 minutes, relative to zolpidem.

In some embodiments, the WASO is reduced by at least 21 minutes, relative to zolpidem. In some embodiments, the WASO is reduced by at least 22 minutes, relative to zolpidem. In some embodiments, the WASO is reduced by at least 23 minutes, relative to zolpidem. In some embodiments, the WASO is reduced by at least 24 minutes, relative to zolpidem. In some embodiments, the WASO is reduced by at least 25 minutes, relative to zolpidem.

In some embodiments, the WASO is reduced by about 1 minute, relative to zolpidem. In some embodiments, the WASO is reduced by about 2 minutes, relative to zolpidem. In some embodiments, the WASO is reduced by about 3 minutes, relative to zolpidem. In some embodiments, the WASO is reduced by about 4 minutes, relative to zolpidem. In some embodiments, the WASO is reduced by about 5 minutes, relative to zolpidem. In some embodiments, the WASO is reduced by about 6 minutes, relative to zolpidem. In some embodiments, the WASO is reduced by about 7 minutes, relative to zolpidem. In some embodiments, the WASO is reduced by about 8 minutes, relative to baseline. In some embodiments, the WASO is reduced by about 9 minutes, relative to baseline. In some embodiments, the WASO is reduced by about 10 minutes, relative to zolpidem.

In some embodiments, the WASO is reduced by about 11 minutes, relative to zolpidem. In some embodiments, the WASO is reduced by about 12 minutes, relative to zolpidem. In some embodiments, the WASO is reduced by about 13 minutes, relative to zolpidem. In some embodiments, the WASO is reduced by about 14 minutes, relative to zolpidem. In some embodiments, the WASO is reduced by about 15 minutes, relative to zolpidem. In some embodiments, the WASO is reduced by about 16 minutes, relative to zolpidem. In some embodiments, the WASO is reduced by about 17 minutes, relative to zolpidem. In some embodiments, the WASO is reduced by about 18 minutes, relative to zolpidem. In some embodiments, the WASO is reduced by about 19 minutes, relative to zolpidem. In some embodiments, the WASO is reduced by about 20 minutes, relative to zolpidem.

In some embodiments, the WASO is reduced by about 21 minutes, relative to zolpidem. In some embodiments, the WASO is reduced by about 22 minutes, relative to zolpidem. In some embodiments, the WASO is reduced by about 23 minutes, relative to zolpidem. In some embodiments, the WASO is reduced by about 24 minutes, relative to zolpidem. In some embodiments, the WASO is reduced by about 25 minutes, relative to zolpidem.

In some embodiments, 5 mg of lemborexant or an equivalent dose of a pharmaceutically acceptable salt thereof is administered to a subject and the WASO is reduced by about 6 minutes, relative to zolpidem. In some embodiments, 5 mg of lemborexant or an equivalent dose of a pharmaceutically acceptable salt thereof is administered to a subject and the WASO is reduced by about 7 minutes, relative to zolpidem.

In some embodiments, 5 mg of lemborexant or an equivalent dose of a pharmaceutically acceptable salt thereof is administered to a subject and the WASO is reduced by at least 6 minutes, relative to zolpidem. In some embodiments, 5 mg of lemborexant or an equivalent dose of a pharmaceutically acceptable salt thereof is administered to a subject and the WASO is reduced by at least 7 minutes, relative to zolpidem.

In some embodiments, 10 mg of lemborexant or an equivalent dose of a pharmaceutically acceptable salt thereof is administered to a subject and the WASO is reduced by about 10 minutes, relative to zolpidem. In some embodiments, 10 mg of lemborexant or an equivalent dose of a pharmaceutically acceptable salt thereof is administered to a subject and the WASO is reduced by about 15 minutes, relative to zolpidem.

In some embodiments, 10 mg of lemborexant or an equivalent dose of a pharmaceutically acceptable salt thereof is administered to a subject and the WASO is reduced by at least 9 minutes, relative to zolpidem. In some embodiments, 10 mg of lemborexant or an equivalent dose of a pharmaceutically acceptable salt thereof is administered to a subject and the WASO is reduced by at least 15 minutes, relative to zolpidem.

In some embodiments, the subject has insomnia.

Methods of Reducing Wake After Sleep Onset in the Second Half of the Night (WASO2H)

Provided herein is a method of reducing wake after sleep onset in the second half of the night (WASO2H) in a subject comprising administering to the subject 5 mg or 10 mg of lemborexant or an equivalent dose of a pharmaceutically acceptable salt thereof. Also disclosed herein is lemborexant or a pharmaceutically acceptable salt thereof for use in reducing WASO2H in a subject comprising administering to the subject 5 mg or 10 mg of lemborexant or an equivalent dose of a pharmaceutically acceptable salt thereof.

In some embodiments, the WASO2H is reduced for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days. In some embodiments, the WASO2H is reduced for at least 1 day. In some embodiments, the WASO2H is reduced for at least 2 days. In some embodiments, the WASO2H is reduced for at least 3 days. In some embodiments, the WASO2H is reduced for at least 4 days. In some embodiments, the WASO2H is reduced for at least 5 days. In some embodiments, the WASO2H is reduced for at least 6 days. In some embodiments, the WASO2H is reduced for at least 7 days. In some embodiments, the WASO2H is reduced for at least 8 days. In some embodiments, the WASO2H is reduced for at least 9 days. In some embodiments, the WASO2H is reduced for at least 10 days.

In some embodiments, the WASO2H is reduced for at least 11 days. In some embodiments, the WASO2H is reduced for at least 12 days. In some embodiments, the WASO2H is reduced for at least 13 days. In some embodiments, the WASO2H is reduced for at least 14 days. In some embodiments, the WASO2H is reduced for at least 15 days. In some embodiments, the WASO2H is reduced for at least 16 days. In some embodiments, the WASO2H is reduced for at least 17 days. In some embodiments, the WASO2H is reduced for at least 18 days. In some embodiments, the WASO2H is reduced for at least 19 days.

In some embodiments, the WASO2H is reduced for at least 20 days. In some embodiments, the WASO2H is reduced for at least 21 days. In some embodiments, the WASO2H is reduced for at least 22 days. In some embodiments, the WASO2H is reduced for at least 23 days. In some embodiments, the WASO2H is reduced for at least 24 days. In some embodiments, the WASO2H is reduced for at least 25 days. In some embodiments, the WASO2H is reduced for at least 26 days. In some embodiments, the WASO2H is reduced for at least 27 days. In some embodiments, the WASO2H is reduced for at least 28 days. In some embodiments, the WASO2H is reduced for at least 29 days. In some embodiments, the WASO2H is reduced for at least 30 days.

In some embodiments, the WASO2H is reduced for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days, relative to baseline. In some embodiments, the WASO2H is reduced for at least 1 day, relative to baseline. In some embodiments, the WASO2H is reduced for at least 2 days, relative to baseline. In some embodiments, the WASO2H is reduced for at least 3 days, relative to baseline. In some embodiments, the WASO2H is reduced for at least 4 days, relative to baseline. In some embodiments, the WASO2H is reduced for at least 5 days, relative to baseline. In some embodiments, the WASO2H is reduced for at least 6 days, relative to baseline. In some embodiments, the WASO2H is reduced for at least 7 days, relative to baseline. In some embodiments, the WASO2H is reduced for at least 8 days, relative to baseline. In some embodiments, the WASO2H is reduced for at least 9 days, relative to baseline. In some embodiments, the WASO2H is reduced for at least 10 days, relative to baseline.

In some embodiments, the WASO2H is reduced for at least 11 days, relative to baseline. In some embodiments, the WASO2H is reduced for at least 12 days, relative to baseline. In some embodiments, the WASO2H is reduced for at least 13 days, relative to baseline. In some embodiments, the WASO2H is reduced for at least 14 days, relative to baseline. In some embodiments, the WASO2H is reduced for at least 15 days, relative to baseline. In some embodiments, the WASO2H is reduced for at least 16 days, relative to baseline. In some embodiments, the WASO2H is reduced for at least 17 days, relative to baseline. In some embodiments, the WASO2H is reduced for at least 18 days, relative to baseline. In some embodiments, the WASO2H is reduced for at least 19 days, relative to baseline.

In some embodiments, the WASO2H is reduced for at least 20 days, relative to baseline. In some embodiments, the WASO2H is reduced for at least 21 days, relative to baseline. In some embodiments, the WASO2H is reduced for at least 22 days, relative to baseline. In some embodiments, the WASO2H is reduced for at least 23 days, relative to baseline. In some embodiments, the WASO2H is reduced for at least 24 days, relative to baseline. In some embodiments, the WASO2H is reduced for at least 25 days, relative to baseline. In some embodiments, the WASO2H is reduced for at least 26 days, relative to baseline. In some embodiments, the WASO2H is reduced for at least 27 days, relative to baseline. In some embodiments, the WASO2H is reduced for at least 28 days, relative to baseline. In some embodiments, the WASO2H is reduced for at least 29 days, relative to baseline. In some embodiments, the WASO2H is reduced for at least 30 days, relative to baseline.

In some embodiments, the WASO2H is reduced for at least one month. In some embodiments, the WASO2H is reduced for at least two months. In some embodiments, the WASO2H is reduced for at least three months. In some embodiments, the WASO2H is reduced for at least 6 months. In some embodiments, the WASO2H is reduced for at least 9 months. In some embodiments, the WASO2H is reduced for at least 12 months. In some embodiments, the WASO2H is reduced for at least 18 months. In some embodiments, the WASO2H is reduced for 2 years or more.

In some embodiments, the WASO2H is reduced for at least one month, relative to baseline. In some embodiments, the WASO2H is reduced for at least two months, relative to baseline. In some embodiments, the WASO2H is reduced for at least three months, relative to baseline. In some embodiments, the WASO2H is reduced for at least 6 months, relative to baseline. In some embodiments, the WASO2H is reduced for at least 9 months, relative to baseline. In some embodiments, the WASO2H is reduced for at least 12 months, relative to baseline. In some embodiments, the WASO2H is reduced for at least 18 months, relative to baseline. In some embodiments, the WASO2H is reduced for 2 years or more, relative to baseline.

In some embodiments, lemborexant or salt thereof is administered to the subject for at least one month. In some embodiments, lemborexant or salt thereof is administered to the subject for at least two months. In some embodiments, lemborexant or salt thereof is administered to the subject for at least three months. In some embodiments, lemborexant or salt thereof is administered to the subject for at least 6 months. In some embodiments, lemborexant or salt thereof is administered to the subject for at least 9 months. In some embodiments, lemborexant or salt thereof is administered to the subject for at least 12 months. In some embodiments, lemborexant or salt thereof is administered to the subject for at least 18 months. In some embodiments, lemborexant or salt thereof is administered to the subject for two years or more.

In some embodiments, the WASO2H is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to baseline. In some embodiments, the WASO2H is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 31 minutes, at least 32 minutes, at least 33 minutes, at least 34 minutes, at least 35 minutes, at least 36 minutes, at least 37 minutes, at least 38 minutes, at least 39 minutes, at least 40 minutes, at least 41 minutes, at least 42 minutes, at least 43 minutes, at least 44 minutes, or at least 45 minutes, relative to baseline.

In some embodiments, the WASO2H is reduced by at least 1 minute, relative to baseline. In some embodiments, the WASO2H is reduced by at least 2 minutes, relative to baseline. In some embodiments, the WASO2H is reduced by at least 3 minutes, relative to baseline. In some embodiments, the WASO2H is reduced by at least 4 minutes, relative to baseline. In some embodiments, the WASO2H is reduced by at least 5 minutes, relative to baseline. In some embodiments, the WASO2H is reduced by at least 6 minutes, relative to baseline. In some embodiments, the WASO2H is reduced by at least 7 minutes, relative to baseline. In some embodiments, the WASO2H is reduced by at least 8 minutes, relative to baseline. In some embodiments, the WASO2H is reduced by at least 9 minutes, relative to baseline. In some embodiments, the WASO2H is reduced by at least 10 minutes, relative to baseline.

In some embodiments, the WASO2H is reduced by at least 11 minutes, relative to baseline. In some embodiments, the WASO2H is reduced by at least 12 minutes, relative to baseline. In some embodiments, the WASO2H is reduced by at least 13 minutes, relative to baseline. In some embodiments, the WASO2H is reduced by at least 14 minutes, relative to baseline. In some embodiments, the WASO2H is reduced by at least 15 minutes, relative to baseline. In some embodiments, the WASO2H is reduced by at least 16 minutes, relative to baseline. In some embodiments, the WASO2H is reduced by at least 17 minutes, relative to baseline. In some embodiments, the WASO2H is reduced by at least 18 minutes, relative to baseline. In some embodiments, the WASO2H is reduced by at least 19 minutes, relative to baseline. In some embodiments, the WASO2H is reduced by at least 20 minutes, relative to baseline.

In some embodiments, the WASO2H is reduced by at least 21 minutes, relative to baseline. In some embodiments, the WASO2H is reduced by at least 22 minutes, relative to baseline. In some embodiments, the WASO2H is reduced by at least 23 minutes, relative to baseline. In some embodiments, the WASO2H is reduced by at least 24 minutes, relative to baseline. In some embodiments, the WASO2H is reduced by at least 25 minutes, relative to baseline. In some embodiments, the WASO2H is reduced by at least 26 minutes, relative to baseline. In some embodiments, the WASO2H is reduced by at least 27 minutes, relative to baseline. In some embodiments, the WASO2H is reduced by at least 28 minutes, relative to baseline. In some embodiments, the WASO2H is reduced by at least 29 minutes, relative to baseline.

In some embodiments, the WASO2H is reduced by at least 30 minutes, relative to baseline. In some embodiments, the WASO2H is reduced by at least 31 minutes, relative to baseline. In some embodiments, the WASO2H is reduced by at least 32 minutes, relative to baseline. In some embodiments, the WASO2H is reduced by at least 33 minutes, relative to baseline. In some embodiments, the WASO2H is reduced by at least 34 minutes, relative to baseline. In some embodiments, the WASO2H is reduced by at least 35 minutes, relative to baseline. In some embodiments, the WASO2H is reduced by at least 36 minutes, relative to baseline. In some embodiments, the WASO2H is reduced by at least 37 minutes, relative to baseline. In some embodiments, the WASO2H is reduced by at least 38 minutes, relative to baseline. In some embodiments, the WASO2H is reduced by at least 39 minutes, relative to baseline. In some embodiments, the WASO2H is reduced by at least 40 minutes, relative to baseline.

In some embodiments, the WASO2H is reduced by at least 41 minutes, relative to baseline. In some embodiments, the WASO2H is reduced by at least 42 minutes, relative to baseline. In some embodiments, the WASO2H is reduced by at least 43 minutes, relative to baseline. In some embodiments, the WASO2H is reduced by at least 44 minutes, relative to baseline. In some embodiments, the WASO2H is reduced by at least 45 minutes, relative to baseline.

In some embodiments, the WASO2H is reduced by about 1 minute, relative to baseline. In some embodiments, the WASO2H is reduced by about 2 minutes, relative to baseline. In some embodiments, the WASO2H is reduced by about 3 minutes, relative to baseline. In some embodiments, the WASO2H is reduced by about 4 minutes, relative to baseline. In some embodiments, the WASO2H is reduced by about 5 minutes, relative to baseline. In some embodiments, the WASO2H is reduced by about 6 minutes, relative to baseline. In some embodiments, the WASO2H is reduced by about 7 minutes, relative to baseline. In some embodiments, the WASO2H is reduced by about 8 minutes, relative to baseline. In some embodiments, the WASO2H is reduced by about 9 minutes, relative to baseline. In some embodiments, the WASO2H is reduced by about 10 minutes, relative to baseline.

In some embodiments, the WASO2H is reduced by about 11 minutes, relative to baseline. In some embodiments, the WASO2H is reduced by about 12 minutes, relative to baseline. In some embodiments, the WASO2H is reduced by about 13 minutes, relative to baseline. In some embodiments, the WASO2H is reduced by about 14 minutes, relative to baseline. In some embodiments, the WASO2H is reduced by about 15 minutes, relative to baseline. In some embodiments, the WASO2H is reduced by about 16 minutes, relative to baseline. In some embodiments, the WASO2H is reduced by about 17 minutes, relative to baseline. In some embodiments, the WASO2H is reduced by about 18 minutes, relative to baseline. In some embodiments, the WASO2H is reduced by about 19 minutes, relative to baseline. In some embodiments, the WASO2H is reduced by about 20 minutes, relative to baseline.

In some embodiments, the WASO2H is reduced by about 21 minutes, relative to baseline. In some embodiments, the WASO2H is reduced by about 22 minutes, relative to baseline. In some embodiments, the WASO2H is reduced by about 23 minutes, relative to baseline. In some embodiments, the WASO2H is reduced by about 24 minutes, relative to baseline. In some embodiments, the WASO2H is reduced by about 25 minutes, relative to baseline. In some embodiments, the WASO2H is reduced by about 26 minutes, relative to baseline. In some embodiments, the WASO2H is reduced by about 27 minutes, relative to baseline. In some embodiments, the WASO2H is reduced by about 28 minutes, relative to baseline. In some embodiments, the WASO2H is reduced by about 29 minutes, relative to baseline.

In some embodiments, the WASO2H is reduced by about 30 minutes, relative to baseline. In some embodiments, the WASO2H is reduced by about 31 minutes, relative to baseline. In some embodiments, the WASO2H is reduced by about 32 minutes, relative to baseline. In some embodiments, the WASO2H is reduced by about 33 minutes, relative to baseline. In some embodiments, the WASO2H is reduced by about 34 minutes, relative to baseline. In some embodiments, the WASO2H is reduced by about 35 minutes, relative to baseline. In some embodiments, the WASO2H is reduced by about 36 minutes, relative to baseline. In some embodiments, the WASO2H is reduced by about 37 minutes, relative to baseline. In some embodiments, the WASO2H is reduced by about 38 minutes, relative to baseline. In some embodiments, the WASO2H is reduced by about 39 minutes, relative to baseline. In some embodiments, the WASO2H is reduced by about 40 minutes, relative to baseline.

In some embodiments, the WASO2H is reduced by about 41 minutes, relative to baseline. In some embodiments, the WASO2H is reduced by about 42 minutes, relative to baseline. In some embodiments, the WASO2H is reduced by about 43 minutes, relative to baseline. In some embodiments, the WASO2H is reduced by about 44 minutes, relative to baseline. In some embodiments, the WASO2H is reduced by about 45 minutes, relative to baseline.

In some embodiments, 5 mg of lemborexant or an equivalent dose of a pharmaceutically acceptable salt thereof is administered to a subject and the WASO2H is reduced by about 27 minutes, relative to baseline. In some embodiments, 5 mg of lemborexant or an equivalent dose of a pharmaceutically acceptable salt thereof is administered to a subject and the WASO2H is reduced by about 30 minutes, relative to baseline.

In some embodiments, 5 mg of lemborexant or an equivalent dose of a pharmaceutically acceptable salt thereof is administered to a subject and the WASO2H is reduced by at least 27 minutes, relative to baseline. In some embodiments, 5 mg of lemborexant or an equivalent dose of a pharmaceutically acceptable salt thereof is administered to a subject and the WASO2H is reduced by at least 30 minutes, relative to baseline.

In some embodiments, 10 mg of lemborexant or an equivalent dose of a pharmaceutically acceptable salt thereof is administered to a subject and the WASO2H is reduced by about 28 minutes, relative to baseline. In some embodiments, 10 mg of lemborexant or an equivalent dose of a pharmaceutically acceptable salt thereof is administered to a subject and the WASO2H is reduced by about 37 minutes, relative to baseline.

In some embodiments, 10 mg of lemborexant or an equivalent dose of a pharmaceutically acceptable salt thereof is administered to a subject and the WASO2H is reduced by at least 28 minutes, relative to baseline. In some embodiments, 10 mg of lemborexant or an equivalent dose of a pharmaceutically acceptable salt thereof is administered to a subject and the sWASO2H is reduced by at least 37 minutes, relative to baseline.

In some embodiments, the WASO2H is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to placebo. In some embodiments, the WASO2H is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 31 minutes, at least 32 minutes, at least 33 minutes, at least 34 minutes, or at least 35 minutes, relative to placebo.

In some embodiments, the WASO2H is reduced by at least 1 minute, relative to placebo. In some embodiments, the WASO2H is reduced by at least 2 minutes, relative to placebo. In some embodiments, the WASO2H is reduced by at least 3 minutes, relative to placebo. In some embodiments, the WASO2H is reduced by at least 4 minutes, relative to placebo. In some embodiments, the WASO2H is reduced by at least 5 minutes, relative to placebo. In some embodiments, the WASO2H is reduced by at least 6 minutes, relative to placebo. In some embodiments, the WASO2H is reduced by at least 7 minutes, relative to placebo. In some embodiments, the WASO2H is reduced by at least 8 minutes, relative to placebo. In some embodiments, the WASO2H is reduced by at least 9 minutes, relative to placebo. In some embodiments, the WASO2H is reduced by at least 10 minutes, relative to placebo.

In some embodiments, the WASO2H is reduced by at least 11 minutes, relative to placebo. In some embodiments, the WASO2H is reduced by at least 12 minutes, relative to placebo. In some embodiments, the WASO2H is reduced by at least 13 minutes, relative to placebo. In some embodiments, the WASO2H is reduced by at least 14 minutes, relative to placebo. In some embodiments, the WASO2H is reduced by at least 15 minutes, relative to placebo. In some embodiments, the WASO2H is reduced by at least 16 minutes, relative to placebo. In some embodiments, the WASO2H is reduced by at least 17 minutes, relative to placebo. In some embodiments, the WASO2H is reduced by at least 18 minutes, relative to placebo. In some embodiments, the WASO2H is reduced by at least 19 minutes, relative to placebo. In some embodiments, the WASO2H is reduced by at least 20 minutes, relative to placebo.

In some embodiments, the WASO2H is reduced by at least 21 minutes, relative to placebo. In some embodiments, the WASO2H is reduced by at least 22 minutes, relative to placebo. In some embodiments, the WASO2H is reduced by at least 23 minutes, relative to placebo. In some embodiments, the WASO2H is reduced by at least 24 minutes, relative to placebo. In some embodiments, the WASO2H is reduced by at least 25 minutes, relative to placebo. In some embodiments, the WASO2H is reduced by at least 26 minutes, relative to placebo. In some embodiments, the WASO2H is reduced by at least 27 minutes, relative to placebo. In some embodiments, the WASO2H is reduced by at least 28 minutes, relative to placebo. In some embodiments, the WASO2H is reduced by at least 29 minutes, relative to placebo. In some embodiments, the WASO2H is reduced by at least 30 minutes, relative to placebo.

In some embodiments, the WASO2H is reduced by at least 31 minutes, relative to placebo. In some embodiments, the WASO2H is reduced by at least 32 minutes, relative to placebo. In some embodiments, the WASO2H is reduced by at least 33 minutes, relative to placebo. In some embodiments, the WASO2H is reduced by at least 34 minutes, relative to placebo. In some embodiments, the WASO2H is reduced by at least 35 minutes, relative to placebo.

In some embodiments, the WASO2H is reduced by about 1 minute, relative to placebo. In some embodiments, the WASO2H is reduced by about 2 minutes, relative to placebo. In some embodiments, the WASO2H is reduced by about 3 minutes, relative to placebo. In some embodiments, the WASO2H is reduced by about 4 minutes, relative to placebo. In some embodiments, the WASO2H is reduced by about 5 minutes, relative to placebo. In some embodiments, the WASO2H is reduced by about 6 minutes, relative to placebo. In some embodiments, the WASO2H is reduced by about 7 minutes, relative to placebo. In some embodiments, the WASO2H is reduced by about 8 minutes, relative to baseline. In some embodiments, the WASO2H is reduced by about 9 minutes, relative to baseline. In some embodiments, the WASO2H is reduced by about 10 minutes, relative to placebo.

In some embodiments, the WASO2H is reduced by about 11 minutes, relative to placebo. In some embodiments, the WASO2H is reduced by about 12 minutes, relative to placebo. In some embodiments, the WASO2H is reduced by about 13 minutes, relative to placebo. In some embodiments, the WASO2H is reduced by about 14 minutes, relative to placebo. In some embodiments, the WASO2H is reduced by about 15 minutes, relative to placebo. In some embodiments, the WASO2H is reduced by about 16 minutes, relative to placebo. In some embodiments, the WASO2H is reduced by about 17 minutes, relative to placebo. In some embodiments, the WASO2H is reduced by about 18 minutes, relative to placebo. In some embodiments, the WASO2H is reduced by about 19 minutes, relative to placebo. In some embodiments, the WASO2H is reduced by about 20 minutes, relative to placebo.

In some embodiments, the WASO2H is reduced by about 21 minutes, relative to placebo. In some embodiments, the WASO2H is reduced by about 22 minutes, relative to placebo. In some embodiments, the WASO2H is reduced by about 23 minutes, relative to placebo. In some embodiments, the WASO2H is reduced by about 24 minutes, relative to placebo. In some embodiments, the WASO2H is reduced by about 25 minutes, relative to placebo. In some embodiments, the WASO2H is reduced by about 26 minutes, relative to placebo. In some embodiments, the WASO2H is reduced by about 27 minutes, relative to placebo. In some embodiments, the WASO2H is reduced by about 28 minutes, relative to placebo. In some embodiments, the WASO2H is reduced by about 29 minutes, relative to placebo. In some embodiments, the WASO2H is reduced by about 30 minutes, relative to placebo.

In some embodiments, the WASO2H is reduced by about 31 minutes, relative to placebo. In some embodiments, the WASO2H is reduced by about 32 minutes, relative to placebo. In some embodiments, the WASO2H is reduced by about 33 minutes, relative to placebo. In some embodiments, the WASO2H is reduced by about 34 minutes, relative to placebo. In some embodiments, the WASO2H is reduced by about 35 minutes, relative to placebo.

In some embodiments, 5 mg of lemborexant or an equivalent dose of a pharmaceutically acceptable salt thereof is administered to a subject and the WASO2H is reduced by about 16 minutes, relative to placebo. In some embodiments, 5 mg of lemborexant or an equivalent dose of a pharmaceutically acceptable salt thereof is administered to a subject and the WASO2H is reduced by about 21 minutes, relative to placebo.

In some embodiments, 5 mg of lemborexant or an equivalent dose of a pharmaceutically acceptable salt thereof is administered to a subject and the WASO2H is reduced by at least 16 minutes, relative to placebo. In some embodiments, 5 mg of lemborexant or an equivalent dose of a pharmaceutically acceptable salt thereof is administered to a subject and the WASO2H is reduced by at least 21 minutes, relative to placebo.

In some embodiments, 10 mg of lemborexant or an equivalent dose of a pharmaceutically acceptable salt thereof is administered to a subject and the WASO2H is reduced by about 17 minutes, relative to placebo. In some embodiments, 10 mg of lemborexant or an equivalent dose of a pharmaceutically acceptable salt thereof is administered to a subject and the WASO2H is reduced by about 28 minutes, relative to placebo.

In some embodiments, 10 mg of lemborexant or an equivalent dose of a pharmaceutically acceptable salt thereof is administered to a subject and the WASO2H is reduced by at least 17 minutes, relative to placebo. In some embodiments, 10 mg of lemborexant or an equivalent dose of a pharmaceutically acceptable salt thereof is administered to a subject and the WASO2H is reduced by at least 28 minutes, relative to placebo.

In some embodiments, the WASO2H is reduced by at least 5 minutes, at least 10 minutes, at least 15 minutes, at least 30 minutes, at least 45 minutes, at least 60 minutes, at least 75 minutes, at least 90 minutes, at least 120 minutes, at least 150 minutes, or at least 180 minutes, relative to zolpidem. In some embodiments, the WASO2H is reduced by at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, relative to zolpidem.

In some embodiments, the WASO2H is reduced by at least 1 minute, relative to zolpidem. In some embodiments, the WASO2H is reduced by at least 2 minutes, relative to zolpidem. In some embodiments, the WASO2H is reduced by at least 3 minutes, relative to zolpidem. In some embodiments, the WASO2H is reduced by at least 4 minutes, relative to zolpidem. In some embodiments, the WASO2H is reduced by at least 5 minutes, relative to zolpidem. In some embodiments, the WASO2H is reduced by at least 6 minutes, relative to zolpidem. In some embodiments, the WASO2H is reduced by at least 7 minutes, relative to zolpidem. In some embodiments, the WASO2H is reduced by at least 8 minutes, relative to zolpidem. In some embodiments, the WASO2H is reduced by at least 9 minutes, relative to zolpidem. In some embodiments, the WASO2H is reduced by at least 10 minutes, relative to zolpidem.

In some embodiments, the WASO2H is reduced by at least 11 minutes, relative to zolpidem. In some embodiments, the WASO2H is reduced by at least 12 minutes, relative to zolpidem. In some embodiments, the WASO2H is reduced by at least 13 minutes, relative to zolpidem. In some embodiments, the WASO2H is reduced by at least 14 minutes, relative to zolpidem. In some embodiments, the WASO2H is reduced by at least 15 minutes, relative to zolpidem. In some embodiments, the WASO2H is reduced by at least 16 minutes, relative to zolpidem. In some embodiments, the WASO2H is reduced by at least 17 minutes, relative to zolpidem. In some embodiments, the WASO2H is reduced by at least 18 minutes, relative to zolpidem. In some embodiments, the WASO2H is reduced by at least 19 minutes, relative to zolpidem. In some embodiments, the WASO2H is reduced by at least 20 minutes, relative to zolpidem.

In some embodiments, the WASO2H is reduced by at least 21 minutes, relative to zolpidem. In some embodiments, the WASO2H is reduced by at least 22 minutes, relative to zolpidem. In some embodiments, the WASO2H is reduced by at least 23 minutes, relative to zolpidem. In some embodiments, the WASO2H is reduced by at least 24 minutes, relative to zolpidem. In some embodiments, the WASO2H is reduced by at least 25 minutes, relative to zolpidem.

In some embodiments, the WASO2H is reduced by about 1 minute, relative to zolpidem. In some embodiments, the WASO2H is reduced by about 2 minutes, relative to zolpidem. In some embodiments, the WASO2H is reduced by about 3 minutes, relative to zolpidem. In some embodiments, the WASO2H is reduced by about 4 minutes, relative to zolpidem. In some embodiments, the WASO2H is reduced by about 5 minutes, relative to zolpidem. In some embodiments, the WASO2H is reduced by about 6 minutes, relative to zolpidem. In some embodiments, the WASO2H is reduced by about 7 minutes, relative to zolpidem. In some embodiments, the WASO2H is reduced by about 8 minutes, relative to baseline. In some embodiments, the WASO2H is reduced by about 9 minutes, relative to baseline. In some embodiments, the WASO2H is reduced by about 10 minutes, relative to zolpidem.

In some embodiments, the WASO2H is reduced by about 11 minutes, relative to zolpidem. In some embodiments, the WASO2H is reduced by about 12 minutes, relative to zolpidem. In some embodiments, the WASO2H is reduced by about 13 minutes, relative to zolpidem. In some embodiments, the WASO2H is reduced by about 14 minutes, relative to zolpidem. In some embodiments, the WASO2H is reduced by about 15 minutes, relative to zolpidem. In some embodiments, the WASO2H is reduced by about 16 minutes, relative to zolpidem. In some embodiments, the WASO2H is reduced by about 17 minutes, relative to zolpidem. In some embodiments, the WASO2H is reduced by about 18 minutes, relative to zolpidem. In some embodiments, the WASO2H is reduced by about 19 minutes, relative to zolpidem. In some embodiments, the WASO2H is reduced by about 20 minutes, relative to zolpidem.

In some embodiments, the WASO2H is reduced by about 21 minutes, relative to zolpidem. In some embodiments, the WASO2H is reduced by about 22 minutes, relative to zolpidem. In some embodiments, the WASO2H is reduced by about 23 minutes, relative to zolpidem. In some embodiments, the WASO2H is reduced by about 24 minutes, relative to zolpidem. In some embodiments, the WASO2H is reduced by about 25 minutes, relative to zolpidem.

In some embodiments, 5 mg of lemborexant or an equivalent dose of a pharmaceutically acceptable salt thereof is administered to a subject and the WASO2H is reduced by about 6 minutes, relative to zolpidem.

In some embodiments, 5 mg of lemborexant or an equivalent dose of a pharmaceutically acceptable salt thereof is administered to a subject and the WASO2H is reduced by at least 6 minutes, relative to zolpidem.

In some embodiments, 10 mg of lemborexant or an equivalent dose of a pharmaceutically acceptable salt thereof is administered to a subject and the WASO2H is reduced by about 8 minutes, relative to zolpidem. In some embodiments, 10 mg of lemborexant or an equivalent dose of a pharmaceutically acceptable salt thereof is administered to a subject and the WASO2H is reduced by about 13 minutes, relative to zolpidem.

In some embodiments, 10 mg of lemborexant or an equivalent dose of a pharmaceutically acceptable salt thereof is administered to a subject and the WASO2H is reduced by at least 8 minutes, relative to zolpidem. In some embodiments, 10 mg of lemborexant or an equivalent dose of a pharmaceutically acceptable salt thereof is administered to a subject and the WASO2H is reduced by at least 13 minutes, relative to zolpidem.

In some embodiments, the subject has insomnia.

Methods of Improving Sleep Efficiency (SE)

Provided herein is a method of improving sleep efficiency (SE) in a subject comprising administering to the subject 5 mg or 10 mg of lemborexant or an equivalent dose of a pharmaceutically acceptable salt thereof.

In some embodiments, the SE is improved for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days. In some embodiments, the SE is improved for at least 1 day. In some embodiments, the SE is improved for at least 2 days. In some embodiments, the SE is improved for at least 3 days. In some embodiments, the SE is improved for at least 4 days. In some embodiments, the SE is improved for at least 5 days. In some embodiments, the SE is improved for at least 6 days. In some embodiments, the SE is improved for at least 7 days. In some embodiments, the SE is improved for at least 8 days. In some embodiments, the SE is improved for at least 9 days. In some embodiments, the SE is improved for at least 10 days.

In some embodiments, the SE is improved for at least 11 days. In some embodiments, the SE is improved for at least 12 days. In some embodiments, the SE is improved for at least 13 days. In some embodiments, the SE is improved for at least 14 days. In some embodiments, the SE is improved for at least 15 days. In some embodiments, the SE is improved for at least 16 days. In some embodiments, the SE is improved for at least 17 days. In some embodiments, the SE is improved for at least 18 days. In some embodiments, the SE is improved for at least 19 days.

In some embodiments, the SE is improved for at least 20 days. In some embodiments, the SE is improved for at least 21 days. In some embodiments, the SE is improved for at least 22 days. In some embodiments, the SE is improved for at least 23 days. In some embodiments, the SE is improved for at least 24 days. In some embodiments, the SE is improved for at least 25 days. In some embodiments, the SE is improved for at least 26 days. In some embodiments, the SE is improved for at least 27 days. In some embodiments, the SE is improved for at least 28 days. In some embodiments, the SE is improved for at least 29 days. In some embodiments, the SE is improved for at least 30 days.

In some embodiments, the SE is improved for at least one month. In some embodiments, the SE is improved for at least two months. In some embodiments, the SE is improved for at least three months. In some embodiments, the SE is improved for at least 6 months. In some embodiments, the SE is improved for at least 9 months. In some embodiments, the SE is improved for at least 12 months. In some embodiments, the SE is improved for at least 18 months. In some embodiments, the SE is improved for 2 years or more.

In some embodiments, the SE is improved for at least one month. In some embodiments, the SE is improved for at least two months, relative to baseline. In some embodiments, the SE is improved for at least three months, relative to baseline. In some embodiments, the SE is improved for at least 6 months, relative to baseline. In some embodiments, the SE is improved for at least 9 months, relative to baseline. In some embodiments, the SE is improved for at least 12 months, relative to baseline. In some embodiments, the SE is improved for at least 18 months, relative to baseline. In some embodiments, the SE is improved for 2 years or more, relative to baseline.

In some embodiments, lemborexant or salt thereof is administered to the subject for at least one month. In some embodiments, lemborexant or salt thereof is administered to the subject for at least two months. In some embodiments, lemborexant or salt thereof is administered to the subject for at least three months. In some embodiments, lemborexant or salt thereof is administered to the subject for at least 6 months. In some embodiments, lemborexant or salt thereof is administered to the subject for at least 9 months. In some embodiments, lemborexant or salt thereof is administered to the subject for at least 12 months. In some embodiments, lemborexant or salt thereof is administered to the subject for at least 18 months. In some embodiments, lemborexant or salt thereof is administered to the subject for two years or more.

In some embodiments, the SE is improved by at least 1%, at least 5%, at least 10%, at least 15%, at least 20%, at least 25%, at least 30%, at least 40%, or at least 50%, relative to baseline. In some embodiments, the SE is improved by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, or at least 25%, relative to baseline.

In some embodiments, the SE is improved by at least 1%, relative to baseline. In some embodiments, the SE is improved by at least 2%, relative to baseline. In some embodiments, the SE is improved by at least 3%, relative to baseline. In some embodiments, the SE is improved by at least 4%, relative to baseline. In some embodiments, the SE is improved by at least 5%, relative to baseline. In some embodiments, the SE is improved by at least 6%, relative to baseline. In some embodiments, the SE is improved by at least 7%, relative to baseline. In some embodiments, the SE is improved by at least 8%, relative to baseline. In some embodiments, the SE is improved by at least 9%, relative to baseline.

In some embodiments, the SE is improved by at least 10%, relative to baseline. In some embodiments, the SE is improved by at least 11%, relative to baseline. In some embodiments, the SE is improved by at least 12%, relative to baseline. In some embodiments, the SE is improved by at least 13%, relative to baseline. In some embodiments, the SE is improved by at least 14%, relative to baseline. In some embodiments, the SE is improved by at least 15%, relative to baseline. In some embodiments, the SE is improved by at least 16%, relative to baseline. In some embodiments, the SE is improved by at least 17%, relative to baseline. In some embodiments, the SE is improved by at least 18%, relative to baseline. In some embodiments, the SE is improved by at least 19%, relative to baseline.

In some embodiments, the SE is improved by at least 20%, relative to baseline. In some embodiments, the SE is improved by at least 21%, relative to baseline. In some embodiments, the SE is improved by at least 22%, relative to baseline. In some embodiments, the SE is improved by at least 23%, relative to baseline. In some embodiments, the SE is improved by at least 24%, relative to baseline. In some embodiments, the SE is improved by at least 25%, relative to baseline.

In some embodiments, the SE is improved by about 1%, relative to baseline. In some embodiments, the SE is improved by about 2%, relative to baseline. In some embodiments, the SE is improved by about 3%, relative to baseline. In some embodiments, the SE is improved by about 4%, relative to baseline. In some embodiments, the SE is improved by about 5%, relative to baseline. In some embodiments, the SE is improved by about 6%, relative to baseline. In some embodiments, the SE is improved by about 7%, relative to baseline. In some embodiments, the SE is improved by about 8%, relative to baseline. In some embodiments, the SE is improved by about 9%, relative to baseline.

In some embodiments, the SE is improved by about 10%, relative to baseline. In some embodiments, the SE is improved by about 11%, relative to baseline. In some embodiments, the SE is improved by about 12%, relative to baseline. In some embodiments, the SE is improved by about 13%, relative to baseline. In some embodiments, the SE is improved by about 14%, relative to baseline. In some embodiments, the SE is improved by about 15%, relative to baseline. In some embodiments, the SE is improved by about 16%, relative to baseline. In some embodiments, the SE is improved by about 17%, relative to baseline. In some embodiments, the SE is improved by about 18%, relative to baseline. In some embodiments, the SE is improved by about 19%, relative to baseline.

In some embodiments, the SE is improved by about 20%, relative to baseline. In some embodiments, the SE is improved by about 21%, relative to baseline. In some embodiments, the SE is improved by about 22%, relative to baseline. In some embodiments, the SE is improved by about 23%, relative to baseline. In some embodiments, the SE is improved by about 24%, relative to baseline. In some embodiments, the SE is improved by about 25%, relative to baseline.

In some embodiments, 5 mg of lemborexant or an equivalent dose of a pharmaceutically acceptable salt thereof is administered to a subject and the SE is improved by at least 12%, relative to baseline.

In some embodiments, 5 mg of lemborexant or an equivalent dose of a pharmaceutically acceptable salt thereof is administered to a subject and the SE is improved by about 12%, relative to baseline.

In some embodiments, 10 mg of lemborexant or an equivalent dose of a pharmaceutically acceptable salt thereof is administered to a subject and the SE is improved by at least 14%, relative to baseline. In some embodiments, 10 mg of lemborexant or an equivalent dose of a pharmaceutically acceptable salt thereof is administered to a subject and the SE is improved by at least 15%, relative to baseline.

In some embodiments, 10 mg of lemborexant or an equivalent dose of a pharmaceutically acceptable salt thereof is administered to a subject and the SE is improved by about 14%, relative to baseline. In some embodiments, 10 mg of lemborexant or an equivalent dose of a pharmaceutically acceptable salt thereof is administered to a subject and the SE is improved by about 15%, relative to baseline.

In some embodiments, the SE is improved by at least 1%, at least 5%, at least 10%, at least 15%, at least 20%, at least 25%, at least 30%, at least 40%, or at least 50%, relative to placebo. In some embodiments, the SE is improved by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, or at least 25%, relative to placebo.

In some embodiments, the SE is improved by at least 1%, relative to placebo. In some embodiments, the SE is improved by at least 2%, relative to placebo. In some embodiments, the SE is improved by at least 3%, relative to placebo. In some embodiments, the SE is improved by at least 4%, relative to placebo. In some embodiments, the SE is improved by at least 5%, relative to placebo.

In some embodiments, the SE is improved by at least 6%, relative to placebo. In some embodiments, the SE is improved by at least 7%, relative to placebo. In some embodiments, the SE is improved by at least 8%, relative to placebo. In some embodiments, the SE is improved by at least 9%, relative to placebo. In some embodiments, the SE is improved by at least 10%, relative to placebo.

In some embodiments, the SE is improved by at least 11%, relative to placebo. In some embodiments, the SE is improved by at least 12%, relative to placebo. In some embodiments, the SE is improved by at least 13%, relative to placebo. In some embodiments, the SE is improved by at least 14%, relative to placebo. In some embodiments, the SE is improved by at least 15%, relative to placebo.

In some embodiments, the SE is improved by at least 16%, relative to placebo. In some embodiments, the SE is improved by at least 17%, relative to placebo. In some embodiments, the SE is improved by at least 18%, relative to placebo. In some embodiments, the SE is improved by at least 19%, relative to placebo. In some embodiments, the SE is improved by at least 20%, relative to placebo.

In some embodiments, the SE is improved by at least 21%, relative to placebo. In some embodiments, the SE is improved by at least 22%, relative to placebo. In some embodiments, the SE is improved by at least 23%, relative to placebo. In some embodiments, the SE is improved by at least 24%, relative to placebo. In some embodiments, the SE is improved by at least 25%, relative to placebo.

In some embodiments, the SE is improved by about 1%, relative to placebo. In some embodiments, the SE is improved by about 2%, relative to placebo. In some embodiments, the SE is improved by about 3%, relative to placebo. In some embodiments, the SE is improved by about 4%, relative to placebo. In some embodiments, the SE is improved by about 5%, relative to placebo.

In some embodiments, the SE is improved by about 6%, relative to placebo. In some embodiments, the SE is improved by about 7%, relative to placebo. In some embodiments, the SE is improved by about 8%, relative to placebo. In some embodiments, the SE is improved by about 9%, relative to placebo. In some embodiments, the SE is improved by about 10%, relative to placebo.

In some embodiments, the SE is improved by about 11%, relative to placebo. In some embodiments, the SE is improved by about 12%, relative to placebo. In some embodiments, the SE is improved by about 13%, relative to placebo. In some embodiments, the SE is improved by about 14%, relative to placebo. In some embodiments, the SE is improved by about 15%, relative to placebo.

In some embodiments, the SE is improved by about 16%, relative to placebo. In some embodiments, the SE is improved by about 17%, relative to placebo. In some embodiments, the SE is improved by about 18%, relative to placebo. In some embodiments, the SE is improved by about 19%, relative to placebo. In some embodiments, the SE is improved by about 20%, relative to placebo.

In some embodiments, the SE is improved by about 21%, relative to placebo. In some embodiments, the SE is improved by about 22%, relative to placebo. In some embodiments, the SE is improved by about 23%, relative to placebo. In some embodiments, the SE is improved by about 24%, relative to placebo. In some embodiments, the SE is improved by about 25%, relative to placebo.

In some embodiments, 5 mg of lemborexant or an equivalent dose of a pharmaceutically acceptable salt thereof is administered to a subject and the SE is improved by at least 7%, relative to placebo. In some embodiments, 5 mg of lemborexant or an equivalent dose of a pharmaceutically acceptable salt thereof is administered to a subject and the SE is improved by at least 9%, relative to placebo.

In some embodiments, 5 mg of lemborexant or an equivalent dose of a pharmaceutically acceptable salt thereof is administered to a subject and the SE is improved by about 7%, relative to placebo. In some embodiments, 5 mg of lemborexant or an equivalent dose of a pharmaceutically acceptable salt thereof is administered to a subject and the SE is improved by at about 9%, relative to placebo.

In some embodiments, 10 mg of lemborexant or an equivalent dose of a pharmaceutically acceptable salt thereof is administered to a subject and the SE is improved by at least 8%, relative to placebo. In some embodiments, 10 mg of lemborexant or an equivalent dose of a pharmaceutically acceptable salt thereof is administered to a subject and the SE is improved by at least 8%, relative to placebo.

In some embodiments, 10 mg of lemborexant or an equivalent dose of a pharmaceutically acceptable salt thereof is administered to a subject and the SE is improved by about 8%, relative to placebo. In some embodiments, 10 mg of lemborexant or an equivalent dose of a pharmaceutically acceptable salt thereof is administered to a subject and the SE is improved by about 11%, relative to placebo.

In some embodiments, the SE is improved by at least 1%, at least 5%, at least 10%, at least 15%, at least 20%, at least 25%, at least 30%, at least 40%, or at least 50%, relative to zolpidem. In some embodiments, the SE is improved by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15, relative to zolpidem.

In some embodiments, the SE is improved by at least 1%, relative to zolpidem. In some embodiments, the SE is improved by at least 2%, relative to zolpidem. In some embodiments, the SE is improved by at least 3%, relative to zolpidem. In some embodiments, the SE is improved by at least 4%, relative to zolpidem. In some embodiments, the SE is improved by at least 5%, relative to zolpidem.

In some embodiments, the SE is improved by at least 6%, relative to zolpidem. In some embodiments, the SE is improved by at least 7%, relative to zolpidem. In some embodiments, the SE is improved by at least 8%, relative to zolpidem. In some embodiments, the SE is improved by at least 9%, relative to zolpidem. In some embodiments, the SE is improved by at least 10%, relative to zolpidem.

In some embodiments, the SE is improved by at least 11%, relative to zolpidem. In some embodiments, the SE is improved by at least 12%, relative to zolpidem. In some embodiments, the SE is improved by at least 13%, relative to zolpidem. In some embodiments, the SE is improved by at least 14%, relative to zolpidem. In some embodiments, the SE is improved by at least 15%, relative to zolpidem.

In some embodiments, the SE is improved by about 1%, relative to zolpidem. In some embodiments, the SE is improved by about 2%, relative to zolpidem. In some embodiments, the SE is improved by about 3%, relative to zolpidem. In some embodiments, the SE is improved by about 4%, relative to zolpidem. In some embodiments, the SE is improved by about 5%, relative to zolpidem.

In some embodiments, the SE is improved by about 6%, relative to zolpidem. In some embodiments, the SE is improved by about 7%, relative to zolpidem. In some embodiments, the SE is improved by about 8%, relative to zolpidem. In some embodiments, the SE is improved by about 9%, relative to zolpidem. In some embodiments, the SE is improved by about 10%, relative to zolpidem.

In some embodiments, the SE is improved by about 11%, relative to zolpidem. In some embodiments, the SE is improved by about 12%, relative to zolpidem. In some embodiments, the SE is improved by about 13%, relative to zolpidem. In some embodiments, the SE is improved by about 14%, relative to zolpidem. In some embodiments, the SE is improved by about 15%, relative to zolpidem.

In some embodiments, 5 mg of lemborexant or an equivalent dose of a pharmaceutically acceptable salt thereof is administered to a subject and the SE is improved by at least 2%, relative to zolpidem. In some embodiments, 5 mg of lemborexant or an equivalent dose of a pharmaceutically acceptable salt thereof is administered to a subject and the SE is improved by at least 3%, relative to zolpidem.

In some embodiments, 5 mg of lemborexant or an equivalent dose of a pharmaceutically acceptable salt thereof is administered to a subject and the SE is improved by about 2%, relative to zolpidem. In some embodiments, 5 mg of lemborexant or an equivalent dose of a pharmaceutically acceptable salt thereof is administered to a subject and the SE is improved by at about 4%, relative to zolpidem.

In some embodiments, 10 mg of lemborexant or an equivalent dose of a pharmaceutically acceptable salt thereof is administered to a subject and the SE is improved by at least 4%, relative to zolpidem.

In some embodiments, 10 mg of lemborexant or an equivalent dose of a pharmaceutically acceptable salt thereof is administered to a subject and the SE is improved by about 4%, relative to zolpidem. In some embodiments, 10 mg of lemborexant or an equivalent dose of a pharmaceutically acceptable salt thereof is administered to a subject and the SE is improved by about 5%, relative to zolpidem.

Other Embodiments

Embodiment 1. A method of reducing subjective sleep onset latency (sSOL) in a subject comprising administering to the subject 5 mg or 10 mg of lemborexant or an equivalent dose of a pharmaceutically acceptable salt thereof, wherein the sSOL is reduced, relative to baseline, for at least one month.

Embodiment 2. The method according to embodiment 1, wherein the sSOL is reduced, relative to baseline, for at least six months.

Embodiment 3. The method according to embodiment 1, wherein lemborexant or salt thereof is administered to the subject for at least one month.

Embodiment 4. The method according to embodiment 2, wherein lemborexant or salt thereof is administered to the subject for at least six months.

Embodiment 5. The method according to embodiment 1, wherein the sSOL is reduced by at least 20 minutes.

Embodiment 6. The method according to embodiment 1, wherein the sSOL is 40 minutes or less.

Embodiment 7. The method according to embodiment 6, wherein the sSOL is 25 minutes or less.

Embodiment 8. The method according to embodiment 1, wherein the subject has insomnia.

Embodiment 9. A method of improving subjective sleep efficiency (sSE) in a subject comprising administering to the subject 5 mg or 10 mg of lemborexant or an equivalent dose of a pharmaceutically acceptable salt thereof, wherein the sSE is increased, relative to baseline, for at least one month.

Embodiment 10. The method according to embodiment 9, wherein the sSE is increased, relative to baseline, for at least six months.

Embodiment 11. The method according to embodiment 9, wherein lemborexant or salt thereof is administered to the subject for at least one month.

Embodiment 12. The method according to embodiment 10, wherein lemborexant or salt thereof is administered to the subject for at least six months.

Embodiment 13. The method according to embodiment 9, wherein the sSE is improved by at least 13%.

Embodiment 14. The method according to embodiment 9, wherein the subject has insomnia.

Embodiment 15. A method of reducing subjective wake after sleep onset (sWASO) in a subject comprising administering to the subject 5 mg or 10 mg of lemborexant or an equivalent dose of a pharmaceutically acceptable salt thereof, wherein the sWASO is reduced, relative to baseline, for at least one month.

Embodiment 16. The method according to embodiment 15, wherein the sWASO is reduced, relative to baseline, for at least six months.

Embodiment 17. The method according to embodiment 15, wherein lemborexant or salt thereof is administered to the subject for at least one month.

Embodiment 18. The method according to embodiment 16, wherein lemborexant or salt thereof is administered to the subject for at least six months.

Embodiment 19. The method according to embodiment 15, wherein the sWASO is reduced by at least 40 minutes.

Embodiment 20. The method according to embodiment 15, wherein the subject has insomnia.

Embodiment 21. Lemborexant or a pharmaceutically acceptable salt thereof for use in reducing subjective sleep onset latency (sSOL) in a subject, comprising administering to the subject 5 mg or 10 mg of lemborexant or an equivalent dose of pharmaceutically acceptable salt thereof, wherein the sSOL is reduced, relative to baseline, for at least one month.

Embodiment 22. The use according to embodiment 21, wherein the sSOL is reduced, relative to baseline, for at least six months.

Embodiment 23. The use according to embodiment 21, wherein lemborexant or salt thereof is administered to the subject for at least one month.

Embodiment 24. The use according to embodiment 22, wherein lemborexant or salt thereof is administered to the subject for at least six months.

Embodiment 25. The use according to embodiment 21, wherein the sSOL is reduced by at least 20 minutes.

Embodiment 26. The use according to embodiment 21, wherein the subject has insomnia.

Embodiment 27. Lemborexant or pharmaceutically acceptable salt thereof for improving subjective sleep efficiency (sSE) in a subject, comprising administering to the subject 5 mg or 10 mg of lemborexant or an equivalent dose of pharmaceutically acceptable salt thereof, wherein the sSE is increased, relative to baseline, for at least one month.

Embodiment 28. The use according to embodiment 27, wherein the sSE is increased, relative to baseline, for at least six months.

Embodiment 29. The use according to embodiment 27, wherein lemborexant or salt thereof is administered to the subject for at least one month.

Embodiment 30. The use according to embodiment 28, wherein lemborexant or salt thereof is administered to the subject for at least six months.

Embodiment 31. The use according to embodiment 27, wherein the sSE is improved by at least 13%.

Embodiment 32. The use according to embodiment 27, wherein the subject has insomnia.

Embodiment 33. Lemborexant or pharmaceutically acceptable salt thereof for reducing subjective wake after sleep onset (sWASO) in a subject, comprising administering to the subject 5 mg or 10 mg of lemborexant or an equivalent dose of pharmaceutically acceptable salt thereof, wherein the sWASO is reduced, relative to baseline, for at least one month.

Embodiment 34. The use according to embodiment 33, wherein the sWASO is reduced, relative to baseline, for at least six months.

Embodiment 35. The use according to embodiment 33, wherein lemborexant or salt thereof is administered to the subject for at least one month.

Embodiment 36. The use according to embodiment 34, wherein lemborexant or salt thereof is administered to the subject for at least six months.

Embodiment 37. The use according to embodiment 33, wherein the sWASO is reduced by at least 40 minutes.

Embodiment 38. The use according to embodiment 33, wherein the subject has insomnia.

Embodiment 39. A method for treating insomnia, comprising administering orally a dosage form comprising lemborexant or a pharmaceutically acceptable salt thereof at a single daily dose ranging from about 5 to 10 mg, wherein the dosage form is achievable on maintaining reduction a time to sleep onset in Subjective Sleep Onset Latency (sSOL) compared to placebo during the treatment for at least one month.

Embodiment 40. A method for treating insomnia, comprising administering orally a dosage form comprising lemborexant or a pharmaceutically acceptable salt thereof at a single daily dose ranging from about 5 to 10 mg, wherein the dosage form is achievable on maintaining reduction a time to sleep onset in Subjective Sleep Onset Latency (sSOL) compared to placebo during the treatment through six months.

Embodiment 41. A method for treating insomnia, comprising administering orally a dosage form comprising lemborexant or a pharmaceutically acceptable salt thereof at a single daily dose ranging from about 5 to 10 mg, wherein the dosage form may be administered to a patient for at least one month, and wherein the dosage form is achievable on maintaining reduction a time to sleep onset in Subjective Sleep Onset Latency (sSOL) compared to placebo during the treatment for at least one month.

Embodiment 42. A method for treating insomnia, comprising administering orally a dosage form comprising lemborexant or a pharmaceutically acceptable salt thereof at a single daily dose ranging from about 5 to 10 mg, wherein the dosage form may be administered to a patient for six months, and wherein the dosage form is achievable on maintaining reduction a time to sleep onset in Subjective Sleep Onset Latency (sSOL) compared to placebo during the treatment through six months.

Embodiment 43. A method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of sleep efficiency in Subjective Sleep Efficiency (sSE) compared to placebo during the treatment for at least one month.

Embodiment 44. A method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of sleep efficiency in Subjective Sleep Efficiency (sSE) compared to placebo during the treatment through six months.

Embodiment 45. A method for treating insomnia, comprising administering orally a dosage form comprising lemborexant or a pharmaceutically acceptable salt thereof at a single daily dose ranging from about 5 to 10 mg, wherein the dosage form may be administered to a patient for at least one month, and wherein the dosage form is achievable on maintaining improvement of sleep efficiency in Subjective Sleep Efficiency (sSE) compared to placebo during the treatment for at least one month.

Embodiment 46. A method for treating insomnia, comprising administering orally a dosage form comprising lemborexant or a pharmaceutically acceptable salt thereof at a single daily dose ranging from about 5 to 10 mg, wherein the dosage form may be administered to a patient for six months, and wherein the dosage form is achievable on maintaining improvement of sleep efficiency in Subjective Sleep Efficiency (sSE) compared to placebo during the treatment through six months.

Embodiment 47. A method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of Wake After Sleep Onset (sWASO) compared to placebo during the treatment for at least one month.

Embodiment 48. A method for treating insomnia, comprising administering orally a dosage form comprising lemborexant or a pharmaceutically acceptable salt thereof at a single daily dose ranging from about 5 to 10 mg, wherein the dosage form is achievable on maintaining improvement of Wake After Sleep Onset (sWASO) compared to placebo during the treatment through six months.

Embodiment 49. A method for treating insomnia, comprising administering orally a dosage form comprising lemborexant or a pharmaceutically acceptable salt thereof at a single daily dose ranging from about 5 to 10 mg, wherein the dosage form may be administered to a patient for at least one month, and wherein the dosage form is achievable on maintaining improvement of Wake After Sleep Onset (sWASO) compared to placebo during the treatment for at least one month.

Embodiment 50. A method for treating insomnia, comprising administering orally a dosage form comprising lemborexant or a pharmaceutically acceptable salt thereof at a single daily dose ranging from about 5 to 10 mg, wherein the dosage form may be administered to a patient for six months, and wherein the dosage form is achievable on maintaining improvement of Wake After Sleep Onset (sWASO) compared to placebo during the treatment through six months.

Embodiment 51. A method for treating insomnia in a subject comprising administering to the subject 5 mg or 10 mg of lemborexant or an equivalent dose of a pharmaceutically acceptable salt thereof, wherein subjective sleep onset latency is reduced, relative to baseline, for at least one month.

Embodiment 52. A method for treating insomnia in a subject comprising administering to the subject 5 mg or 10 mg of lemborexant or an equivalent dose of a pharmaceutically acceptable salt thereof, wherein subjective sleep efficiency is increased, relative to baseline, for at least one month.

Embodiment 53. A method for treating insomnia in a subject comprising administering to the subject 5 mg or 10 mg of lemborexant or an equivalent dose of a pharmaceutically acceptable salt thereof, wherein subjective wake after sleep onset is reduced, relative to baseline, for at least one month.

Embodiment 54. A method of identifying a subject responsive to treatment with lemborexant or a pharmaceutically acceptable salt thereof, comprising:

a) determining a pre-treatment period subjective wake after sleep onset (sWASO) of the subject;
b) administering to the subject 5 mg or 10 mg of lemborexant or an equivalent dose of a pharmaceutically acceptable salt thereof for a treatment period if the pre-treatment period sWASO is 60 minutes or more;
c) determining the post-treatment period sWASO of the subject;
d) administering to the subject 5 mg or 10 mg of lemborexant or an equivalent dose of a pharmaceutically acceptable salt thereof if the post-treatment period sWASO is less than 60 minutes and the post-treatment period sWASO is 10 or more minutes less than the pre-treatment period sWASO.

Embodiment 55. The method according to embodiment 54, wherein the post-treatment period sWASO is at least 20 minutes less than the pre-treatment period sWASO.

Embodiment 56. The method according to embodiment 54, wherein the post-treatment period sWASO is at least 30 minutes less than the pre-treatment period sWASO.

Embodiment 57. The method according to embodiment 54, wherein, prior to administering lemborexant or a pharmaceutically acceptable salt thereof, a pre-treatment period subjective sleep efficiency (sSE) is determined.

Embodiment 58. The method according to embodiment 57, wherein, after administering lemborexant or a pharmaceutically acceptable salt thereof, a post-treatment period sSE is determined.

Embodiment 59. The method according to embodiment 55, wherein the post-treatment period sSE is improved by at least 10% relative to the pre-treatment period sSE.

Embodiment 60. The method according to embodiment 55, wherein the post-treatment period sSE is improved by at least 14% relative to the pre-treatment period sSE.

Embodiment 61. The method according to embodiment 54, wherein, prior to administering lemborexant or a pharmaceutically acceptable salt thereof, a pre-treatment period subjective sleep onset latency (sSOL) is determined.

Embodiment 62. The method according to embodiment 61, wherein, after administering lemborexant or a pharmaceutically acceptable salt thereof, a post-treatment period sSOL is determined.

Embodiment 63. The method according to embodiment 62, wherein the post-treatment period sSOL is at least 15 minutes less than the pre-treatment period sSOL.

Embodiment 64. The method according to embodiment 62, wherein the post-treatment period sSOL is at least 20 minutes less than the pre-treatment period sSOL.

Embodiment 65. A method for treating insomnia in a subject in need thereof, comprising:

a) determining a pre-treatment period subjective sleep onset latency (sSOL) of the subject;
b) administering to the subject an oral dosage form comprising 5 mg of lemborexant or an equivalent dose of a pharmaceutically acceptable salt thereof 15 minutes or less before a bedtime of the subject, wherein the subject remains in bed for at least 7 hours;
c) determining a post-treatment period sSOL of the subject;
d) administering to the subject an oral dosage form comprising 10 mg of lemborexant or an equivalent dose of a pharmaceutically acceptable salt thereof 15 minutes or less before a bedtime of the subject if the post-treatment sSOL is not reduced, relative to the pre-treatment period sSOL and the subject does not experience a serious adverse reaction, wherein the subject remains in bed for at least 7 hours;

wherein the post-treatment period sSOL is reduced, relative to the pre-treatment period sSOL, for at least one month, and wherein the post-treatment period sSOL is reduced by 15 minutes or more relative to the pre-treatment period sSOL.

Embodiment 66. The method according to embodiment 65, wherein the post-treatment period sSOL is reduced by 20 minutes or more relative to the pre-treatment period sSOL.

Embodiment 67. The method according to embodiment 65, wherein the post-treatment period sSOL is 40 minutes or less.

Embodiment 68. The method according to embodiment 67, wherein the post-treatment period sSOL is 25 minutes or less.

Embodiment 69. A method for treating insomnia in a subject in need thereof, comprising:

a) determining a pre-treatment period subjective sleep efficiency (sSE) of the subject;
b) administering to the subject an oral dosage form comprising 5 mg of lemborexant or an equivalent dose of a pharmaceutically acceptable salt thereof 15 minutes or less before a bedtime of the subject, wherein the subject remains in bed for at least 7 hours;

c) determining a post-treatment period sSE of the subject;

d) administering to the subject an oral dosage form comprising 10 mg of lemborexant or an equivalent dose of a pharmaceutically acceptable salt thereof 15 minutes or less before a bedtime of the subject if the post-treatment sSOL is not increased, relative to the pre-treatment period sSE and the subject does not experience a serious adverse reaction, wherein the subject remains in bed for at least 7 hours;

wherein the post-treatment period sSE is increased relative to the pre-treatment period sSE, for at least one month, and wherein the post-treatment period sSE is increased by 8% or more relative to the pre-treatment period sSE.

Embodiment 70. The method according to embodiment 69, wherein the post-treatment period sSE is increased by 13% or more relative to the pre-treatment period sSE.

Embodiment 71. A method for treating insomnia in a subject in need thereof, comprising:

a) determining a pre-treatment period subjective wake after sleep onset (sWASO) of the subject;

b) administering to the subject an oral dosage form comprising 5 mg of lemborexant or an equivalent dose of a pharmaceutically acceptable salt thereof 15 minutes or less before a bedtime of the subject, wherein the subject remains in bed for at least 7 hours;

c) determining a post-treatment period sWASO of the subject;

d) administering to the subject an oral dosage form comprising 10 mg of lemborexant or an equivalent dose of a pharmaceutically acceptable salt thereof 15 minutes or less before a bedtime of the subject if the post-treatment sSOL is not reduced, relative to the pre-treatment period sWASO and the subject does not experience a serious adverse reaction, wherein the subject remains in bed for at least 7 hours;

wherein the post-treatment period sWASO is reduced, relative to the pre-treatment period sWASO, for at least one month, and wherein the post-treatment period sWASO is reduced by at least 29 minutes relative to the pre-treatment period sWASO.

Embodiment 72. The method according to embodiment 71, wherein the post-treatment period sWASO is reduced by at least 40 minutes relative to the pre-treatment period sWASO.

Embodiment 73. A method for treating insomnia, comprising administering orally a dosage form comprising 5 mg or 10 mg of lemborexant or an equivalent dose of a pharmaceutically acceptable salt thereof, wherein the method comprising orally administering the 5 mg dose of lemborexant or a pharmaceutically acceptable salt thereof to a patient no more than once per night and within a few minutes before going to bed, with at least 7 hours remaining before the planned time of awakening, wherein if the 5 mg dose is well tolerated but not effective, then the dose can be increased to 10 mg once daily, wherein the dosage form is achievable on maintaining reduction a time to sleep onset in subjective Sleep Onset Latency (sSOL) during a treatment for at least one month, and wherein the sSOL is reduced by at least 15 minutes relative to baseline.

Embodiment 74. A method for treating insomnia, comprising administering orally a dosage form comprising 5 mg or 10 mg of lemborexant or an equivalent dose of a pharmaceutically acceptable salt thereof, wherein the method comprising orally administering the 5 mg dose of lemborexant or a pharmaceutically acceptable salt thereof to a patient no more than once per night and within a few minutes before going to bed, with at least 7 hours remaining before the planned time of awakening, wherein if the 5 mg dose is well tolerated but not effective, then the dose can be increased to 10 mg once daily, wherein the dosage form is achievable on maintaining improvement of sleep efficiency in subjective Sleep Efficiency (sSE) during a treatment for at least one month, and wherein the sSE is improved by at least 4% relative to baseline.

Embodiment 75. A method for treating insomnia, comprising administering orally a dosage form comprising 5 mg or 10 mg of lemborexant or an equivalent dose of a pharmaceutically acceptable salt thereof, wherein the method comprising orally administering the 5 mg dose of lemborexant or a pharmaceutically acceptable salt thereof to a patient no more than once per night and within a few minutes before going to bed, with at least 7 hours remaining before the planned time of awakening, wherein if the 5 mg dose is well tolerated but not effective, then the dose can be increased to 10 mg once daily, wherein the dosage form is achievable on maintaining improvement of subjective Wake After Sleep Onset (sWASO) during a treatment for at least one month, and wherein the sWASO is reduced by at least 29 minutes relative to baseline.

Embodiment 76. A method for treating insomnia, comprising administering orally a dosage form comprising 5 mg or 10 mg of lemborexant or an equivalent dose of a pharmaceutically acceptable salt thereof, wherein the method comprises administering orally the 5 mg dose of lemborexant or a pharmaceutically acceptable salt thereof to a patient no more than once per night, immediately before going to bed, with at least 7 hours remaining before the planned time of awakening, wherein the daily dose can be increased to 10 mg based on clinical response and tolerability, wherein the dosage form is achievable on maintaining reduction a time to sleep onset in subjective Sleep Onset Latency (sSOL) during a treatment for at least one month.

Embodiment 77. The method according to Embodiment 76, wherein the dosage form is achievable on maintaining reduction a time to sleep onset in subjective Sleep Onset Latency (sSOL) during a treatment for at least six months.

Embodiment 78. The method according to Embodiment 76, wherein the dosage form may be administered to the patient for at least one month.

Embodiment 79. The method according to Embodiment 76, wherein the dosage form may be administered to the patient for at least six months.

Embodiment 80. The method according to Embodiment 76, wherein the sSOL is reduced by at least 15 minutes relative to baseline.

Embodiment 81. A method for treating insomnia, comprising administering orally a dosage form comprising 5 mg or 10 mg of lemborexant or an equivalent dose of a pharmaceutically acceptable salt thereof, wherein the method comprises administering orally the 5 mg dose of lemborexant or a pharmaceutically acceptable salt thereof to a patient no more than once per night, immediately before going to bed, with at least 7 hours remaining before the planned time of awakening, wherein the daily dose may be increased to 10 mg based on clinical response and tolerability, wherein the dosage form is achievable on maintaining improvement of sleep efficiency in subjective Sleep Efficiency (sSE) during a treatment for at least one month.

Embodiment 82. The method according to Embodiment 81, the dosage form is achievable on maintaining improvement of sleep efficiency in subjective Sleep Efficiency (sSE) during a treatment for at least one month.

Embodiment 83. The method according to Embodiment 81, wherein the dosage form may be administered to the patient for at least one month.

Embodiment 84. The method according to Embodiment 81, wherein the dosage form may be administered to the patient for at least six months.

Embodiment 85. The method according to Embodiment 81, wherein the sSE is improved by at least 4% relative to baseline.

Embodiment 86. A method for treating insomnia, comprising administering orally a dosage form comprising 5 mg or 10 mg of lemborexant or an equivalent dose of a pharmaceutically acceptable salt thereof, wherein the method comprises administering orally the 5 mg dose of lemborexant or a pharmaceutically acceptable salt thereof to a patient no more than once per night, immediately before going to bed, with at least 7 hours remaining before the planned time of awakening, wherein the daily dose may be increased to 10 mg based on clinical response and tolerability, wherein the dosage form is achievable on maintaining improvement of subjective Wake After Sleep Onset (sWASO) during a treatment for at least one month.

Embodiment 87. The method according to Embodiment 86, the dosage form is achievable on maintaining improvement of sleep efficiency in subjective Sleep Efficiency (sSE) during a treatment for at least one month.

Embodiment 88. The method according to Embodiment 86, wherein the dosage form may be administered to the patient for at least one month.

Embodiment 89. The method according to Embodiment 86, wherein the dosage form may be administered to the patient for at least six months.

Embodiment 90. The method according to Embodiment 86, wherein the sWASO is reduced by at least 29 minutes relative to baseline.

In order that the disclosure described herein may be more fully understood, the following examples are set forth. It should be understood that these examples are for illustrative purposes only and are not to be construed as limiting this disclosure in any manner.

EXAMPLES

Abbreviations and Definitions

As used herein, the following abbreviations and definitions shall apply, unless indicated otherwise:

eC-SSRS—electronic Columbia-Suicide Severity Rating Scale: a self-rated suicidality scale which assesses an individual's degree of suicidality, including both suicidal ideation and suicidal behavior.

EQ-5D-3L—Health-related Quality of Life Assessment: an instrument that can be used in the clinical and economic evaluation of health care, and to collect data on quality of life and preferences/utilities. The instrument comprises questions on mobility, self-care, usual activities, pain/discomfort and anxiety/depression, and a visual analogue scale from 0 ("worst imaginable health state") to 100 ("best imaginable health state").

LPS—latency to persistent sleep: minutes from lights off to the first epoch of 20 consecutive epochs of non-wakefulness.

PGI-Insomnia—Patient Global Impression-Insomnia: a self-report assessment asking about a subject's perception of the effects of the study drug on their sleep relative to their sleep before entering in the study. The PGI-Insomnia has 3 items related to study drug effects (a: helped/worsened sleep, b: decreased/increased time to fall asleep, and c: increased/decreased TST) and 1 item (1=positive medication effect, 2=neutral medication effect, 3=negative medication effect) and the last item on a different 3-point scale (medication: 1=too strong, 2=just right, 3=too weak). Each item was reported separately.

SAE—serious adverse event

SDSB—Sleep Disorders Screening Battery

SE—sleep efficiency: proportion of time spent asleep per time in bed, calculated as TST/interval from lights off until lights on.

sSE—subjective sleep efficiency: proportion of sTST per subjective time spent in bed, calculated as the interval from the time the subject reports attempting to sleep until the time the subject stopped trying to sleep for the night (operationalized as the time the subject got out of bed for the day), and time spent asleep derived from subjective time in bed minus sWASO.

sSOL—subjective sleep onset latency: estimated minutes from the time that the subject attempted to sleep until sleep onset.

sTST—subjective total sleep time: derived minutes of sleep from sleep onset until the time the subject stopped trying to sleep for the night.

sWASO—subjective wake after sleep onset: sum of estimated minutes of wake during the night after initial sleep onset until the time the subject stopped trying to sleep for the night, operationalized as the time the subject got out of bed for the day.

T-BWSQ—Tyrer Benzodiazepine Withdrawal Symptom Questionnaire: a questionnaire designed to assess withdrawal symptoms upon discontinuation study drug. Tyrer, P. et al. "The benzodiazepine withdrawal symptom questionnaire." J. Affect. Disord. 1990; 19(1): 53-61.

TEAE—treatment-emergent adverse event

TST—total sleep time: minutes of sleep from sleep onset until terminal awakening.

WASO—wake after sleep onset: minutes of wake from the onset of persistent sleep until lights on.

WASO2H: wake after sleep onset in the second half of the night: minutes of wake during the interval from 240 minutes after lights off until lights on.

WPAI-GH—Work Productivity and Activity Impairment Questionnaire-General Health: collects data on absenteeism and presentism. The scale comprises 6 items that are used to create the 4 scores. Outcomes are expressed as impairment percentages, with higher numbers indicating greater impairment and less productivity. The four scores include: (1) percent work time missed due to health; (2) percent impairment while working due to health; (3) percent overall work impairment due to health; and (4) percent activity impairment due to health.

Example 1. Treatment of Subjects Having Insomnia Disorder

Subjects, both male and female, 18 years or older, where approximately 40% of the population was aged 65 years or older, were screened to be eligible for treatment. 971 subjects were randomized for treatment, however, only 949 subjects are in the full analysis set population. The demographic information of the subject population is shown in Table 1.

The study consisted of a prerandomization phase and a randomization phase.

Prerandomization Phase

The prerandomization phase consisted of three periods: screening, run-in, and baseline.

Screening Period

The screening period began no more than 35 days before the subject was to be randomized. Subjects were assessed based on eligibility criteria and other assessments (e.g., Sleep Disorders Screening Battery), and, if a subject was deemed to be eligible, the subject was trained on how to maintain a sleep diary and report measures of sleep parameters discussed herein. The subject then proceeded to the run-in period.

Run-In Period

The run-in period began when an eligible subject was administered a placebo tablet each night immediately before bed for at least 13 nights. During the run-in period, subjects needed to remain in bed for at least 7 hours each night, and maintain a regular bedtime.

Baseline Period

After treatment with placebo during the run-in period, subjects were assessed (e.g., Insomnia Severity Index, clinical blood and urine analysis, vital signs, weight, and electrocardiogram) and, if still eligible, proceeded to the randomization phase.

Randomization Phase

The randomization phase consisted of two periods: treatment period 1 and treatment period 2. The randomization phase lasted for 12 months.

Subjects were randomized in a double-blind manner and received either placebo, 5 mg of lemborexant, or 10 mg of lemborexant (approximately 1:1:1 randomization). All subjects underwent routine safety monitoring through the study, including assessments of treatment-emergent adverse events, 12-lead electrocardiograms, vital signs, weight, and clinical hematology and blood chemistry labs. Suicidality was assessed using the eC-SSRS.

Treatment Period 1

Treatment period 1 began with the first dose of randomized study medication (placebo, 5 mg of lemborexant, or 10 mg of lemborexant). Subjects completed sleep diaries daily in the morning, within one hour of waketime. The subjects were assessed by a clinician one month, two months, three months, and six months after initiation of Treatment period 1. The following assessments were conducted:

Month 1 Assessment: Standard safety assessments were performed on the subject. A blood sample was collected for determination of plasma concentration of lemborexant and its metabolites, and the ISI, FSS, PGI-Insomnia, EQ-5D-3L, and eC-SSR were completed.

Month 2 Assessment: Standard safety assessments were performed on the subject.

Month 3 Assessment: All assessments conducted at the Month 1 Assessment were repeated.

Month 6 Assessment: All assessments conducted at the Month 1 Assessment were repeated, and subjects completed the WPAI-GH.

After completion of the Month 6 Assessment, treatment period 1 ended and treatment period 2 began.

Treatment Period 2

At the end of the Month 2 Assessment of treatment period 1 (treatment period 2 baseline), subjects who received placebo during treatment period 1 underwent a second randomization to receive either 5 mg or 10 mg of lemborexant. Subjects who received lemborexant during treatment period 1 continued to receive lemborexant at the same dose.

During treatment period 2, subjects continued to complete a sleep diary as they did during treatment period 1. Subjects were assessed during Month 9 and Month 12 Assessments. For months 7, 8, 10, and 11, clinicians discussed treatment (e.g., sleep diary, concomitant medications, adverse events) via telephone.

During the Month 9 and 12 Assessments, safety and tolerability of lemborexant were assessed, the ec-SSR was completed, a urine drug test was conducted. Subjects also completed the ISI, FSS, EQ-5D-3L, PGI-Insomnia, and WPAI-GH. Blood samples (for pharmacokinetic analysis) were also collected.

Early Drug Discontinuation

Subjects who discontinued study drug prematurely at any time after start of the randomization phase were requested to return to visit a clinician within 7 days of discontinuation. These subjects were encouraged to continue to complete all study assessments (except collection of blood samples), including the sleep diary.

Follow-Up Period

The follow-up period began at the end of treatment period 2. Subjects ceased to take study drug, however, they continued to complete their sleep diary each morning until the end of study visit.

End of Study Visit

Between 14 and 18 days after completion of treatment period 2, subjects were assessed. In addition to standard safety assessments and completing the eC-SSRS, a urine drug test was conducted, the T-BWSQ was administered, and sleep diaries were collected.

Subject Population

Inclusion Criteria

Subjects were eligible for participation in the study if they met all of the following inclusion criteria:

- Male or female, aged 18 years or older at the time of giving informed consent.
- Met the Diagnostic and Statistical Manual of Mental Disorders, Fifth Edition (DSM 5) criteria for Insomnia Disorder:
  - i. complained of dissatisfaction with nighttime sleep in the form of difficulty getting to sleep, difficulty staying asleep and/or awakening earlier in the morning than desired despite adequate opportunity for sleep;
  - ii. frequency of complaint is 3 or more times per week;
  - iii. duration of complaint is 3 or more months;
  - iv. associated with complaint of daytime impairment.
- At screening: history of sSOL of 30 or more minutes on at least 3 nights per week in the previous 4 weeks and/or sWASO of 60 or more minutes on at least 3 nights per week in the previous 4 weeks.
- At screening: reported regular time spent in bed, either sleeping or trying to sleep, between 7 and 9 hours.
- At the first screening visit (Visit 1) and the second Screening visit (Visit 2a): reported regular bedtime, defined as the time the subject attempts to sleep, between 21:00 and 01:00 and regular waketime, defined as the time the subject got out of bed for the day, between 05:00 and 10:00.

ISI score of 15 or more at screening and study baseline.

At the second screening visit (Visit 2a): confirmation of current insomnia symptoms as determined from responses on the sleep diary completed on at least 7 consecutive mornings (minimum 5 of 7 for eligibility), such that sSOL was 30 or more minutes on at least 3 of the 7 nights and/or sWASO was 60 or more minutes on at least 3 of the 7 nights.

At the second screening visit (Visit 2a): confirmation of regular bedtimes and waketimes, as determined from responses on the sleep diary completed on a minimum of 7 consecutive mornings between the first and the second screening visits, such that the subject had a regular time spent in bed, either sleeping or trying to sleep, between 7 and 10 hours.

At the second screening visit (Visit 2a): confirmation of sufficient duration of time spent in bed, as determined from responses on the Sleep Diary completed on 7 mornings between the first and the second screening visits, such that there were not more than 2 nights with duration of time spent in bed <7 hours or >10 hours.

At baseline (Visit 3a): reconfirmation of insomnia symptoms, as determined from responses on the Sleep Diary for the final 7 nights of the run-in period, such that sSOL is 30 minutes or more on at least 3 of the 7 nights and/or sWASO is 60 minutes or more on at least 3 of the 7 nights.

At baseline (Visit 3a): confirmation of regular bedtimes and waketimes such that the subject had a regular time spent in bed, either sleeping or trying to sleep, between 7 and 10 hours for the final 7 nights of the run-in period.

At baseline (Visit 3a): reconfirmation of regular bedtime, defined as the time the subject attempted to sleep, between 21:00 and 01:00 and regular waketime, defined as the time the subject got out of bed for the day, between 05:00 and 10:00, for the final 7 nights of the run-in period.

Willing and able to comply with all aspects of the protocol, including staying in bed for at least 7 hours each night.

Willing to not start a behavioral or other treatment program for insomnia during the subject's participation in the study.

Exclusion Criteria

Subjects were not eligible for participation in the study if they met any of the following exclusion criteria:

Had a current diagnosis of sleep-related breathing disorder including obstructive sleep apnea (with or without continuous positive airway pressure (CPAP) treatment), periodic limb movement disorder, restless legs syndrome, circadian rhythm sleep disorder, or narcolepsy, or an exclusionary score on the SDSB as follows:

i. STOPBang score of 5 or more;

ii. IRLS score of 16 or more; and iii. ESS score of greater than 15.

Reported symptoms potentially related to narcolepsy that, in the clinical opinion of the investigator, indicated the need for referral for a diagnostic evaluation for the presence of narcolepsy.

Reported a history of sleep-related violent behavior, or sleep driving, or any other complex-related behavior, e.g., making phone calls, or preparing and eating food while asleep.

For subjects who underwent diagnostic polysomnogram analysis within 1 year before informed consent:

i. age 18 to 64 years: Apnea Hypopnea Index is 10 or greater, or Periodic Limb Movements with Arousal Index is 10 or greater.

ii. Aged 65 years or more: Apnea Hypopnea Index is greater than 15, or Periodic Limb Movements with Arousal Index is greater than 15.

Beck Depression Inventory-II (BDI-II) score is greater than 19 at screening.

Beck Anxiety Inventory (BAI) score is greater than 15 at screening.

Habitually napped more than 3 times per week.

Females who were breastfeeding or pregnant at Screening or Study Baseline (as documented by a positive serum beta human chorionic gonadotropin [β-hCG]). A separate baseline assessment was required if a negative screening pregnancy test had been obtained more than 72 hours before the first dose of study drug.

Females of childbearing potential who:

i. Had unprotected sexual intercourse within 30 days before study entry or who did not agree to use a highly effective method of contraception (eg, total abstinence, an intrauterine device, a contraceptive implant, injectable contraceptives, an oral contraceptive, or have a vasectomized partner with confirmed azoospermia) throughout the entire study period or for 28 days after study drug discontinuation. Periodic abstinence (e.g., calendar, ovulation, symptothermal, post-ovulation methods) and withdrawal are not acceptable methods of contraception.

ii. Were currently abstinent, and did not agree to use a highly effective method (as described above) or refrain from sexual activity during the study period and for 28 days after study drug discontinuation.

iii. Were using hormonal contraceptives but were not on a stable dose of the same hormonal contraceptive product for at least 4 weeks before dosing and who did not agree to use the same contraceptive during the study and for 28 days after study drug discontinuation.

iv. Note: All females were considered to be of childbearing unless they were postmenopausal (defined as amenorrheic for at least 12 consecutive months, in the appropriate age group, and were postmenopausal without other known or suspected cause) or had been sterilized surgically (i.e., bilateral tubal ligation, total hysterectomy, or bilateral oophorectomy, all with surgery at least 1 month before dosing).

Excessive caffeine use that, in the opinion of the investigator, contributed to the subject's insomnia, or habitually consumed caffeine containing beverages after 18:00 and was unwilling to forego caffeine after 18:00 for the duration of his or her participation in the study. Subjects were excluded if, in the previous 3 months, they had symptoms that would meet DSM-5 criteria for caffeine intoxication, which included consumption of a high dose of caffeine (significantly in excess of 250 mg) and ≥5 of the following symptoms: restlessness, nervousness, excitement, insomnia, flushed face, diuresis, gastrointestinal disturbance, muscle twitching, rambling flow of thought and speech, tachycardia or cardiac arrhythmia, periods of high energy, or psychomotor agitation. To be exclusionary, those symptoms caused distress or impairment in social, occupational and other forms of functioning, and were not associated with other substance, mental disorder or medical condition.

History of drug or alcohol dependency or abuse within approximately the previous 2 years.

Reported habitually consuming more than 14 drinks containing alcohol per week (females) or more than 21 drinks containing alcohol per week (males), or was unwilling to limit alcohol intake to 2 or fewer drinks per day or forego having alcohol within 3 hours before bedtime for the duration of his or her participation in the study.

Known to be positive for human immunodeficiency virus (HIV)

Active viral hepatitis (B or C) as demonstrated by positive serology at screening.

A prolonged QT/QT interval corrected by Fridericia's formula (QTcF) interval (QTcF>450 msec) as demonstrated by a repeated ECG at Screening (repeated only if initial ECG indicated a QTcF interval>450 msec).

Had current evidence of clinically significant disease (e.g., cardiac; respiratory including chronic obstructive pulmonary disease, acute and/or severe respiratory depression; severe hepatic insufficiency; gastrointestinal; renal including severe renal impairment; neurological [including subjects who lack capacity and/or whose cognitive decline indicates disorientation to person/place/time and/or situation] or psychiatric disease or malignancy within the past 5 years [other than adequately treated basal cell carcinoma]) or chronic pain that, in the opinion of the investigator, could affect the subject's safety or interfered with the study assessments. Subjects for whom a sedating drug would have been contraindicated for safety reasons because of the subject's occupation or activities were also excluded.

Comorbid nocturia resulting in frequent need to get out of bed to use the bathroom during the night.

Any history of a medical or psychiatric condition that, in the opinion of the investigator, may have affected the subject's safety or interfered with the study assessments.

Any suicidal ideation with intent with or without a plan at screening or study baseline or within 6 months of Study Baseline (i.e., answering "Yes" to questions 4 or 5 on the Suicidal Ideation section of the eC-SSRS).

Any suicidal behavior in the past 10 years (per the Suicidal Behavior section of the eCSSRS).

Scheduled for major surgery during the study.

Used any prohibited prescription or over-the-counter concomitant medications within 1 week or 5 half-lives, whichever was longer, before the first dose of study drug (run-in period).

Used any modality of treatment for insomnia, including cognitive behavioral therapy or marijuana within 1 week or 5 half-lives, whichever was longer, before the first dose of study drug (run-in period).

Failed treatment with suvorexant (efficacy or safety) following treatment with an appropriate dose and of adequate duration, in the opinion of the investigator.

Transmeridian travel across more than 3 time zones in the 2 weeks before screening, or between screening and baseline.

Had a positive drug test at screening, run-in, or baseline, or was unwilling to refrain from use of recreational drugs during the study.

Hypersensitivity to the study drug or any of the excipients.

Was currently enrolled in another clinical study or used any investigational drug or device within 30 days or 5 times the half-life, whichever was longer, preceding informed consent.

Previously participated in any clinical study of lemborexant.

Study Drug

Subjects were administered a 5 mg lemborexant tablet, a 10 mg lemborexant tablet, or a lemborexant-matched placebo tablet.

TABLE 1

Demographics of Study Subjects (Full Analysis Set).

| Category | Placebo (N = 318) | Lemborexant 5 mg (N = 316) | Lemborexant 10 mg (N = 315) | Combined Total (N = 949) |
|---|---|---|---|---|
| **Age** | | | | |
| Mean (SD) | 54.5 (14.01) | 54.2 (13.74) | 54.8 (13.68) | 54.5 (13.80) |
| Median | 56.0 | 55.0 | 55.0 | 55.0 |
| Min, Max | 18, 83 | 20, 85 | 18, 88 | 18, 88 |
| <65 years (%) | 229 (72) | 229 (72.5) | 229 (72.7) | 687 (72.4) |
| 65 to <75 years (%) | 69 (21.7) | 76 (24.1) | 65 (20.6) | 210 (22.1) |
| >=75 years (%) | 20 (6.3) | 11 (3.5) | 21 (6.7) | 52 (5.5) |
| **Sex** | | | | |
| Male (%) | 102 (32.1) | 107 (33.9) | 92 (29.5) | 302 (31.8) |
| Female (%) | 216 (67.9) | 209 (66.1) | 222 (70.5) | 647 (68.2) |

Study Endpoints

Primary Endpoint

The primary endpoint was the mean change from study baseline in subjective sleep onset latency at month 6.

Key Secondary Endpoints

This study had two key secondary endpoints. The first key secondary endpoint was the mean change from study baseline in subjective sleep efficiency at month 6. The second key secondary endpoint was the mean change from study baseline of subjective wake after sleep onset at month 6.

Additional Secondary Endpoints

In addition to the aforementioned study endpoints, the study included several additional secondary endpoints:

Mean change from study baseline of subjective sleep onset latency, subjective sleep efficiency, subjective wake after sleep onset, and subjective total sleep time at the beginning of treatment (mean of the 7 nights after the first dose in Period 1), at Month 1 and at Month 3.

Mean change from study baseline of subjective total sleep time at Month 6.

Change from study baseline in daytime functioning, assessed as the total score from the 4 items on daytime functioning, on the Insomnia Severity Index, at Months 1, 3, and 6.

Safety Endpoint

Safety endpoints for this study included the safety and tolerability of lemborexant (1) compared to placebo (during treatment period 1) and (2) in subjects exposed to lemborexant for 3, 6, 9, and 12 months.

Results

TABLE 2

Summary and Analysis of Change from Study Baseline for Subjective Sleep Onset Latency (Full Analysis Set).

| | Placebo (N = 318) | Lemborexant 5 mg(N = 316) | Lemborexant 10 mg(N = 315) |
|---|---|---|---|
| Study Baseline | | | |
| n | 316 | 314 | 312 |
| Mean (SD) | 64.03 (45.209) | 62.19 (45.674) | 64.97 (44.020) |
| Geometric mean | 44.99 | 42.97 | 45.05 |
| Median | 55.86 | 53.57 | 55.71 |
| First 7 Nights | | | |
| n | 315 | 312 | 313 |
| Mean (SD) | 59.94 (45.813) | 45.69 (38.455) | 45.94 (34.354) |
| Geometric Mean | 40.94 | 30.99 | 30.77 |
| Median | 50.71 | 36.58 | 35.71 |
| Change from Study Baseline after 7 Nights | | | |
| n | 314 | 310 | 310 |
| Mean (SD) | −4.11 (27.671) | −16.86 (27.784) | −18.89 (31.003) |
| Median | −3.00 | −11.00 | −12.21 |
| Month 1 | | | |
| n | 301 | 300 | 300 |
| Mean (SD) | 52.90 (42.955) | 41.89 (36.537) | 41.93 (33.521) |
| Geometric Mean | 34.61 | 26.98 | 27.14 |
| Median | 42.86 | 32.50 | 31.79 |
| Change from Study Baseline after 1 Month | | | |
| n | 299 | 298 | 297 |
| Mean (SD) | −11.48 (32.726) | −19.41 (32.221) | −24.06 (35.234) |
| Median | −7.14 | −13.71 | −19.86 |
| Month 3 | | | |
| n | 281 | 270 | 266 |
| Mean (SD) | 50.29 (50.260) | 34.31 (32.407) | 36.13 (34.327) |
| Geometric Mean | 29.62 | 21.72 | 22.71 |
| Median | 37.14 | 24.79 | 26.42 |
| Min, Max | 0.0, 394.3 | 0.0, 231.4 | 1.0, 289.4 |
| Change from Study Baseline after 3 Months | | | |
| n | 279 | 268 | 264 |
| Mean (SD) | −13.84 (35.277) | −25.08 (34.081) | −27.94 (39.192) |
| Median | −11.29 | −20.71 | −25.71 |
| Min, Max | −135.0, 205.7 | −220.0, 125.0 | −231.4, 260.3 |
| Month 6 | | | |
| n | 251 | 247 | 230 |
| Mean (SD) | 46.47 (45.010) | 29.49 (26.685) | 33.09 (32.167) |
| Geometric Mean | 27.42 | 18.62 | 19.35 |
| Median | 34.29 | 22.29 | 23.57 |
| Min, Max | 0.00, 334.3 | 0.0, 170.0 | 0.0, 240.0 |
| Change from Study Baseline after 6 Months | | | |
| n | 249 | 245 | 229 |
| Mean (SD) | −16.57 (35.313) | −29.39 (33.261) | −32.49 (35.962) |
| Median | −11.43 | −21.81 | −28.21 |
| Min, Max | −170.0, 171.4 | −212.1, 82.9 | −214.3, 74.3 |

SE = standard error.

LSM = least squares mean.

Subjective sleep onset latency is measured in minutes.

Figure 2:
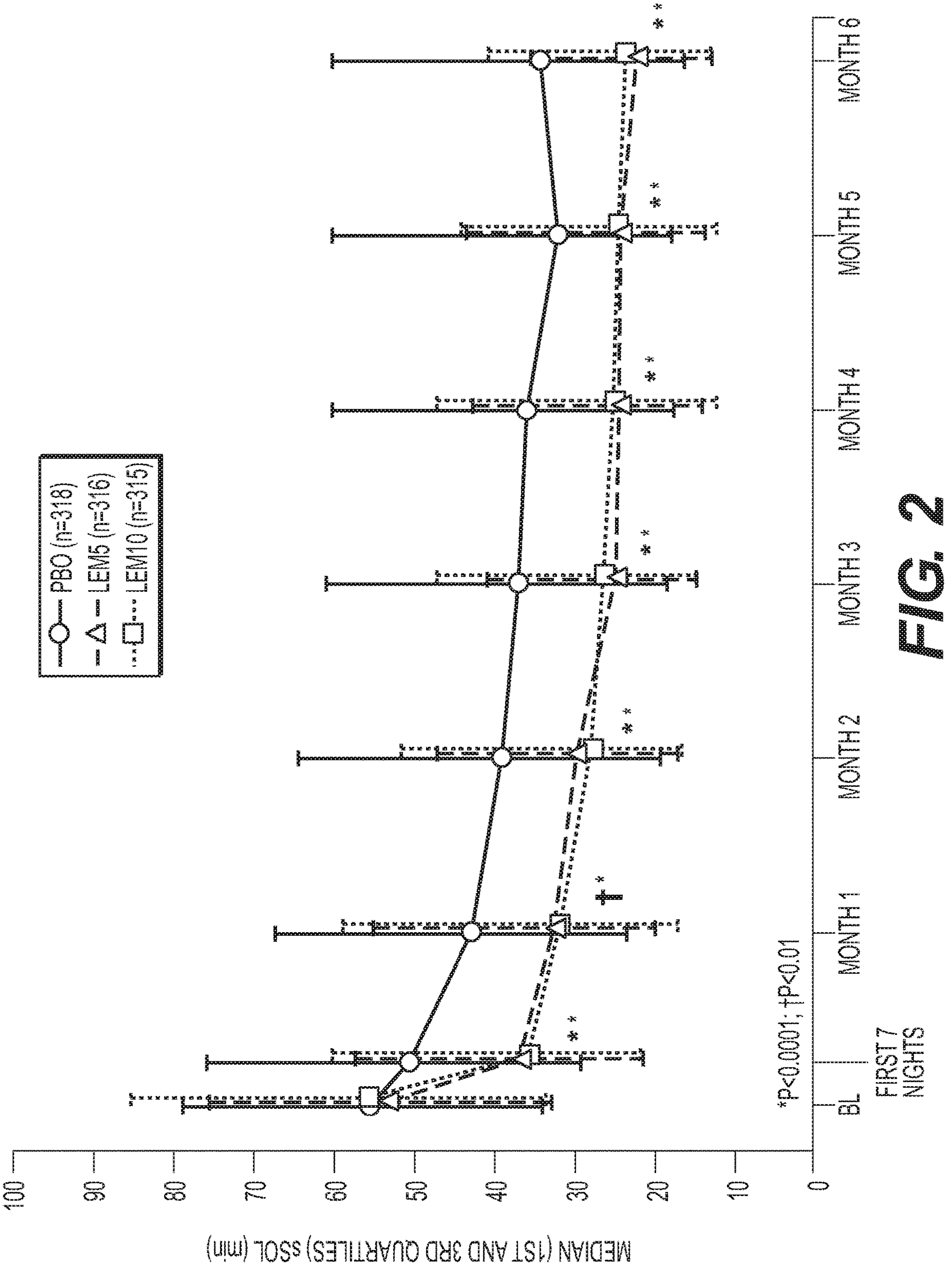
FIG. 2 shows the $1^{st}$ and $3^{rd}$ quartile median time, as a function of treatment duration, for subjective sleep onset latency in patients treated with placebo, 5 mg of lemborexant, or 10 mg of lemborexant.

The primary efficacy endpoint was the change from study baseline for mean subjective sleep onset latency, which is the estimated minutes from the time the subject attempted to sleep until sleep onset. As shown in Table 2, mean subjective sleep onset for all treatment groups was shorter than at study baseline and subjects treated with lemborexant experienced a shorter subjective sleep onset latency than subjects treated with placebo at the equivalent timepoint. See also FIG. 1 and FIG. 2.

TABLE 3

Summary and Analysis of Change from Study Baseline for Subjective Sleep Efficiency (Full Analysis Set).

| | Placebo (N = 318) | Lemborexant 5 mg (N = 316) | Lemborexant 10 mg (N = 315) |
|---|---|---|---|
| Study Baseline | | | |
| n | 307 | 302 | 299 |
| Mean (SD) | 61.34 (17.836) | 63.14 (18.231) | 62.03 (17.248) |
| Median | 63.47 | 67.00 | 65.05 |
| Min, Max | 14.6, 92.1 | 0.0, 93.5 | 9.2, 94.2 |
| First 7 Nights | | | |
| n | 309 | 304 | 306 |
| Mean (SD) | 63.88 (18.852) | 69.97 (18.312) | 69.96 (17.425) |
| Median | 67.13 | 74.62 | 71.85 |
| Min, Max | 8.3, 95.6 | 2.3, 97.4 | 16.8, 96.2 |
| Change from Study Baseline after 7 Nights | | | |
| n | 303 | 295 | 296 |
| Mean (SD) | 2.68 (10.765) | 6.61 (10.386) | 8.27 (10.566) |
| Median | 2.02 | 5.45 | 7.17 |
| Min, Max | −41.5, 39.0 | −27.7, 40.6 | −20.1, 54.1 |
| LSM treatment difference: Lemborexant-Placebo (SE) | — | 4.299 (0.848) | 5.793 (0.846) |
| P value | — | <0.0001 | <0.0001 |
| Month 1 | | | |
| n | 296 | 294 | 294 |
| Mean (SD) | 67.53 (18.248) | 71.56 (18.300) | 71.04 (17.551) |
| Median | 70.23 | 76.35 | 74.70 |
| Min, Max | 9.3, 96.2 | 3.1, 100.0 | 18.0, 96.9 |
| Change from Study Baseline after 1 Month | | | |
| n | 291 | 284 | 282 |
| Mean (SD) | 6.11 (12.876) | 7.87 (12.263) | 9.92 (12.922) |
| Median | 4.74 | 6.75 | 9.00 |
| Min, Max | −23.3, 75.1 | −43.2, 61.7 | −29.5, 67.2 |
| LSM treatment difference: Lemborexant-Placebo (SE) | — | 2.227 (0.979) | 3.615 (1.010) |
| P value | — | 0.0230 | 0.0003 |
| Month 3 | | | |
| n | 276 | 264 | 261 |
| Mean (SD) | 70.58 (18.542) | 77.29 (15.259) | 75.15 (17.206) |
| Median | 74.84 | 81.32 | 78.30 |
| Min, Max | 6.0, 99.6 | 19.7, 100.0 | 14.1, 98.9 |
| Change from Study Baseline after 3 Months | | | |
| n | 269 | 256 | 251 |
| Mean (SD) | 9.16 (13.644) | 13.03 (13.522) | 13.61 (14.035) |
| Median | 7.90 | 11.63 | 12.62 |
| Min, Max | −33.9, 65.6 | −18.7, 70.5 | −25.3, 72.1 |
| LSM treatment difference: Lemborexant-Placebo (SE) | — | 4.222 (1.099) | 4.361 (1.092) |
| P value | — | <0.0001 | <0.0001 |
| Month 6 | | | |
| n | 247 | 245 | 228 |
| Mean (SD) | 71.40 (18.314) | 78.55 (16.244) | 76.53 (17.987) |
| Median | 74.77 | 82.02 | 80.22 |

TABLE 3-continued

Summary and Analysis of Change from Study Baseline for Subjective Sleep Efficiency (Full Analysis Set).

| | Placebo (N = 318) | Lemborexant 5 mg (N = 316) | Lemborexant 10 mg (N = 315) |
|---|---|---|---|
| Min, Max | 6.3, 100.0 | 8.9, 98.9 | 16.1, 100.0 |
| Change from Study Baseline after 6 Months | | | |
| n | 242 | 235 | 220 |
| Mean (SD) | 10.36 (13.799) | 15.34 (14.613) | 15.55 (15.617) |
| Median | 8.97 | 13.33 | 13.91 |
| Min, Max | −38.0, 56.1 | −20.9, 64.5 | −20.6, 75.0 |
| LSM treatment difference: Lemborexant-Placebo (SE) | — | 4.549 (1.179) | 4.667 (1.170) |
| P value | — | <0.0001 | <0.0001 |

SE = standard error.

LSM = least squares mean.

Subjective sleep efficiency is indicated in %.

Figure 3:
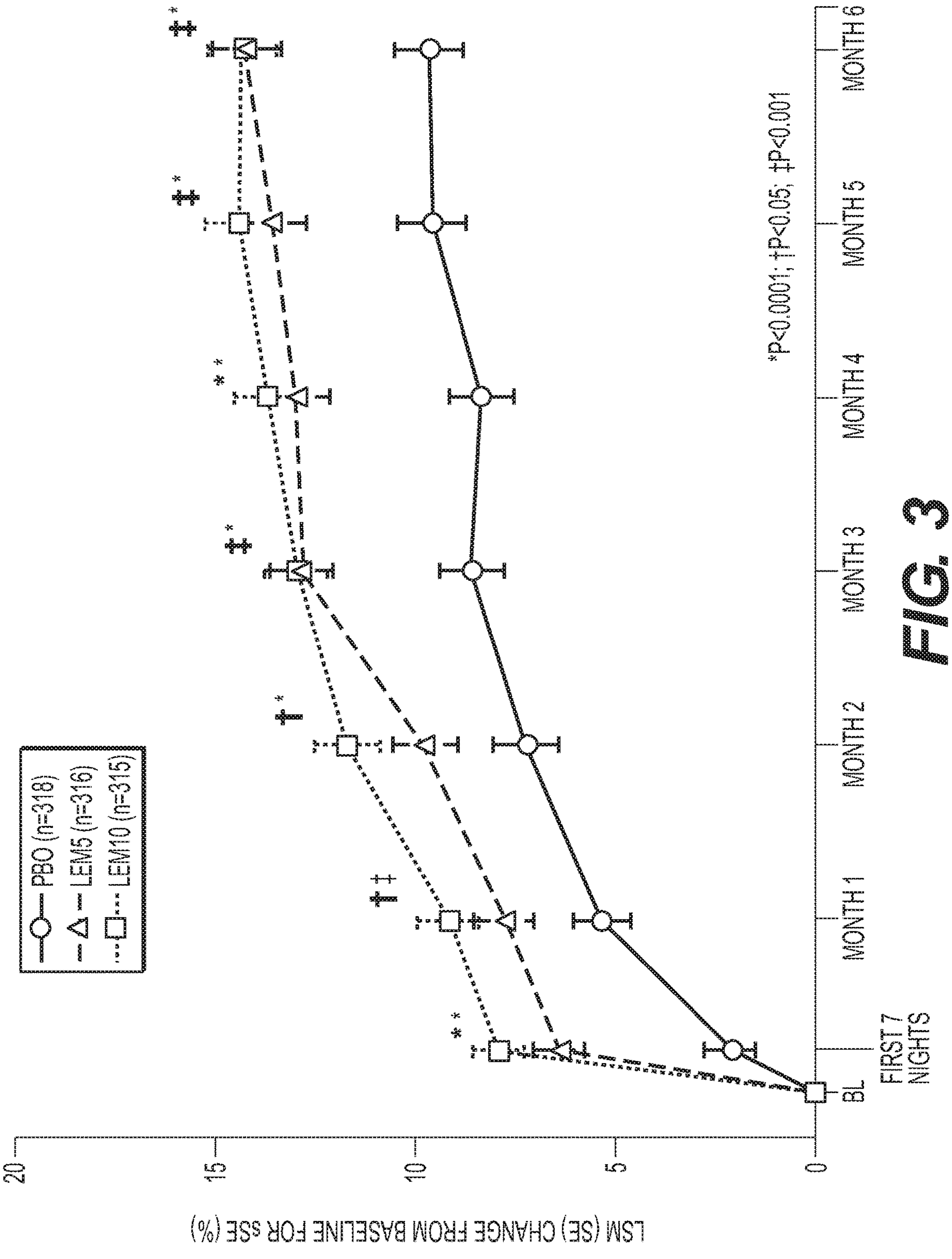
FIG. 3 shows the change from baseline (least squares mean) in sleep efficiency percentage, as a function of treatment duration, for subjective sleep efficiency in patients treated with placebo, 5 mg of lemborexant, or 10 mg of lemborexant.
Figure 4:
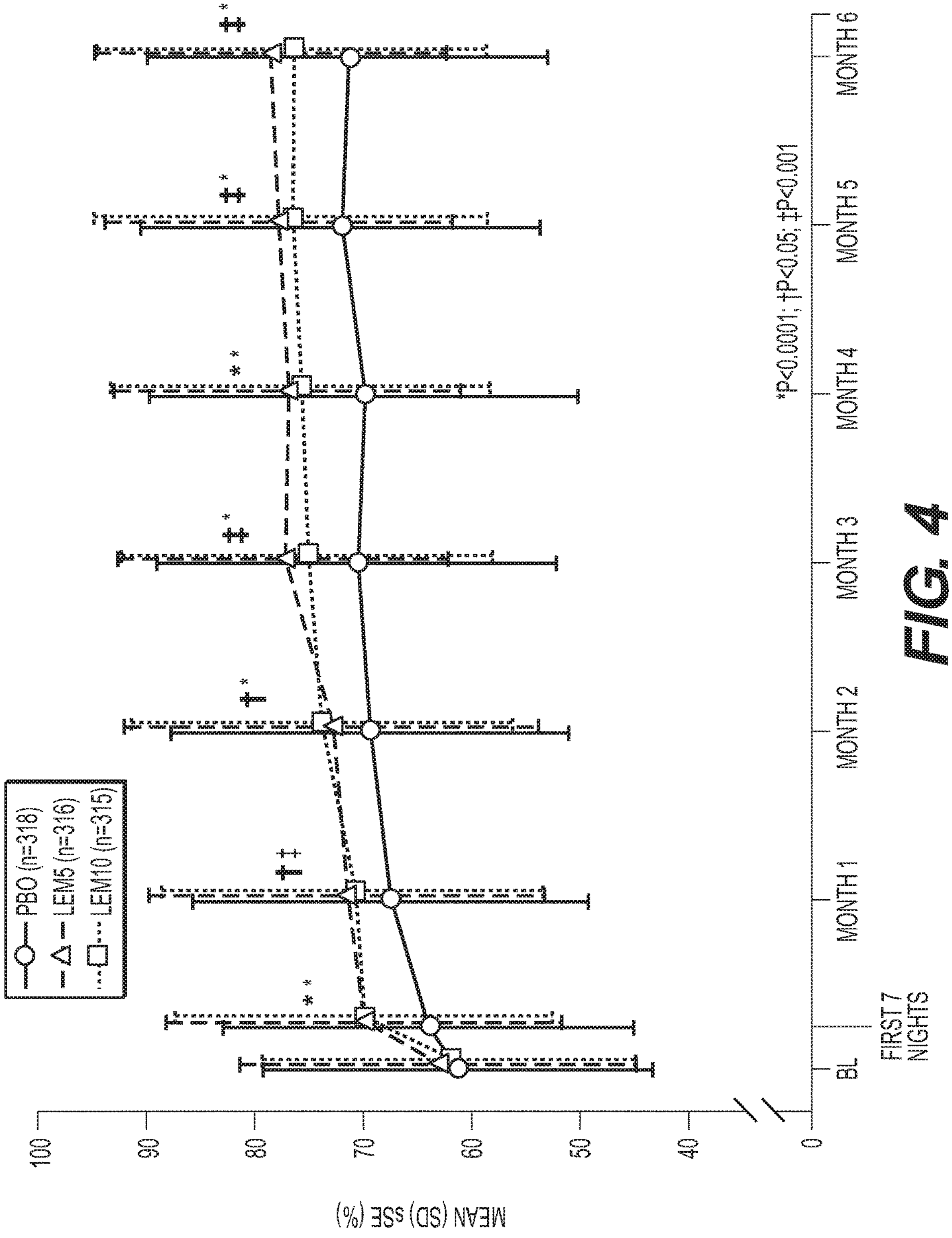
FIG. 4 shows the mean sleep efficiency percentage, as a function of treatment duration, for subjective sleep efficiency in patients treated with placebo, 5 mg of lemborexant, or 10 mg of lemborexant.

As shown in Table 3, mean subjective sleep efficiency for all treatment groups was increased relative to study baseline and subjects treated with lemborexant experienced a greater increase in subjective sleep efficiency than subjects treated with placebo at the equivalent timepoint. See also FIG. 3 and FIG. 4.

TABLE 4

Summary and Analysis of Change from Study Baseline for Subjective Wake After Sleep Onset (Full Analysis Set).

| | Placebo (N = 318) | Lemborexant 5 mg (N = 316) | Lemborexant 10 mg (N = 315) |
|---|---|---|---|
| Study Baseline | | | |
| n | 314 | 313 | 311 |
| Mean (SD) | 132.49 (80.198) | 132.77 (82.518) | 136.83 (87.391) |
| Median | 120.0 | 114.71 | 120.57 |
| Min, Max | 1.4, 420.0 | 0.0, 430.0 | 0.7, 460.0 |
| First 7 Nights | | | |
| n | 315 | 311 | 313 |
| Mean (SD) | 127.79 (86.974) | 113.53 (85.724) | 113.77 (83.536) |
| Median | 111.67 | 87.86 | 92.29 |
| Min, Max | 0.0, 462.9 | 0.0, 497.5 | 0.0, 415.9 |
| Change from Study Baseline after 7 Nights | | | |
| n | 312 | 308 | 309 |
| Mean (SD) | −6.12 (45.893) | −20.21 (46.015) | −23.30 (47.700) |
| Median | −6.92 | −16.01 | −20.71 |
| Min, Max | −180.7, 261.0 | −233.1, 188.6 | −238.6, 153.0 |
| LSM treatment difference: Lemborexant/Placebo (SE) | — | −14.328 (3.614) | −16.720 (3.619) |
| P value | — | <0.0001 | <0.0001 |
| Month 1 | | | |
| η | 300 | 299 | 297 |
| Mean (SD) | 114.17 (81.341) | 107.07 (80.639) | 109.42 (79.993) |
| Median | 95.57 | 85.29 | 95.00 |
| Min, Max | 0.0, 455.0 | 0.0, 426.7 | 0.0, 414.1 |
| Change from Study Baseline after 1 Month | | | |
| n | 297 | 297 | 293 |
| Mean (SD) | −19.01 (50.279) | −23.42 (56.251) | −26.82 (56.989) |
| Median | −9.86 | −19.29 | −22.29 |
| Min, Max | −240.0, 110.7 | −293.6, 191.4 | −208.9, 178.0 |
| LSM treatment difference: Lemborexant/Placebo (SE) | — | −5.514 (4.109) | −7.005 (4.129) |
| P value | — | 0.1796 | 0.0898 |

TABLE 4-continued

Summary and Analysis of Change from Study Baseline for Subjective Wake After Sleep Onset (Full Analysis Set).

| | Placebo (N = 318) | Lemborexant 5 mg (N = 316) | Lemborexant 10 mg (N = 315) |
|---|---|---|---|
| **Month 3** | | | |
| n | 281 | 270 | 265 |
| Mean (SD) | 104.87 (83.462) | 89.48 (79.256) | 95.66 (85.018) |
| Median | 83.86 | 66.43 | 70.00 |
| Min, Max | 0.0, 445.7 | 0.0, 501.8 | 0.0, 491.4 |
| **Change from Study Baseline after 3 Months** | | | |
| n | 278 | 267 | 262 |
| Mean (SD) | −27.08 (54.408) | −42.98 (60.064) | −39.42 (62.783) |
| Median | −21.82 | −34.57 | −36.07 |
| Min, Max | −244.3, 167.5 | −337.5, 122.7 | −232.9, 255.1 |
| LSM treatment difference: Lemborexant/ Placebo (SE) | — | −13.424 (4.486) | −10.079 (4.578) |
| P value | — | 0.0028 | 0.0277 |
| **Month 6** | | | |
| n | 251 | 247 | 229 |
| Mean (SD) | 103.15 (82.294) | 81.79 (76.803) | 86.38 (77.793) |
| Median | 88.57 | 60.00 | 62.14 |
| Min, Max | 0.0, 446.0 | 0.0, 443.5 | 0.0, 390.7 |
| **Change from Study Baseline after 6 Months** | | | |
| n | 248 | 244 | 227 |
| Mean (SD) | −32.14 (55.279) | −51.45 (67.295) | −48.12 (68.550) |
| Median | −29.21 | −44.02 | −47.43 |
| Min, Max | −221.9, 141.1 | −346.4, 190.7 | −318.7, 137.9 |
| LSM treatment difference: Lemborexant/ Placebo (SE) | — | −17.474 (5.014) | −12.671 (4.951) |
| P value | — | 0.0005 | 0.0105 |

SE = standard error.
LSM = least squares mean.
Subjective wake after sleep onset is measured in minutes.

Figure 5:
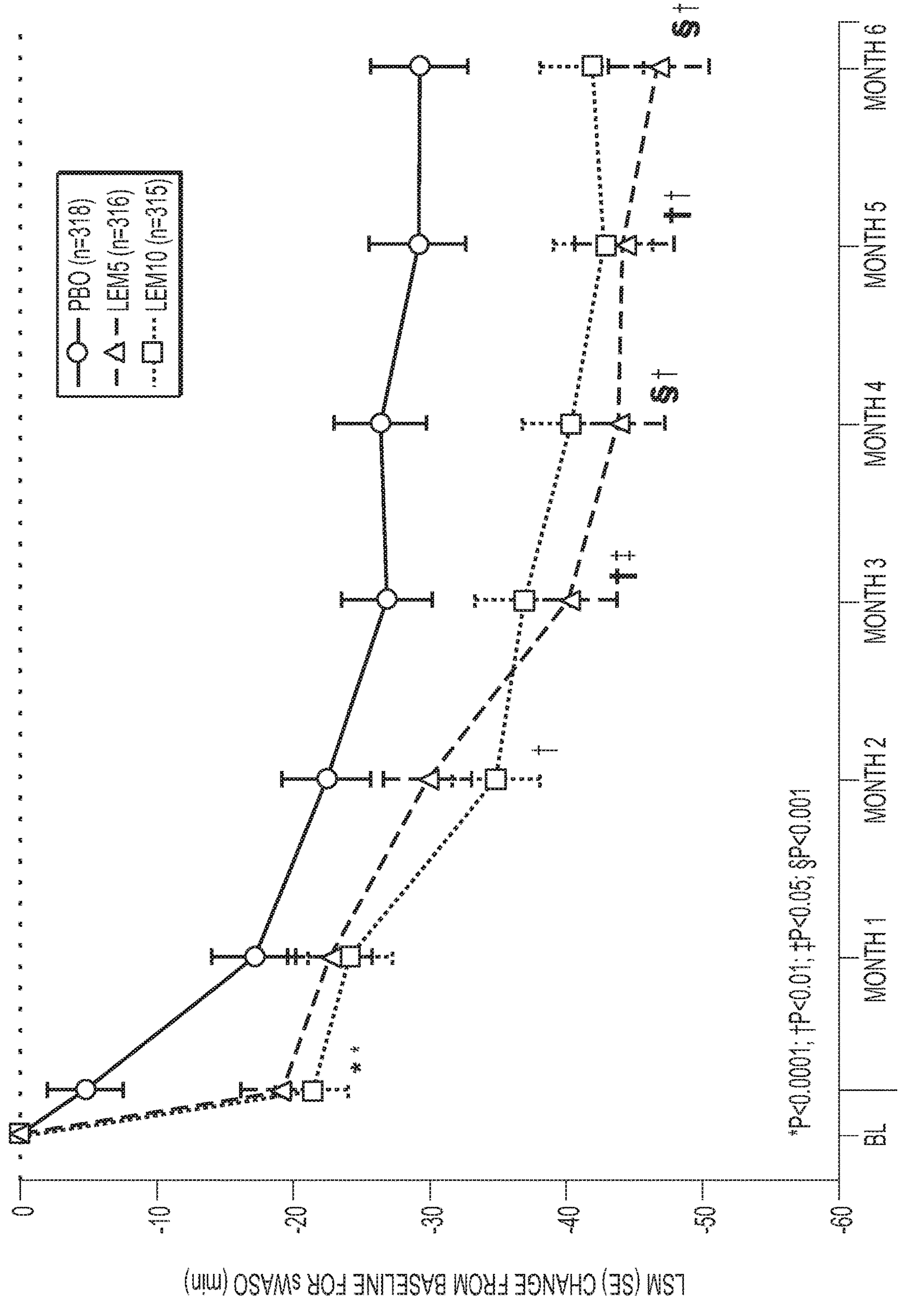
FIG. 5 shows the change from baseline (least squares mean) in median time, as a function of treatment duration, for subjective wake after sleep onset in patients treated with placebo, 5 mg of lemborexant, or 10 mg of lemborexant.
Figure 6:
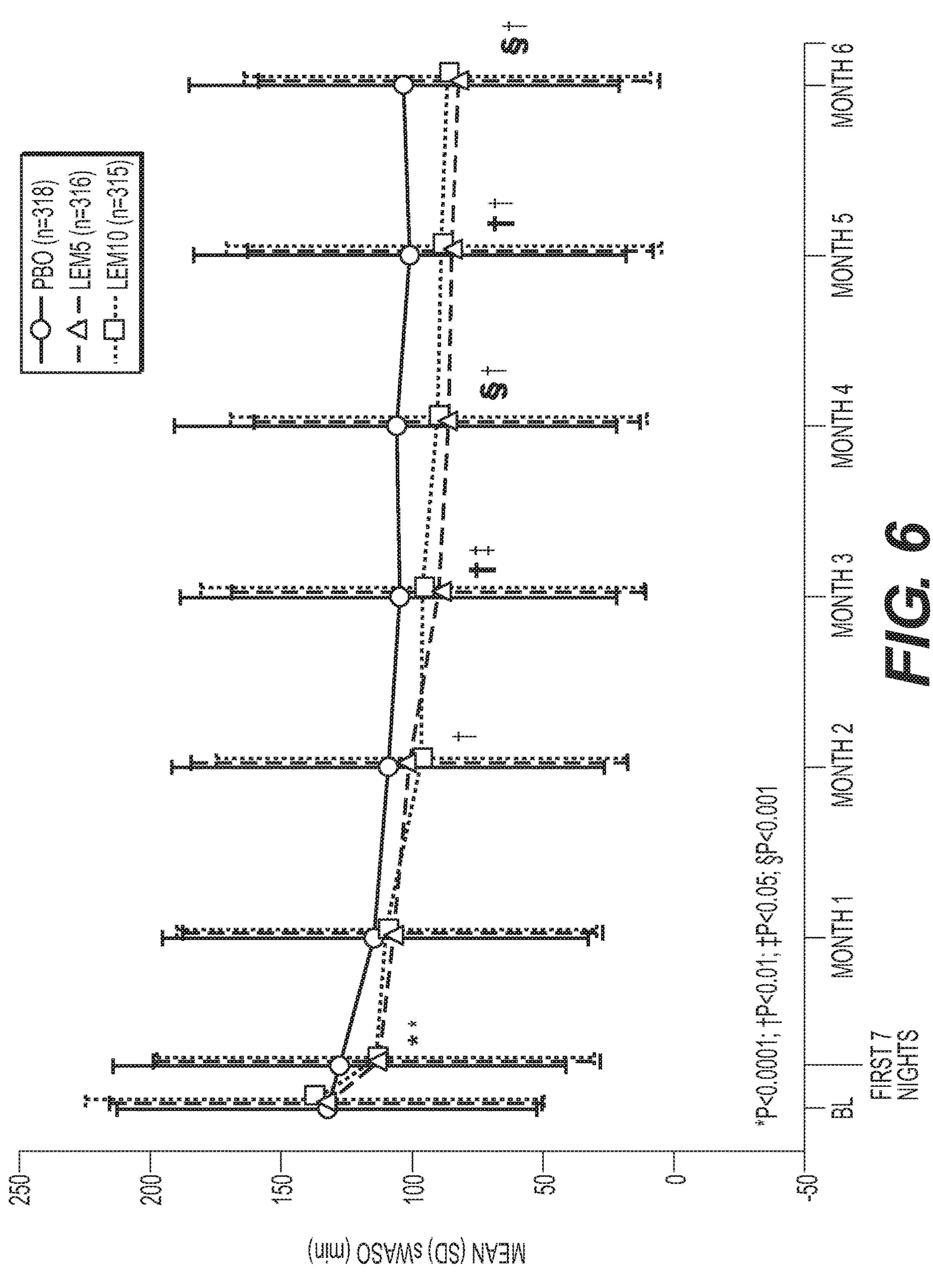
FIG. 6 shows the mean time, as a function of treatment duration, for subjective wake after sleep onset in patients treated with placebo, 5 mg of lemborexant, or 10 mg of lemborexant.
Figure 7:
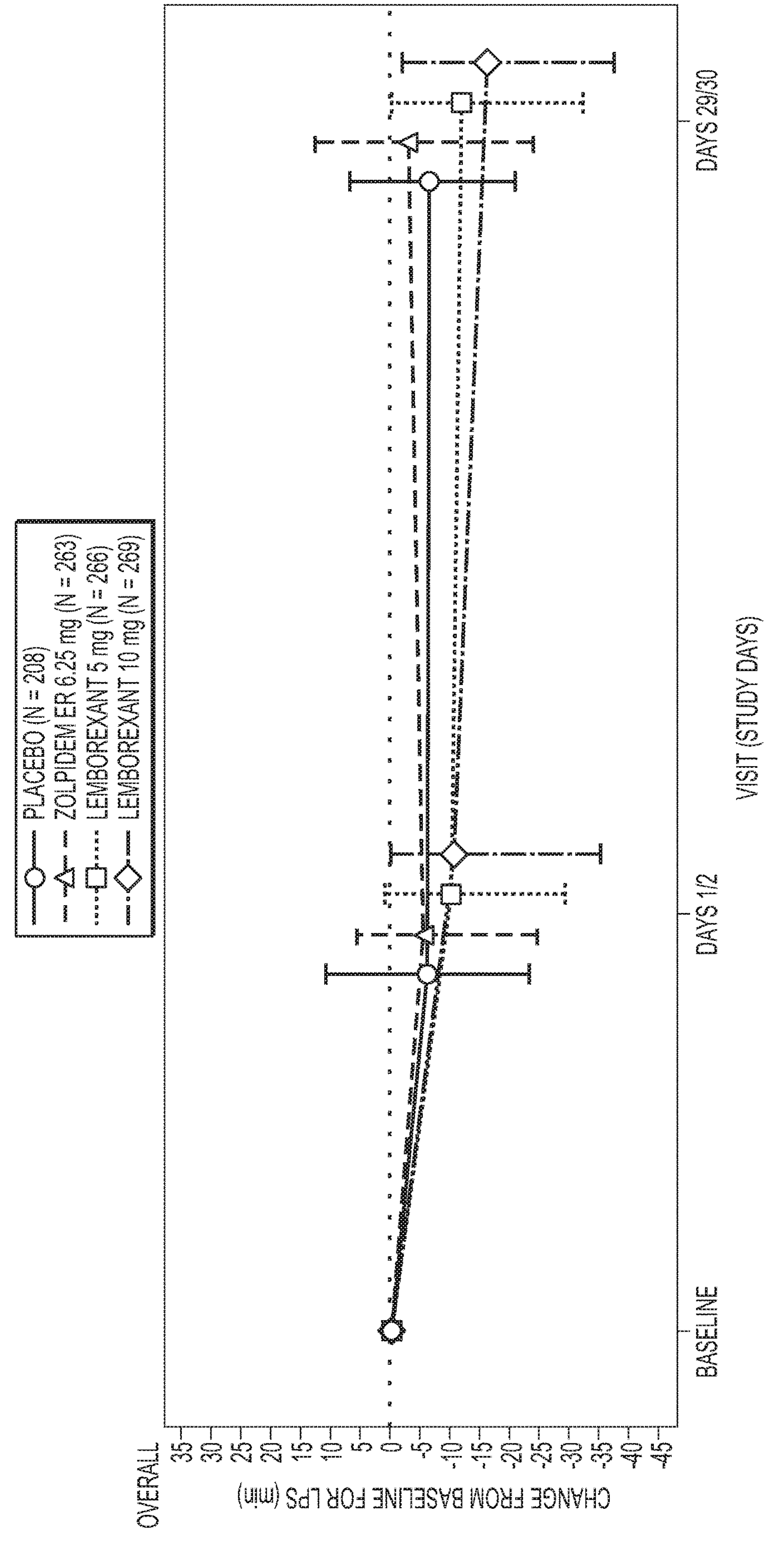
FIG. 7 shows the change from baseline in the $1^{st}$ and $3^{rd}$ quartile median time, as a function of treatment duration, for latency to persistent sleep in patients treated with placebo, 6.25 mg of zolpidem, 5 mg of lemborexant, or 10 mg of lemborexant.
Figure 8:
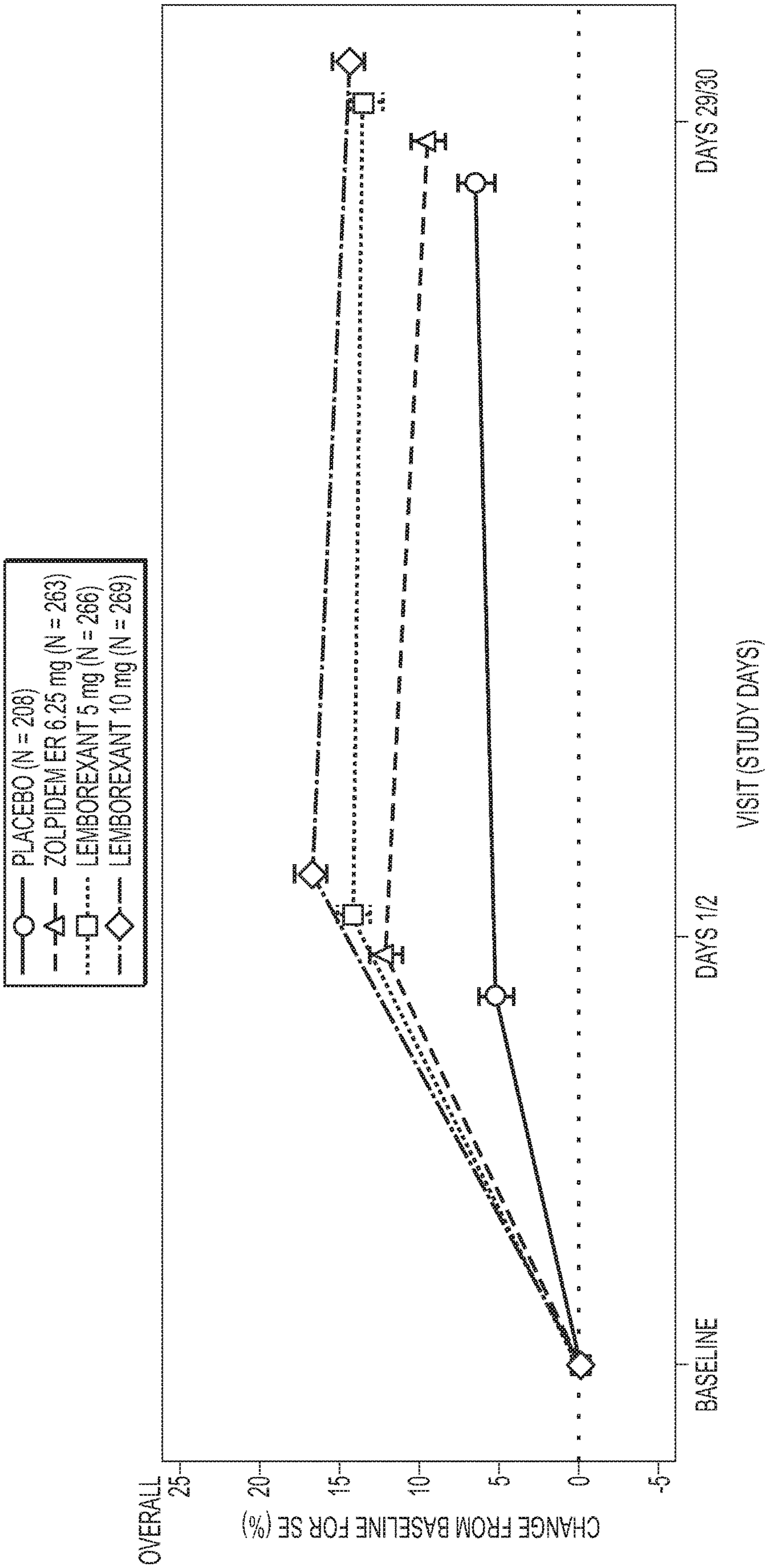
FIG. 8 shows the model estimate for change from baseline, as a function of treatment duration, for sleep efficiency percentage in patients treated with placebo, 6.25 mg of zolpidem, 5 mg of lemborexant, or 10 mg of lemborexant.
Figure 9:
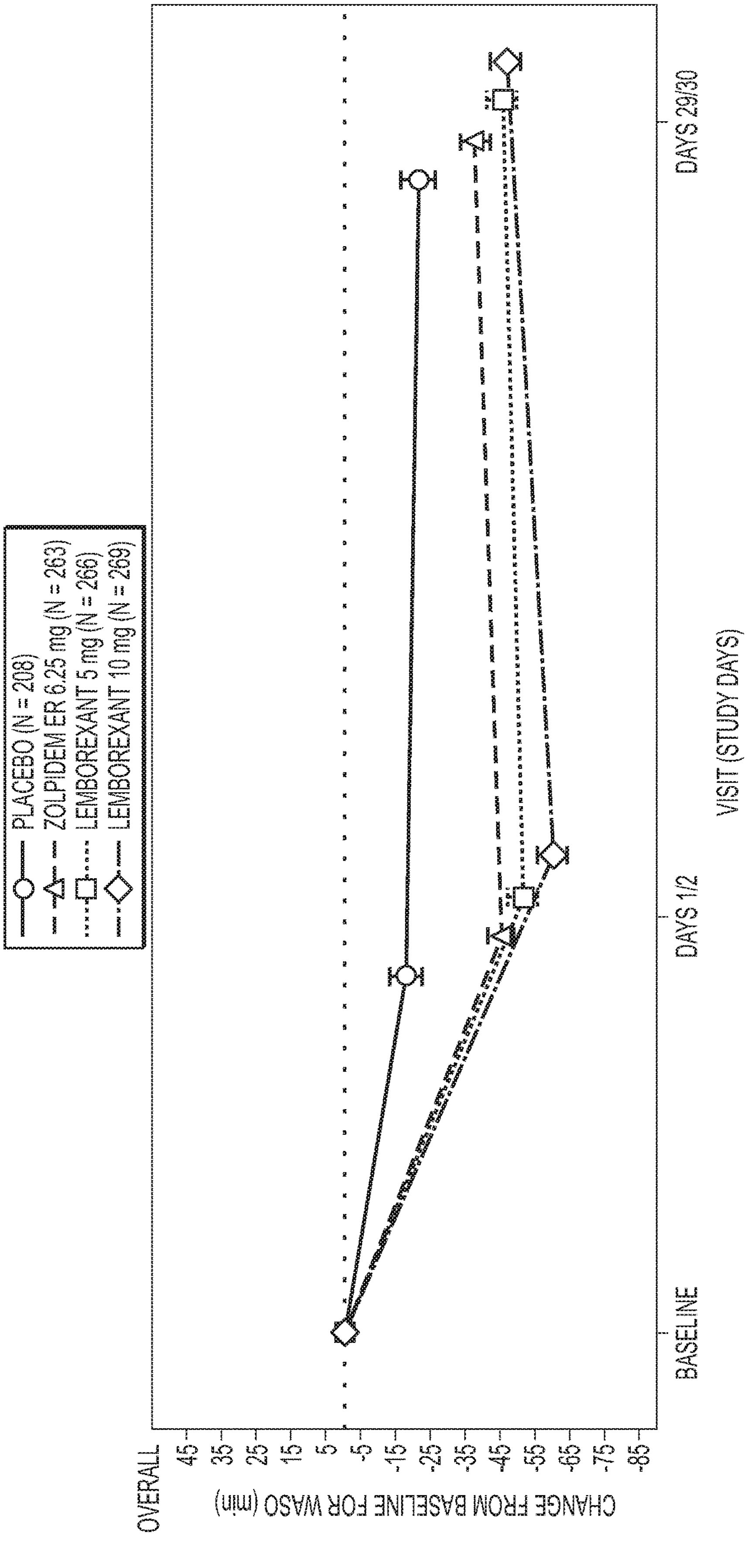
FIG. 9 shows the model estimate for change from baseline, as a function of treatment duration, for wake after sleep onset time in patients treated with placebo, 6.25 mg of zolpidem, 5 mg of lemborexant, or 10 mg of lemborexant.
Figure 10:
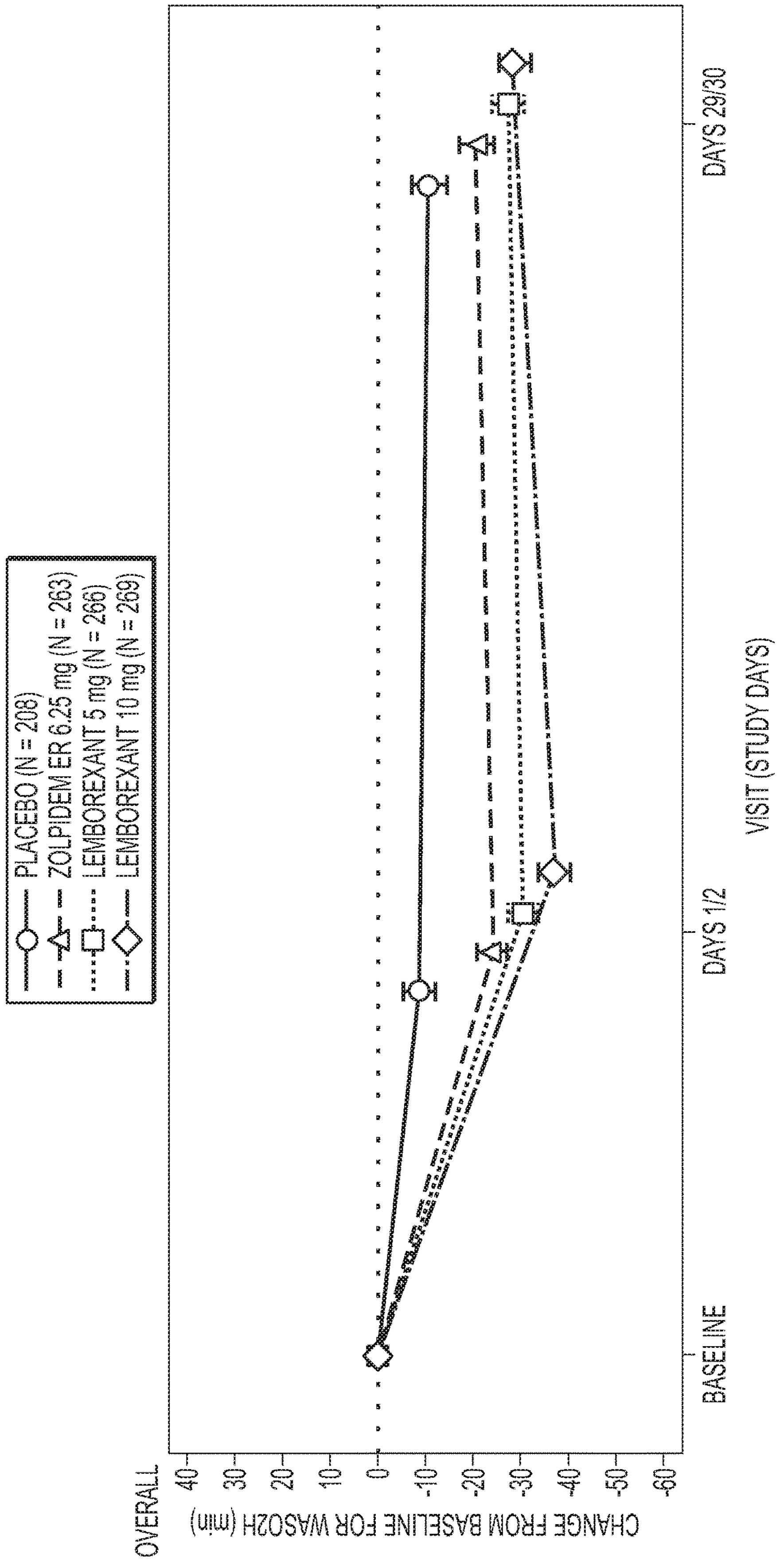
FIG. 10 shows the model estimate for change from baseline, as a function of treatment duration, for wake after sleep onset time in the second half of the night in patients treated with placebo, 6.25 mg of zolpidem, 5 mg of lemborexant, or 10 mg of lemborexant.
Figure 11A:
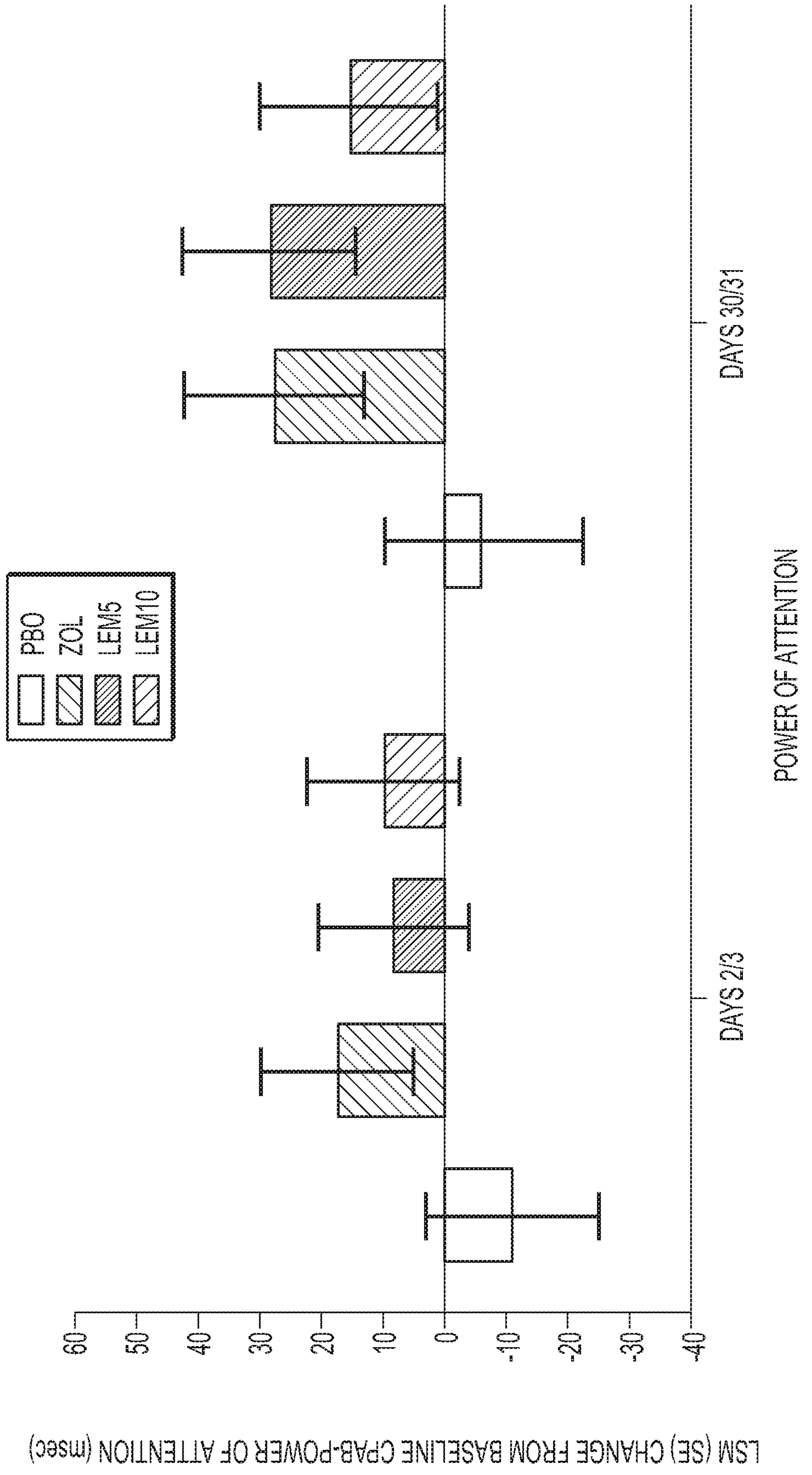
FIG. 11A-FIG. 11D show the change from baseline (least squares mean) in the four domains of the Cognitive Performance Assessment Battery at Days 2/3 and Days 30/31 in patients treated with placebo, 6.25 mg of zolpidem, 5 mg of lemborexant, or 10 mg of lemborexant.
Figure 11B:
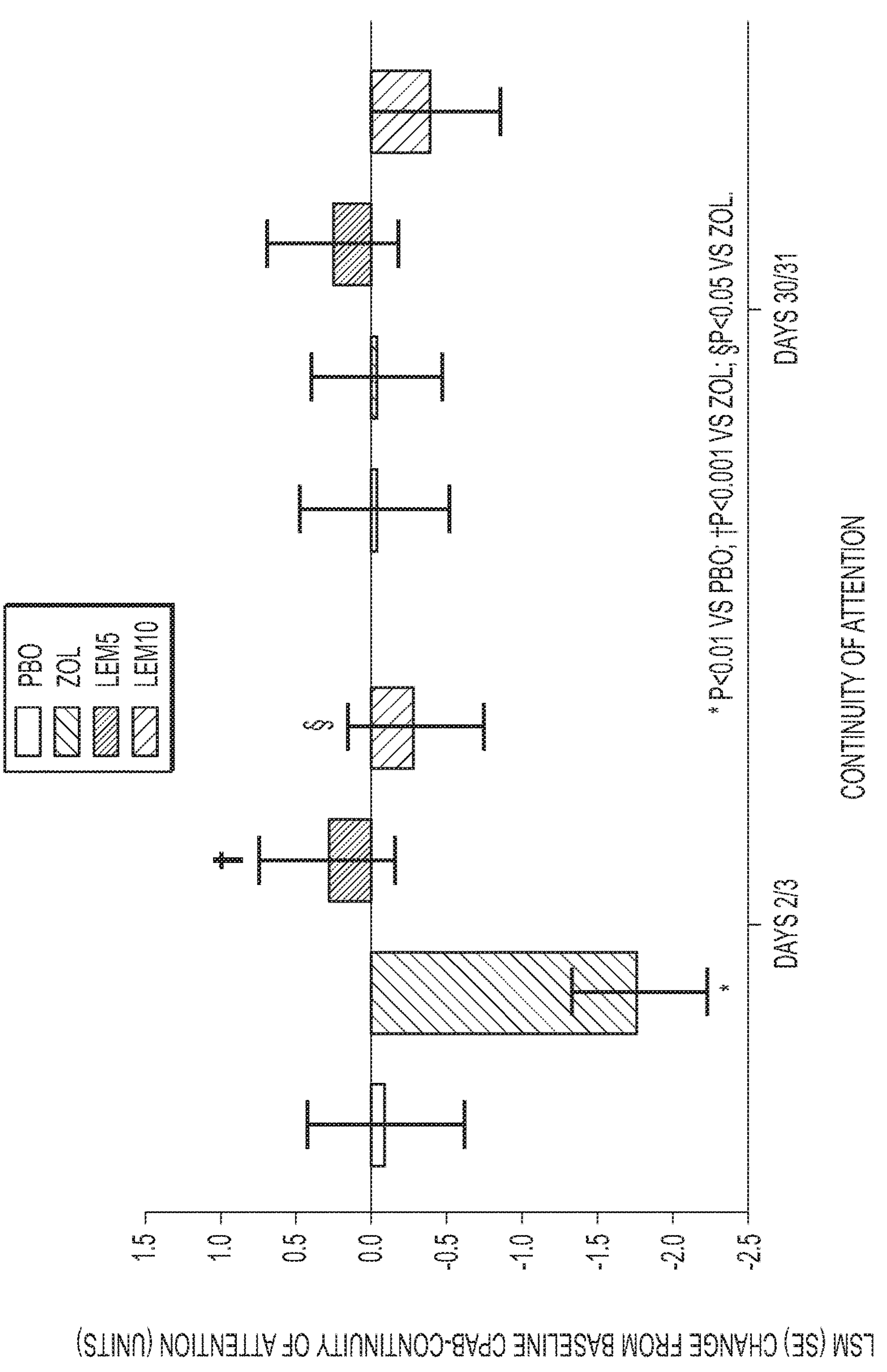
Figure 11C:
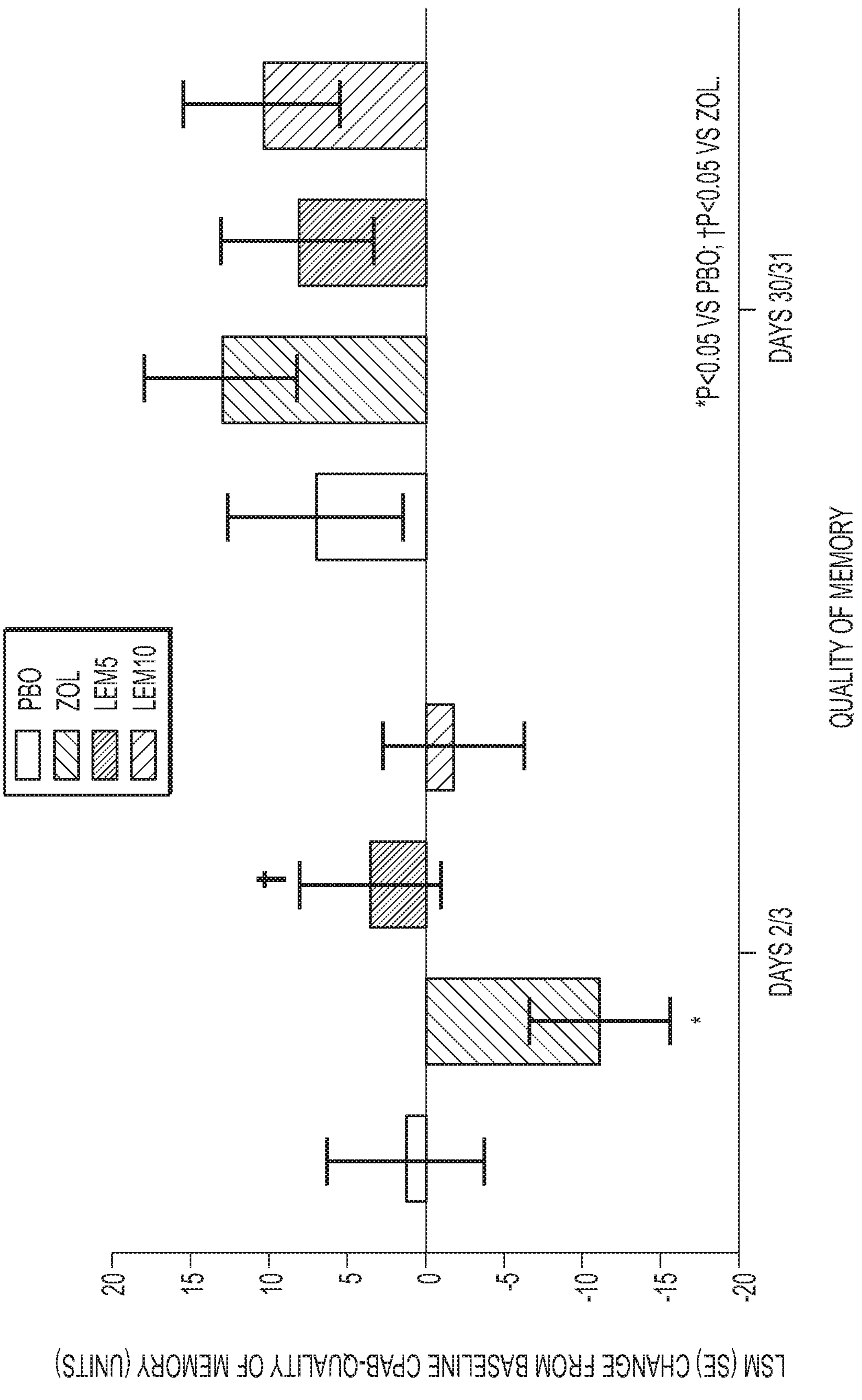
Figure 11D:
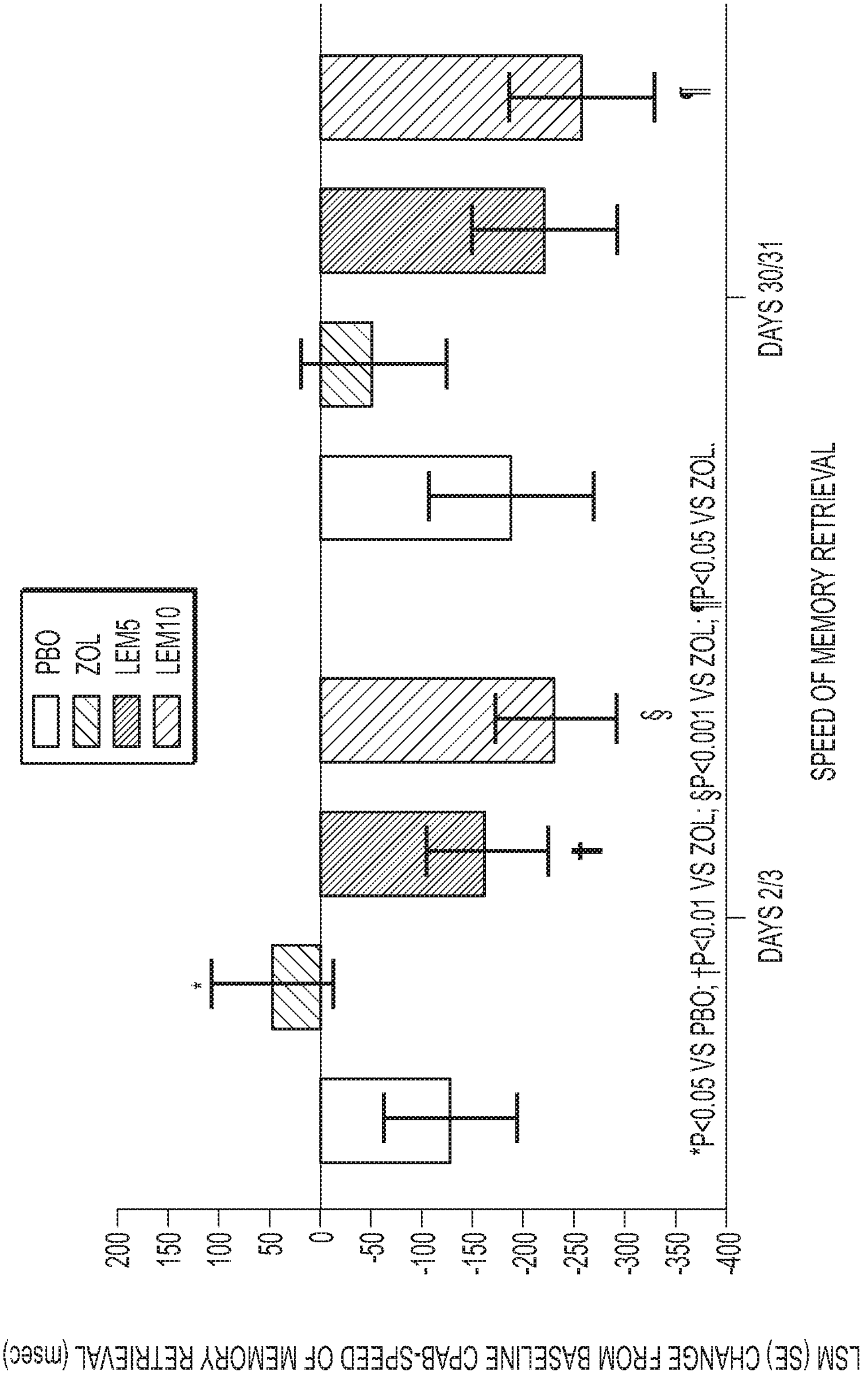

As shown in Table 4, mean subjective wake after sleep onset for all treatment groups was reduced relative to study baseline and subjects treated with lemborexant experienced a greater reduction in mean subjective wake after sleep onset than subjects treated with placebo at the equivalent timepoint. See also FIG. 5 and FIG. 6.

TABLE 5

Summary and Analysis of Change from Study Baseline for Subjective Total Sleep Time (Full Analysis Set).

| | Placebo (N = 318) | Lemborexant 5 mg (N = 316) | Lemborexant 10 mg (N = 315) |
|---|---|---|---|
| **Study Baseline** | | | |
| n | 307 | 302 | 299 |
| Mean (SD) | 304.25 (91.459) | 315.52 (93.498) | 306.89 (88.031) |
| Median | 314.71 | 332.14 | 315.33 |
| Min, Max | 70.0, 487.9 | 0.0, 531.2 | 38.6, 495.6 |
| **First 7 Nights** | | | |
| n | 309 | 304 | 306 |
| Mean (SD) | 318.51 (96.298) | 350.80 (95.999) | 351.43 (91.645) |
| Median | 332.57 | 366.0 | 365.11 |
| Min, Max | 40.0, 495.7 | 11.0, 520.7 | 85.0, 532.7 |
| **Change from Study Baseline after 7 Nights** | | | |
| n | 303 | 295 | 296 |
| Mean (SD) | 14.78 (54.995) | 34.29 (54.142) | 46.01 (55.110) |
| Median | 13.43 | 30.71 | 42.31 |
| Min, Max | −198.5, 196.1 | −186.1, 217.7 | −98.0, 292.4 |

TABLE 5-continued

Summary and Analysis of Change from Study Baseline for Subjective Total Sleep Time (Full Analysis Set).

| | Placebo (N = 318) | Lemborexant 5 mg (N = 316) | Lemborexant 10 mg (N = 315) |
|---|---|---|---|
| LSM treatment difference: Lemborexant/ Placebo (SE) | — | 22.034 (4.354) | 31.796 (4.350) |
| P value | — | <0.0001 | <0.0001 |
| Month 1 | | | |
| n | 296 | 294 | 294 |
| Mean (SD) | 335.83 (95.378) | 357.14 (93.503) | 355.96 (92.725) |
| Median | 344.57 | 374.64 | 369.23 |
| Min, Max | 45.0, 620.7 | 15.0, 540.3 | 94.3, 570.8 |
| Change from Study Baseline after 1 Month | | | |
| n | 291 | 284 | 282 |
| Mean (SD) | 30.74 (70.687) | 39.32 (63.548) | 53.22 (67.910) |
| Median | 22.14 | 36.33 | 47.77 |
| Min, Max | −116.7, 519.0 | −205.0, 323.7 | −171.5, 286.6 |
| LSM treatment difference: Lemborexant/ Placebo (SE) | — | 11.760 (5.269) | 22.131 (5.286) |
| P value | — | 0.0259 | <0.0001 |
| Month 3 | | | |
| n | 276 | 264 | 261 |
| Mean (SD) | 353.84 (98.698) | 386.42 (82.554) | 374.99 (91.602) |
| Median | 367.71 | 397.86 | 391.43 |
| Min, Max | 27.3, 639.8 | 97.5, 577.6 | 85.0, 537.5 |
| Change from Study Baseline after 3 Months | | | |
| n | 269 | 256 | 251 |
| Mean (SD) | 48.16 (75.859) | 65.82 (71.331) | 70.95 (70.913) |
| Median | 36.43 | 60.71 | 64.52 |
| Min, Max | −158.9, 386.2 | −97.0, 398.0 | −127.4, 355.0 |
| LSM treatment difference: Lemborexant/ Placebo (SE) | — | 17.374 (5.906) | 21.686 (5.946) |
| P value | — | 0.0034 | 0.0003 |
| Month 6 | | | |
| n | 247 | 245 | 228 |
| Mean (SD) | 356.03 (95.371) | 392.08 (86.951) | 379.25 (95.384) |
| Median | 362.00 | 403.43 | 398.57 |
| Min, Max | 30.0, 582.9 | 45.0, 589.0 | 77.1, 543.9 |
| Change from Study Baseline after 6 Months | | | |
| n | 242 | 235 | 220 |
| Mean (SD) | 53.53 (74.539) | 76.21 (77.714) | 78.32 (80.741) |
| Median | 45.50 | 70.71 | 72.93 |
| Min, Max | −179.3, 329.3 | −110.4, 365.5 | −121.6, 405.0 |
| LSM treatment difference: Lemborexant/ Placebo (SE) | — | 18.555 (6.324) | 22.686 (6.392) |
| P value | — | 0.0034 | 0.0004 |

SE = standard error.

LSM = least squares mean.

Subjective total sleep time is measured in minutes.

As shown in Table 5, mean subjective total sleep time for all treatment groups was increased relative to study baseline and subjects treated with lemborexant experienced a greater increase in subjective total sleep time than subjects treated with placebo at the equivalent timepoint.

TABLE 6

Summary and Analysis of Change from Study Baseline for Insomnia Severity Index Daytime Functioning (Items 4-7; Full Analysis Set).

| | Placebo (N = 318) | Lemborexant 5 mg (N = 316) | Lemborexant 10 mg (N = 315) |
|---|---|---|---|
| Study Baseline | | | |
| n | 318 | 316 | 315 |
| Mean (SD) | 110 (2.10) | 11.4 (2.02) | 11.0 (2.15) |
| Median | 11.0 | 11.0 | 11.0 |
| Min, Max | 1, 16 | 6, 16 | 2, 16 |
| Month 1 | | | |
| n | 296 | 300 | 286 |
| Mean (SD) | 7.8 (3.32) | 7.2 (3.78) | 7.0 (3.69) |
| Median | 8.0 | 7.0 | 7.0 |
| Min, Max | 0, 16 | 0, 16 | 0, 16 |
| Change from Study Baseline after 1 Month | | | |
| n | 296 | 300 | 286 |
| Mean (SD) | −3.1 (3.41) | −4.1 (3.66) | −4.2 (4.01) |
| Median | −3.0 | −3.0 | −4.0 |
| Min, Max | −14, 8 | −15, 3 | −15, 6 |
| LSM treatment difference: Lemborexant/Placebo (SE) | — | −0.71 (0.287) | −0.94 (0.289) |
| P value | — | 0.0137 | 0.0011 |
| Month 3 | | | |
| n | 283 | 274 | 259 |
| Mean (SD) | 7.2 (3.51) | 6.2 (3.82) | 6.0 (3.67) |
| Median | 8.0 | 6.0 | 5.0 |
| Min, Max | 0, 16 | 0, 16 | 0, 16 |
| Change from Study Baseline after 3 Months | | | |
| n | 283 | 274 | 259 |
| Mean (SD) | −3.7 (3.55) | −5.2 (3.88) | −5.2 (4.05) |
| Median | −3.0 | −5.0 | −5.0 |
| Min, Max | −14, 8 | −15, 3 | −16, 8 |
| LSM treatment difference: Lemborexant/Placebo (SE) | — | −1.16 (0.302) | −1.36 (0.305) |
| P value | — | 0.0001 | <0.0001 |
| Month 6 | | | |
| n | 257 | 258 | 234 |
| Mean (SD) | 6.6 (3.45) | 5.4 (3.58) | 5.4 (3.54) |
| Median | 7.0 | 5.0 | 5.0 |
| Min, Max | 0, 16 | 0, 15 | 0, 15 |
| n | 257 | 258 | 234 |
| Mean (SD) | −4.3 (3.66) | −6.0 (3.76) | −5.7 (4.00) |
| Median | −4.0 | −6.0 | −6.0 |
| Min, Max | −14, 4 | −15, 3 | −16, 7 |
| LSM treatment difference: Lemborexant/Placebo (SE) | — | −1.30 (0.302) | −1.32 (0.307) |
| P value | — | <0.0001 | <0.0001 |

SE = standard error.
LSM = least squares mean.

TABLE 7

Summary and Analysis of Change from Study Baseline for Insomnia Severity Total Score (Items 1-7; Full Analysis Set).

| | Placebo (N = 318) | Lemborexant 5 mg (N = 316) | Lemborexant 10 mg (N = 315) |
|---|---|---|---|
| Study Baseline | | | |
| n | 318 | 316 | 315 |
| Mean (SD) | 19.0 (3.08) | 19.6 (3.28) | 19.0 (3.39) |
| Median | 19.0 | 19.0 | 19.0 |
| Min, Max | 4, 27 | 11, 28 | 5, 28 |
| Month 1 | | | |
| n | 296 | 300 | 286 |
| Mean (SD) | 13.8 (5.24) | 12.6 (6.04) | 12.0 (5.89) |
| Median | 14.0 | 12.0 | 12.0 |
| Min, Max | 0, 28 | 0, 28 | 0, 28 |
| Change from Study Baseline after 1 Month | | | |
| n | 296 | 300 | 286 |
| Mean (SD) | −5.2 (5.23) | −7.1 (5.91) | −7.2 (6.42) |
| Median | −4.0 | −6.0 | −6.0 |
| Min, Max | −22, 10 | −27, 4 | −26, 9 |
| LSM treatment difference: Lemborexant/Placebo (SE) | — | −1.47 (0.457) | −1.87 (0.461) |
| P value | — | 0.0013 | <0.0001 |
| Month 3 | | | |
| η | 283 | 274 | 259 |
| Mean (SD) | 12.8 (5.66) | 10.8 (6.07) | 10.2 (5.78) |
| Median | 14.0 | 10.0 | 10.0 |
| Min, Max | 0, 28 | 0, 28 | 0, 28 |
| Change from Study Baseline after 3 Months | | | |
| n | 283 | 274 | 259 |
| Mean (SD) | −6.1 (5.55) | −8.6 (6.28) | −8.9 (6.38) |
| Median | −5.0 | −8.0 | −9.0 |
| Min, Max | −21, 10 | −27, 5 | −27, 11 |
| LSM treatment difference: Lemborexant/Placebo (SE) | — | −2.02 (0.481) | −2.57 (0.486) |
| P value | — | <0.0001 | <0.0001 |
| Month 6 | | | |
| n | 257 | 258 | 234 |
| Mean (SD) | 11.8 (5.60) | 9.6 (5.70) | 9.4 (5.72) |
| Median | 12.0 | 9.0 | 9.0 |
| Min, Max | 0, 26 | 0, 27 | 0, 26 |
| Change from Study Baseline after 6 Months | | | |
| n | 257 | 258 | 234 |
| Mean (SD) | −7.2 (5.75) | −9.9 (6.07) | −9.8 (6.61) |
| Median | −7.0 | −10.0 | −9.5 |
| Min, Max | −22, 6 | −26, 3 | −26, 8 |
| LSM treatment difference: Lemborexant/Placebo (SE) | — | −2.10 (0.487) | −2.35 (0.495) |
| P value | — | <0.0001 | <0.0001 |

SE = standard error.
LSM = least squares mean.

As shown in Tables 6 and 7, mean insomnia severity index scores for all treatment groups decreased relative to study baseline and subjects treated with lemborexant experienced a greater decrease in insomnia severity index score than subjects treated with placebo at the equivalent timepoint.

TABLE 8

| Mean Score Values of Quality of Sleep and Morning Sleepiness. | | | | |
|---|---|---|---|---|
| | | Placebo (N = 318) | Lemborexant 5 mg (N = 316) | Lemborexant 10 mg (N = 315) |
| Quality of Sleep | | | | |
| Baseline | Mean (SD) | 3.8 (1.4) | 4.0 (1.3) | 4.0 (1.4) |
| Change from baseline at Month 6 | LSM (SE) | 0.89 (0.09) | 1.17 (0.09) | 1.21 (0.09) |
| | Treatment difference | — | 0.28 | 0.32 |
| | P value | — | 0.0244 | 0.0103 |
| Morning Sleepiness | | | | |
| Baseline | Mean (SD) | 3.94 (1.56) | 3.93 (1.35) | 3.93 (1.32) |
| Change from baseline at Month 6 | LSM (SE) | 0.78 (0.09) | 0.93 (0.09) | 1.04 (0.09) |
| | Treatment difference | — | 0.15 | 0.26 |
| | P value | — | 0.2248 | 0.0298 |

As shown in Table 8, mean values of the items related to quality of sleep and morning sleepiness (Insomnia Severity Index) were significantly improved in subjects treated with lemborexant compared to those treated with placebo at 6 months.

TABLE 9

Summary of Plasma Concentrations of Lemborexant (5 mg dose) and Lemborexant Metabolites (Safety Analysis Set)

| | Plasma Concentrations (ng/mL) | | | |
|---|---|---|---|---|
| | | Metabolites | | |
| Statistic | Lemborexant | M4 | M9 | M10 |
| Month 1 | | | | |
| n | 296 | 296 | 296 | 296 |
| BLQ (<0.0500 ng/mL), n (%) | 31 (10.5) | 34 (11.5) | 35 (11.8) | 32 (10.8) |
| Mean (SD) | 9.0 (7.35) | 2.8 (1.87) | 1.6 (1.07) | 5.1 (3.49) |
| Median | 7.6 | 2.7 | 1.5 | 4.8 |
| Min, Max | 0.0, 47.1 | 0.0, 11.0 | 0.0, 6.2 | 0.0, 17.0 |
| Month 3 | | | | |
| n | 269 | 269 | 269 | 269 |
| BLQ (<0.0500 ng/mL), n (%) | 34 (12.6) | 36 (13.4) | 38 (14.1) | 34 (12.6) |
| Mean (SD) | 8.4 (6.04) | 2.7 (1.77) | 1.5 (1.00) | 4.9 (3.24) |
| Median | 7.7 | 2.8 | 1.5 | 4.9 |
| Min, Max | 0.0, 31.9 | 0.0, 8.8 | 0.0, 4.6 | 0.0, 15.8 |
| Month 6 | | | | |
| n | 247 | 247 | 247 | 247 |
| BLQ (<0.0500 ng/mL), η (%) | 45 (18.2) | 48 (19.4) | 50 (20.2) | 45 (18.2) |
| Mean (SD) | 7.9 (6.62) | 2.5 (1.91) | 1.4 (1.07) | 4.6 (3.57) |
| Median | 6.9 | 2.4 | 1.5 | 4.6 |
| Min, Max | 0.0, 37.8 | 0.0, 9.6 | 0.0, 5.8 | 0.0, 19.1 |

Lower limit of quantification for Lemborexant and its metabolites: 0.0500 ng/mL.
BLQ = below limit of quantification.

TABLE 10

Summary of Plasma Concentrations of Lemborexant (10 mg dose) and Lemborexant Metabolites (Safety Analysis Set)

| | Plasma Concentrations (ng/mL) | | | |
|---|---|---|---|---|
| | | Metabolites | | |
| Statistic | Lemborexant | M4 | M9 | M10 |
| Month 1 | | | | |
| n | 285 | 285 | 285 | 285 |
| BLQ (<0.0500 ng/mL), n (%) | 21 (7.4) | 24 (8.4) | 25 (8.8) | 22 (7.7) |
| Mean (SD) | 16.3 (11.50) | 5.3 (3.36) | 3.0 (1.82) | 9.9 (6.47) |
| Median | 15.1 | 5.3 | 3.0 | 9.8 |
| Min, Max | 0.0, 63.4 | 0.0, 19.8 | 0.0, 10.6 | 0.0, 35.8 |
| Month 3 | | | | |
| n | 258 | 258 | 258 | 258 |
| BLQ (<0.0500 ng/mL), n (%) | 29 (11.2) | 38 (14.7) | 38 (14.7) | 30 (11.6) |
| Mean (SD) | 15.6 (11.33) | 5.1 (3.49) | 2.9 (1.92) | 9.4 (6.63) |
| Median | 15.1 | 5.2 | 3.0 | 10.1 |
| Min, Max | 0.0, 48.4 | 0.0, 15.9 | 0.0, 8.9 | 0.0, 37.0 |
| Month 6 | | | | |
| n | 226 | 226 | 226 | 226 |
| BLQ (<0.0500 ng/mL), n (%) | 33 (14.6) | 34 (15.0) | 37 (16.4) | 34 (15.0) |
| Mean (SD) | 15.2 (13.14) | 5.0 (3.73) | 2.8 (2.10) | 9.3 (7.48) |
| Median | 14.5 | 5.1 | 2.8 | 9.2 |
| Min, Max | 0.0, 105.0 | 0.0, 17.7 | 0.0, 11.9 | 0.0, 35.6 |

Lower limit of quantification for Lemborexant and its metabolites: 0.0500 ng/mL.
BLQ = below limit of quantification.

TABLE 11

| Overview of Treatment-Emergent Adverse Events (Safety Analysis Set). | | | |
|---|---|---|---|
| Category | Placebo (N = 319) n (%) | Lemborexant 5 mg (N = 314) n (%) | Lemborexant 10 mg (N = 314) n (%) |
| TEAEs | 200 (62.7) | 192 (61.1) | 187 (59.6) |
| Treatment-related TEAEs | 44 (13.8) | 78 (24.8) | 91 (29.0) |

TABLE 11-continued

Overview of Treatment-Emergent Adverse Events (Safety Analysis Set).

| Category | Placebo (N = 319) n (%) | Lemborexant 5 mg (N = 314) n (%) | Lemborexant 10 mg (N = 314) n (%) |
|---|---|---|---|
| Severe TEAEs | 10 (3.1) | 13 (4.1) | 8 (2.5) |
| Serious TEAEs | 5 (1.6) | 7 (2.2) | 9 (2.9) |
| Deaths | 0 | 0 | 0 |
| Other SAEs | 5 (1.6) | 7 (2.2) | 9 (2.9) |
| Life threatening | 0 | 0 | 0 |
| Requires inpatient hospitalization or prolongation of existing hospitalization | 5 (1.6) | 6 (1.9) | 9 (2.9) |
| Persistent or significant disability or incapacity | 0 | 0 | 0 |
| Congenital anomaly/birth defect | 0 | 0 | 0 |
| Important medical events | 0 | 1 (0.3) | 0 |
| TEAEs leading to study drug dose adjustment | 18 (5.6) | 25 (8.0) | 33 (10.5) |
| TEAEs leading to study drug withdrawal | 12 (3.8) | 13 (4.1) | 26 (8.3) |
| TEAEs leading to study dose reduced | 0 | 0 | 0 |
| TEAEs leading to study drug interrupted | 7 (2.2) | 13 (4.1) | 8 (2.5) |

TEAE = treatment-emergent adverse event.
SAE = serious adverse event

Table 11 shows that lemborexant is a safe and well-tolerated drug, as indicated by the low incidence of adverse events. There were no deaths reported during this study.

Example 2. Treatment of Subjects Having Insomnia Disorder

Subjects, both male and female, age 55 and older, were screened to be eligible for treatment. 1006 subjects were randomized for treatment. The demographic information of the subject population is shown in Table 12.

TABLE 12

Demographics of Study Subjects (Full Analysis Set).

| | | Zolpidem ER | Lemborexant | | Combined |
|---|---|---|---|---|---|
| Category | Placebo (N = 208) | 6.25 mg (N=263) | 5 mg (N = 266) | 10 mg (N = 269) | Total (N = 1006) |
| **Age** | | | | | |
| Mean (SD) | 63.4 (6.36) | 64.3 (7.12) | 63.7 (6.78) | 64.2 (6.88) | 63.9 (6.81) |
| Median | 62.0 | 63.0 | 63.0 | 64.0 | 63.0 |
| Min, Max | 55, 82 | 55, 83 | 55, 88 | 55, 85 | 55, 88 |
| 55 to <65 years (%) | 115 (55.3) | 143 (54.4) | 148 (55.6) | 147 (54.6) | 553 (55.0) |
| >= 65 years (%) | 92 (44.7) | 120 (45.6) | 118 (44.4) | 122 (45.4) | 453 (45.0) |
| **Sex** | | | | | |
| Male (%) | 24 (11.5) | 37 (14.1) | 37 (13.9) | 39 (14.5) | 137 (13.6) |
| Female (%) | 184 (88.5) | 226 (85.9) | 229 (86.1) | 230 (85.5) | 869 (86.4) |

This study consisted of a prerandomization phase and a randomization phase.

Prerandomization Phase

The prerandomization phase consisted of three periods: a screening period, a run-in period, and a baseline period.

Screening Period

The screening period began no more than 35 days before the subject was randomized. Once informed consent was obtained, a medical, psychiatric, and sleep history interview was conducted, which included confirmation that the subject met diagnostic criteria for insomnia disorder and that the subject complained of difficulties with sleep maintenance or early morning awakening, or both. The screening assessments conducted were the Insomnia Sleep Index (ISI), the Epworth Sleepiness Scale (ESS), the STOPBang Sleep Apnea Questionnaire, the International Restless Legs Scale (IRLS), and the Munich Parasomnia Scale (MUPS). These assessments are collectively referred to as the Sleep Disorders Screening Battery.

Subjects were provided with a sleep diary and trained on how to record entries. After subjects completed the sleep diary on 7 consecutive mornings, and provided that the subject was still eligible to participate in the study, they attended a second clinical meeting between 10 and 17 days before the randomization phase. The subject was then fitted with a polysomnogram and trained in how to complete the postural stability assessment and cognitive performance assessment battery. Subjects then underwent an 8-hour polysomnogram recording. Within 5 minutes of waking, the postural stability assessment and cognitive assessment battery were conducted on the subject.

If subjects were still eligible to participate, they were dispensed placebo tablets and the run-in period began.

Run-In Period

The run-in period began when eligible subjects were dispensed placebo tablets and continued until the baseline period on day 1. During the run-in period, subjects took placebo each night within 5 minutes before bedtime and subjects remained in bed for at least 7 hours.

Once subjects had completed sleep diary entries on at least consecutive mornings during this period, the eligibility of the subject was again reviewed. If eligible, subjects returned to the clinic for the first of 2 nights on which polysomnography was to be conducted. The insomnia Severity Index, FSS, and EQ-5D-3L were also assessed. Study drug was then administered to subjects within 5 minutes of their scheduled bedtime. Subjects then underwent an 8-hour polysomnogram. After waking, the postural and cognitive battery assessments were conducted and the sleep diary was completed. Subjects were then free to leave the clinic for the day, before returning to repeat for another night.

Subjects were then allowed to return home and took study drug consistent with the procedure at the clinic. After a minimum of 2 nights, the run-in period ended.

Baseline Period

On day 1 of the baseline period, subjects were admitted to the clinic and ISI, FSS, and EQ-5D-3L were administered. Blood and urine samples were collected for routine safety assessments, an ECG was performed, and vital signs and weight were assessed. The eC-SSRS was administered. Subjects who completed the baseline period and continued to meet the eligibility criteria were randomized and began the randomization phase.

Randomization Phase

The randomization phase consisted of a treatment period and a follow-up period.

Treatment Period

The treatment period lasted for 31 days. Subjects were randomized in a double-blind manner and received placebo, a tablet containing 5 mg of lemborexant, a tablet containing 10 mg of lemborexant, or a tablet containing 6.25 mg of zolpidem ER.

Within 5 minutes of the subject's mean habitual bedtime, study drug was administered and an overnight polysomnogram recording was initiated. At completion of the recording the following morning (Day 2), postural stability and cognitive performance were assessed. On the Day 2 evening, subjects returned to the clinic and a blood sample was collected before administering study drug, and then study drug was administered within 5 minutes of the subject's mean habitual bedtime. Again, a polysomnogram recording was initiated. The next morning (Day 3), postural stability and cognitive performance were assessed. A blood sample was also collected.

Subjects then completed their sleep diary. An eC-SSRS was conducted. Within 1.5 hours of waking, subjects rated their morning sleepiness level. The subject was allowed to leave the clinic once a clinician deemed it safe for the subject to do so.

Once home, the subject ingested study drug each night prior to bedtime and completed their sleep diary within 1 hour of waketime.

On Day 29, subjects returned to the clinic. Study drug was administered within 5 minutes of the subject's mean habitual bedtime and a polysomnogram recording was conducted. On the following morning (Day 30), postural stability and cognitive performance were assessed. After 1.5 hours of waketime, subjects rated their morning sleepiness level.

On the evening of Day 30, subjects returned to the clinic. A pre-dose blood sample was collected and study drug was again administered within 5 minutes of the subject's mean habitual bedtime. A polysomnogram recording was initiated. The following morning (Day 31), postural stability and cognitive performance were assessed and a blood sample was obtained. The ISI, FSS, EQ-5D-3L and PGI-Insomnia were administered. Blood and urine samples were collected for routine safety assessment. An electrocardiogram was performed, and vital signs and weight were assessed. The eC-SSRS was then administered to the subject. At 1.5 hours after waketime, subjects rated their morning sleepiness level.

Follow-Up Period

The follow-up period began when the subjects left the clinic at the end of the treatment period. Subjects ceased to take study drug but continued to complete their sleep diary each morning until the end of study visit.

Between 14 and 18 days after completion of the treatment period, subjects returned to the clinic for the end of study visit. The T-BWSQ and eC-SSRS were administered and routine safety assessments were conducted.

Study Discontinuation

A subject who prematurely discontinued taking study drug was to return to the clinic as soon as practicable after discontinuing study drug. If the subject discontinued due to an adverse event, the adverse event must have been followed to resolution or for 2 weeks, whichever came first. Additionally, subjects who discontinued early underwent a urine drug test.

Study Drug

Subjects were administered two tablets each day according to the treatment group to which the subject was randomized:

- 5 mg lemborexant treatment group: 1 zolpidem ER-matched placebo tablet and 1 lemborexant 5 mg tablet.
- 10 mg lemborexant treatment group: 1 zolpidem ER-matched placebo tablet and 1 lemborexant 10 mg tablet.
- zolpidem ER 6.25 mg: 1 zolpidem ER 6.25 mg tablet and 1 lemborexant-matched placebo tablet.
- placebo: 1 zolpidem ER-matched placebo tablet and 1 lemborexant-matched placebo tablet.

Study Endpoints

The study had a primary endpoint, several key secondary endpoints, and a number of additional secondary endpoints.

Primary Endpoint

The primary endpoint was to determine the change from baseline for mean latency to persistent sleep on days 29 and 30 of 5 mg or 10 mg lemborexant compared to placebo.

Key Secondary Endpoints

One key secondary endpoint was to determine the change from baseline for mean sleep efficiency on Days 29 and 30 after administration of 5 mg or 10 mg of lemborexant, compared to placebo.

Another key secondary endpoint was to determine the change from baseline for mean wake after sleep onset on Days 29 and 30 after administration of 5 mg or 10 mg of lemborexant, compared to placebo.

Another key secondary endpoint was to determine the change from baseline for mean wake after sleep onset in the second half of the night on Days 29 and 30 after administration of 5 mg or 10 mg of lemborexant compared to administration of 6.25 mg of zolpidem ER.

An exemplary additional secondary endpoint is the change from baseline on the postural stability test of mean units of body sway on Days 2 and 3 after administration of 5 mg or 10 mg of lemborexant compared to zolpidem.

Inclusion Criteria

Subjects were eligible for participation in the study if they met all of the following inclusion criteria:

- Males age 65 years or older, or females age 55 years or older, at the time of informed consent.
- Met the Diagnostic and Statistical Manual of Mental Disorders, Fifth Edition, criteria for Insomnia Disorder:
  - i. Complained of dissatisfaction with night time sleep, in the form of difficulty staying asleep and/or awakening earlier in the morning than desired despite adequate opportunity to sleep.
  - ii. Frequency of complaint 3 or more times per week.
  - iii. Duration of complaint greater than or equal to 3 months.
  - iv. Associated with complaint of daytime impairment.
- At screening: history of sWASO typically greater than or equal to 60 minutes on at least 3 nights per week in the previous 4 weeks.
- At screening: reported regular time spent in bed, either sleeping or trying to sleep, between 7 and 9 hours.
- At screening: reported habitual bedtime, defined as the time the subject attempted to sleep, between 21:00 and 24:00 and habitual waketime between 05:00 and 09:00.
- At screening and at check-in before the first polysomnogram during the run-in period: ISI score greater than or equal to 13.
- Confirmation of current insomnia symptoms as determined from response on the sleep diary on the 7 most recent mornings (minimum 5 of 7 for eligibility) before the second screening visit, such that sWASO was greater than or equal to 60 minutes on at least 3 of the 7 nights.
- Confirmation of regular bedtime and waketime as determined from responses on the sleep diary on the 7 most recent mornings before the second screening visit, such that neither bedtime (defined as the time the subject attempted to try to sleep), nor waketime (defined as the time the subject got out of bed for the day) deviated more than 1 hour on more than 2 nights from the calculated mean habitual bedtime or median habitual waketime, respectively, from the screening sleep diary entries.
- Confirmation of sufficient duration of time spent in bed, as determined from responses on the sleep diary on the 7 most recent mornings before the second screening visit, such that there were not more than 2 nights with time spent in bed duration less than 7 hours or greater than 10 hours.
- During the run-in period: reconfirmation of insomnia symptoms, as determined from responses on the sleep diary on the 7 most recent mornings before the first polysomnogram during the run-in period, such that sWASO was greater than or equal to 60 minutes on at least 3 of the 7 nights.
- During the run-in period: reconfirmation of regular bedtimes and waketimes as defined above.
- During the run-in period: reconfirmation of sufficient duration of time spent in bed as defined above.
- During the run-in period: objective polysomnogram evidence of insomnia as follows: WASO average greater than or equal to 60 minutes on the 2 consecutive polysomnograms, with neither night less than 45 minutes.
- Willing and able to comply with all aspects of the protocol, including staying in bed for at least 7 hours each night.
- Willing not to start a behavioral or other treatment program for the treatment of insomnia during the subject's participation in the study.

Exclusion Criteria

Subjects were not eligible for participation in the study if they met any of the following exclusion criteria:

- Had a current diagnosis of sleep-related breathing disorder (including obstructive sleep apnea with or without continuous positive airway pressure treatment), periodic limb movement disorder, restless legs syndrome, circadian rhythm sleep disorder, or narcolepsy, or an exclusionary score on screening instruments to rule out individuals with symptoms of certain sleep disorders other than insomnia as follows:
  - i. STOPBang Sleep Apnea Questionnaire score greater than or equal to 5.
  - ii. IRLS score greater than or equal to 16.
  - iii. ESS score greater than 15 (scores of 11 to 15 required excessive daytime sleepiness to be recorded in subject's medical history).
- Reported symptoms potentially related to narcolepsy that, in the clinical opinion of the investigator, indicated the need for referral for a diagnostic evaluation for the presence of narcolepsy.
- On the MUPS, endorsed the item that corresponds to a history of sleep-eating or reported a history of sleep-related violent behavior, sleep-driving or symptoms of another parasomnia that, in the investigator's opinion, made the subject unsuitable for the study.
- Apnea-Hypopnea Index greater than 15 or Periodic Limb Movement with Arousal Index greater than 15 as measured on the PSG at the second screening visit.

Beck Depression Inventory-II (BDI-II) score greater than 19 at screening.

Beck Anxiety Inventory (BAI) score greater than 15 at screening.

Habitually napped during the day more than 3 times per week.

Was a female of childbearing potential. (Note: All females were considered to be of childbearing potential unless they were postmenopausal (defined as amenorrheic for at least 12 consecutive months, were in the appropriate age group, and were postmenopausal without other known or suspected cause), or had been sterilized surgically (i.e., bilateral tubal ligation, total hysterectomy, or bilateral oophorectomy, all with surgery at least 1 month before dosing).

Excessive caffeine use that, in the opinion of the investigator, contributed to the subject's insomnia, or habitually consumed caffeine-containing beverages after 18:00 and was unwilling to forego caffeine after 18:00 for the duration of his or her participation in the study.

History of drug or alcohol dependency or abuse within approximately the previous 2 years.

Reported habitually consuming more than 14 drinks containing alcohol per week (females) or more than 21 drinks containing alcohol per week (males), or habitually consumed alcohol within the 3 hours before bedtime and was unwilling to limit alcohol intake to no more than 2 drinks per day or forego having alcohol within the 3 hours before bedtime for the duration of his or her participation in the study.

Known to be positive for human immunodeficiency virus.

Active viral hepatitis (B or C) as demonstrated by positive serology at screening.

A prolonged QT/QT interval corrected for heart rate by Fridericia's formula (QTcF) interval (QTcf>450 msec) as demonstrated by a repeated ECG at screening (repeated only if initial ECG indicated a QTCF interval>450 msec).

Had current evidence of clinically significant disease (eg, cardiac; respiratory including chronic obstructive pulmonary disease, acute and/or severe respiratory depression; gastrointestinal including severe hepatic impairment; renal including severe renal impairment; neurological including myasthenia gravis; psychiatric disease; malignancy within the past 5 years other than adequately treated basal cell carcinoma) or chronic pain that, in the opinion of the investigator, could have affected the subject's safety or interfered with the study assessments, including the ability to perform tasks on the cognitive PAB. Subjects for whom a sedating drug would have been contraindicated for safety reasons because of the subject's occupation or activities were also excluded.

Comorbid nocturia resulting in frequent need to get out of bed to use the bathroom during the night.

Any history of a medical or psychiatric condition that, in the opinion of the investigator, may have affected the subject's safety or interfered with the study assessments, including the ability to perform the PAB.

Any suicidal ideation with intent with or without a plan, at the time of or within 6 months before the eC-SSRS administration during the prerandomization phase (i.e., answering "yes" to question 4 or 5 on the Suicidal Ideation section of the eC-SSRS).

Any suicidal behavior in the past 10 years (per the Suicidal Behavior section of the eC-SSRS).

Scheduled for surgery during the study.

Used any prohibited prescription or over-the-counter concomitant medications within 1 week or 5 half-lifes, whichever was longer, before the first dose of study drug (run-in period).

Used any modality of treatment for insomnia, including cognitive behavioral therapy or marijuana within 1 week or 5 half-lives, whichever was longer, before the first dose of study drug (run-in period).

Failed treatment with suvorexant (efficacy or safety) following treatment with an appropriate dose and of adequate duration, in the opinion of the investigator.

Transmeridian travel across more than 3 time zones in the 2 weeks before screening, or between screening and baseline, or plans to travel across more than 3 time zones during the study.

Had a positive drug test at screening, run-in, or baseline, or was unwilling to refrain from use of recreational drugs during the study.

Hypersensitivity to the study drugs (lemborexant or zolpidem) or to their excipients.

Was currently enrolled in another clinical study or used any investigational drug or device within 30 days or 5 times the half-life, whichever was longer, preceding informed consent.

Previously participated in any clinical study of lemborexant.

Results

TABLE 13

Summary and Analysis of Change from Study Baseline for Latency to Persistent Sleep (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 208 | 262 | 266 | 269 |
| Mean (SD) | 43.89 (33.596) | 44.52 (38.349) | 44.86 (36.528) | 44.61 (32.986) |
| Median | 33.63 | 31.50 | 33.13 | 38.50 |
| Min, Max | 2.5, 267.0 | 0.5, 205.0 | 2.3, 264.0 | 2.0, 193.8 |
| Days 1/2 | | | | |
| n | 208 | 263 | 266 | 269 |
| Mean (SD) | 37.44 (32.464) | 31.87 (23.715) | 28.27 (24.410) | 25.13 (16.666) |
| Median | 27.25 | 27.00 | 21.63 | 21.75 |
| Min, Max | 1.5, 159.8 | 1.0, 144.0 | 0.0, 208.8 | 1.0, 91.8 |

TABLE 13-continued

Summary and Analysis of Change from Study Baseline for Latency to Persistent Sleep (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Change from Study Baseline at Days 1/2 | | | | |
| n | 208 | 262 | 266 | 269 |
| Mean (SD) | −6.45 (32.618) | −12.56 (32.506) | −16.59 (28.742) | −19.48 (31.809) |
| Median | −6.25 | −5.63 | −10.00 | −10.50 |
| Min, Max | −114.3, 116.5 | −172.5, 93.3 | −147.0, 63.5 | −174.3, 64.8 |
| LSM treatment ratio: Active/Placebo | — | 0.972 | 0.850 | 0.795 |
| P value | — | 0.6550 | 0.0092 | 0.0002 |
| LSM treatment ratio: Lemborexant/ Zolpidem | — | — | 0.874 | 0.818 |
| P value | — | — | 0.0218 | 0.0006 |
| Days 29/30 | | | | |
| n | 200 | 251 | 260 | 259 |
| Mean (SD) | 36.04 (32.090) | 37.11 (28.397) | 25.84 (24.253) | 22.75 (17.460) |
| Median | 25.75 | 28.50 | 18.75 | 19.25 |
| Min, Max | 0.0, 215.3 | 1.8, 148.8 | 0.0, 216.5 | 0.3, 122.0 |
| Change from Study Baseline at Days 29/30 | | | | |
| n | 200 | 250 | 260 | 260 |
| Mean (SD) | −7.93 (31.946) | −7.51 (35.065) | −19.53 (33.054) | −21.46 (32.436) |
| Median | −6.63 | −2.88 | −12.00 | −16.25 |
| Min, Max | −165.0, 109.3 | −165.0, 74.3 | −209.3, 75.0 | −176.8, 86.0 |
| LSM treatment ratio: Active/Placebo | — | 1.218 | 0.773 | 0.723 |
| P value | — | 0.0063 | 0.0003 | <0.0001 |
| LSM treatment ratio: Lemborexant/ Zolpidem | — | — | 0.634 | 0.594 |
| P value | — | — | <0.0001 | <0.0001 |

ER = extended release.
LSM = least squares mean.

As shown in Table 13, mean latency to persistent sleep was reduced for all lemborexant treatment groups, relative to baseline, placebo group, and zolpidem group.

TABLE 14

Summary and Analysis of Change from Study Baseline for Sleep Efficiency (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 208 | 262 | 266 | 269 |
| Mean (SD) | 68.89 (9.639) | 68.13 (11.419) | 68.36 (11.268) | 67.85 (10.849) |
| Median | 70.44 | 69.79 | 70.39 | 69.01 |
| Min, Max | 34.6, 85.4 | 20.1, 86.8 | 23.4, 86.3 | 34.0, 85.8 |
| Days 1/2 | | | | |
| n | 208 | 263 | 266 | 269 |
| Mean (SD) | 73.11 (10.772) | 79.85 (8.461) | 81.96 (8.384) | 84.33 (7.608) |
| Median | 75.36 | 80.73 | 83.62 | 85.73 |
| Min, Max | 41.0, 93.5 | 32.1, 97.1 | 39.4, 96.1 | 51.1, 96.8 |
| Change from Study Baseline at Days 1/2 | | | | |
| n | 208 | 262 | 266 | 269 |
| Mean (SD) | 4.22 (9.033) | 11.70 (9.725) | 13.60 (9.725) | 16.48 (9.623) |
| Median | 4.19 | 10.83 | 12.40 | 15.47 |

TABLE 14-continued

Summary and Analysis of Change from Study Baseline for Sleep Efficiency (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Min, Max | −26.8, 29.7 | −20.5, 52.4 | −27.4, 44.8 | −10.8, 52.1 |
| LSM treatment difference: Active-Placebo (SE) | — | 6.96 (0.669) | 9.01 (0.666) | 11.60 (0.664) |
| P value | — | <0.0001 | <0.0001 | <0.0001 |
| LSM treatment difference: Lemborexant-Zolpidem (SE) | — | — | 2.05 (0.625) | 4.64 (0.624) |
| P value | — | — | 0.0011 | <0.0001 |
| Days 29/30 | | | | |
| n | 200 | 251 | 260 | 260 |
| Mean (SD) | 74.49 (9.848) | 77.17 (10.185) | 81.29 (8.800) | 81.99 (8.801) |
| Median | 75.52 | 78.70 | 83.26 | 83.52 |
| Min, Max | 43.4, 96.4 | 34.0, 95.6 | 38.4, 94.8 | 32.1, 97.8 |
| Change from Study Baseline at Days 29/30 | | | | |
| n | 200 | 250 | 260 | 260 |
| Mean (SD) | 5.35 (9.897) | 9.06 (11.230) | 12.93 (9.741) | 14.09 (10.514) |
| Median | 5.31 | 8.39 | 11.85 | 13.57 |
| Min, Max | −29.6, 45.2 | −31.2, 41.2 | −15.5, 48.9 | −23.1, 51.5 |
| LSM treatment difference: Active-Placebo (SE) | — | 3.15 (0.754) | 7.07 (0.746) | 8.03 (0.746) |
| P value | — | <0.0001 | <0.0001 | <0.0001 |
| LSM treatment difference: Lemborexant-Zolpidem | — | — | 3.92 (0.705) | 4.88 (0.702) |
| P value | — | — | <0.0001 | <0.0001 |

ER = extended release.
LSM = least squares mean.
SE = standard error

As shown in Table 14, mean sleep efficiency was increased for all lemborexant treatment groups, relative to baseline, placebo treatment group, and zolpidem treatment group.

TABLE 15

Summary and Analysis of Change from Study Baseline for Wake After Sleep Onset (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 208 | 262 | 266 | 269 |
| Mean (SD) | 111.75 (37.179) | 114.31 (39.922) | 113.44 (38.953) | 114.83 (39.997) |
| Median | 105.88 | 107.25 | 105.50 | 107.50 |
| Min, Max | 60.0, 280.0 | 43.5, 286.8 | 60.3, 251.0 | 37.3, 249.5 |
| Days 1/2 | | | | |
| n | 208 | 263 | 266 | 269 |
| Mean (SD) | 96.67 (41.250) | 69.92 (33.517) | 63.48 (31.484) | 55.23 (30.486) |
| Median | 91.25 | 62.00 | 58.38 | 48.75 |
| Min, Max | 23.3, 259.0 | 10.3, 224.3 | 8.5, 245.0 | 11.8, 204.5 |
| Change from Study Baseline at Days 1/2 | | | | |
| n | 208 | 262 | 266 | 269 |
| Mean (SD) | −15.07 (36.938) | −44.36 (38.074) | −49.96 (39.578) | −59.59 (37.749) |
| Median | −15.75 | −44.13 | −46.75 | −54.50 |

TABLE 15-continued

Summary and Analysis of Change from Study Baseline for Wake After Sleep Onset (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Min, Max | −122.8, 121.3 | −182.8, 91.0 | −168.8, 113.3 | −195.8, 47.5 |
| LSM treatment difference: Active-Placebo (SE) | — | −27.24 (2.719) | −33.40 (2.711) | −42.27 (2.705) |
| P value | — | <0.0001 | <0.0001 | <0.0001 |
| LSM treatment difference: Lemborexant-Zolpidem (SE) | — | — | −6.16 (2.544) | −15.03 (2.542) |
| P value | — | — | 0.0154 | <0.0001 |
| Days 29/30 | | | | |
| n | 200 | 251 | 260 | 260 |
| Mean (SD) | 92.09 (40.965) | 77.71 (39.932) | 69.10 (34.533) | 68.60 (35.200) |
| Median | 90.88 | 71.00 | 62.63 | 62.50 |
| Min, Max | 12.8, 264.5 | 14.5, 266.8 | 13.8, 242.3 | 8.3, 187.3 |
| Change from Study Baseline at Days 29/30 | | | | |
| n | 200 | 250 | 260 | 260 |
| Mean (SD) | −18.58 (41.931) | −36.50 (43.406) | −43.89 (39.264) | −46.43 (36.595) |
| Median | −16.75 | −34.63 | −39.50 | −46.50 |
| Min, Max | −161.8, 140.5 | −161.0, 129.8 | −216.3, 77.8 | −174.8, 66.0 |
| LSM treatment difference: Active-Placebo (SE) | — | −16.25 (3.094) | −23.96 (3.068) | −25.35 (3.067) |
| P value | — | <0.0001 | <0.0001 | <0.0001 |
| LSM treatment difference: Lemborexant-Zolpidem | — | — | −7.72 (2.876) | −9.10 (2.883) |
| P value | — | — | 0.0073 | 0.0016 |

ER = extended release.
LSM = least squares mean.
SE = standard error.

As shown in Table 15, mean wake after sleep onset was reduced for all lemborexant treatment groups, relative to baseline, placebo treatment group, and zolpidem treatment group.

TABLE 16

Summary and Analysis of Change from Study Baseline for Wake After Sleep Onset in the Second Half of the Night (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 208 | 262 | 266 | 269 |
| Mean (SD) | 74.44 (30.109) | 78.04 (33.849) | 76.60 (32.903) | 76.88 (32.126) |
| Median | 67.13 | 70.00 | 71.00 | 74.50 |
| Min, Max | 25.3, 183.3 | 15.5, 208.8 | 24.3, 205.3 | 8.8, 179.5 |
| Days 1/2 | | | | |
| n | 208 | 263 | 266 | 269 |
| Mean (SD) | 67.38 (32.892) | 53.30 (27.706) | 46.32 (25.600) | 39.78 (23.709) |
| Median | 63.00 | 49.25 | 40.88 | 34.00 |
| Min, Max | 7.3, 231.5 | 7.0, 156.8 | 5.0, 148.0 | 6.5, 141.8 |
| Change from Study Baseline at Days 1/2 | | | | |
| η | 208 | 262 | 266 | 269 |
| Mean (SD) | −7.06 (31.097) | −24.64 (33.347) | −30.28 (32.056) | −37.10 (30.815) |
| Median | −7.50 | −24.13 | −27.63 | −32.00 |
| Min, Max | −96.5, 119.5 | −169.8, 75.5 | −137.5, 59.8 | −131.5, 32.5 |
| LSM treatment difference: Active-Placebo (SE) | — | −15.20 (2.232) | −21.66 (2.221) | −28.33 (2.219) |

TABLE 16-continued

Summary and Analysis of Change from Study Baseline for Wake After Sleep Onset in the Second Half of the Night (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| P value | — | <0.0001 | <0.0001 | <0.0001 |
| LSM treatment difference: Lemborexant-Zolpidem (SE) | — | — | −6.46 (2.087) | −13.13 (2.084) |
| P value | — | — | 0.0020 | <0.0001 |
| Days 29/30 | | | | |
| n | 200 | 251 | 260 | 260 |
| Mean (SD) | 64.37 (32.445) | 56.74 (31.112) | 49.11 (28.179) | 48.15 (27.844) |
| Median | 59.88 | 51.25 | 42.13 | 41.75 |
| Min, Max | 3.3, 214.5 | 5.5, 172.0 | 9.8, 168.8 | 3.5, 139.8 |
| Change from Study Baseline at Days 29/30 | | | | |
| n | 200 | 250 | 260 | 260 |
| Mean (SD) | −8.92 (31.909) | −21.42 (36.257) | −27.19 (33.047) | 28.84 (33.138) |
| Median | −9.25 | −19.13 | −25.63 | −27.25 |
| Min, Max | −86.5, 105.8 | −134.8, 100.3 | −153.3, 80.5 | −129.0, 61.5 |
| LSM treatment difference: Active-Placebo (SE) | — | −9.76 (2.467) | −16.41 (2.457) | −17.76 (2.451) |
| P value | — | <0.0001 | <0.0001 | <0.0001 |
| LSM treatment difference: Lemborexant-Zolpidem | — | — | −6.65 (2.298) | −8.00 (2.309) |
| P value | — | — | 0.0038 | 0.0005 |

ER = extended release.
LSM = least squares mean.
SE = standard error.

As shown in Table 16, mean wake after sleep onset in the second half of the night was reduced for all lemborexant treatment groups, relative to baseline, placebo treatment group, and zolpidem treatment group.

TABLE 17

Summary and Analysis of Change from Study Baseline for Total Sleep Time (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 208 | 262 | 266 | 269 |
| Mean (SD) | 330.67 (46.268) | 326.99 (54.852) | 328.00 (54.224) | 325.07 (52.819) |
| Median | 338.13 | 335.00 | 337.88 | 330.50 |
| Min, Max | 166.0, 410.0 | 96.5, 416.5 | 112.5, 414.3 | 160.5, 412.0 |
| Days 1/2 | | | | |
| n | 208 | 263 | 266 | 269 |
| Mean (SD) | 350.11 (52.239) | 382.42 (41.528) | 393.22 (40.346) | 404.65 (36.593) |
| Median | 361.75 | 387.25 | 400.63 | 411.50 |
| Min, Max | 197.0, 448.8 | 154.3, 466.0 | 185.8, 461.3 | 245.3, 464.8 |
| Change from Study Baseline at Days 1/2 | | | | |
| n | 208 | 262 | 266 | 269 |
| Mean (SD) | 19.44 (43.348) | 55.31 (48.138) | 65.22 (46.695) | 79.58 (47.350) |
| Median | 18.38 | 52.00 | 59.50 | 74.25 |
| Min, Max | −128.5, 142.5 | −146.0, 251.5 | −131.8, 215.3 | −51.8, 277.8 |
| LSM treatment difference: Active-Placebo (SE) | — | 33.80 (3.302) | 44.05 (3.291) | 56.90 (3.284) |

TABLE 17-continued

Summary and Analysis of Change from Study Baseline for Total Sleep Time (Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| P value | — | <0.0001 | <0.0001 | <0.0001 |
| LSM treatment difference: Lemborexant-Zolpidem (SE) | — | — | 10.25 (3.094) | 23.10 (3.085) |
| P value | — | — | 0.0010 | <0.0001 |
| Days 29/30 | | | | |
| n | 200 | 251 | 260 | 260 |
| Mean (SD) | 357.48 (47.333) | 370.25 (48.855) | 389.97 (42.437) | 393.16 (42.827) |
| Median | 362.50 | 377.75 | 399.63 | 400.88 |
| Min, Max | 207.8, 462.5 | 163.0, 458.8 | 184.5, 455.0 | 154.0, 469.3 |
| Change from Study Baseline at Days 29/30 | | | | |
| n | 200 | 250 | 260 | 260 |
| Mean (SD) | 25.65 (47.587) | 43.34 (54.012) | 61.99 (46.817) | 67.86 (52.117) |
| Median | 25.50 | 39.63 | 56.50 | 65.13 |
| Min, Max | −142.3, 216.8 | −149.8, 197.8 | −74.5, 234.8 | −110.8, 253.3 |
| LSM treatment difference: Active-Placebo (SE) | — | 14.75 (3.701) | 34.16 (3.673) | 38.85 (3.672) |
| P value | — | <0.0001 | <0.0001 | <0.0001 |
| LSM treatment difference: Lemborexant-Zolpidem | — | — | 19.41 (3.457) | 24.10 (3.456) |
| P value | — | — | <0.0001 | <0.0001 |

ER = extended release.
LSM = least squares mean.
SE = standard error.

As shown in Table 17, mean total sleep time was increased for all lemborexant treatment groups, relative to baseline, placebo treatment group, and zolpidem treatment group.

TABLE 18

Summary and Analysis of Change from Study Baseline for Subjective Sleep Onset Latency (Full Analysis Set; with data handling rules).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 206 | 258 | 263 | 269 |
| Mean (SD) | 55.90 (37.389) | 60.54 (36.350) | 65.79 (43.530) | 60.88 (42.514) |
| Median | 49.29 | 53.21 | 58.57 | 53.57 |
| First 7 Nights of Treatment | | | | |
| n | 203 | 256 | 261 | 266 |
| Mean (SD) | 48.91 (31.641) | 44.61 (27.566) | 42.39 (28.075) | 38.64 (32.092) |
| Median | 38.10 | 34.29 | 29.64 | 411.50 |
| Min, Max | 197.0, 448.8 | 154.3, 466.0 | 185.8, 461.3 | 245.3, 464.8 |
| Change from Study Baseline: First 7 Nights of Treatment | | | | |
| n | 202 | 251 | 259 | 266 |
| Mean (SD) | −6.83 (23.040) | −16.23 (29.531) | −22.54 (32.812) | −21.88 (29.269) |
| Median | −2.86 | −10.00 | −14.86 | −15.00 |
| Statistical comparison with placebo (Rvalue) | — | 0.0347 | <0.0001 | <0.0001 |
| Statistical comparison with zolpidem (P value) | — | — | 0.0122 | <0.0001 |

TABLE 18-continued

Summary and Analysis of Change from Study Baseline for Subjective Sleep Onset Latency (Full Analysis Set; with data handling rules).

| | Placebo (N = 208) | Zolpidem ER 6.25 mg (N = 263) | Lemborexant 5 mg (N = 266) | Lemborexant 10 mg (N = 269) |
|---|---|---|---|---|
| Last 7 Nights of Treatment | | | | |
| n | 197 | 251 | 254 | 258 |
| Mean (SD) | 47.60 (32.765) | 43.64 (30.649) | 38.80 (28.028) | 36.51 (31.059) |
| Median | 38.57 | 37.50 | 30.36 | 27.50 |
| Change from Study Baseline: Last 7 Nights of Treatment | | | | |
| n | 196 | 246 | 252 | 258 |
| Mean (SD) | −8.10 (27.447) | −17.04 (30.683) | −25.20 (34.854) | −24.79 (34.068) |
| Median | −4.00 | −10.71 | −18.54 | −17.14 |
| Statistical comparison with placebo (Rvalue) | — | 0.0039 | <0.0001 | <0.0001 |
| Statistical comparison with zolpidem (P value) | — | — | 0.0176 | <0.0001 |

ER = extended release.
SD = standard deviation.

As shown in Table 18, mean subjective sleep onset latency was reduced for all lemborexant treatment groups, relative to baseline, placebo treatment group, and zolpidem treatment group.

TABLE 19

Summary and Analysis of Change from Study Baseline for Subjective Sleep Efficiency (Full Analysis Set; with data handling rules).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 201 | 247 | 253 | 258 |
| Mean (SD) | 56.08 (17.343) | 55.49 (15.802) | 56.05 (17.094) | 54.31 (18.318) |
| First 7 Nights of Treatment | | | | |
| n | 201 | 254 | 260 | 263 |
| Mean (SD) | 62.45 (17.575) | 66.45 (16.419) | 65.96 (18.203) | 68.10 (18.356) |
| Change from Study Baseline: First 7 Nights of Treatment | | | | |
| n | 197 | 240 | 251 | 254 |
| Mean (SD) | 6.73 (10.930) | 11.96 (12.526) | 10.56 (12.296) | 13.97 (14.188) |
| Model-adjusted change from baseline | 6.97 | 12.11 | 10.74 | 13.81 |
| Statistical comparison with placebo (Rvalue) | — | <0.0001 | 0.0008 | <0.0001 |
| Statistical comparison with zolpidem (P value) | — | — | 0.1963 | 0.1093 |
| Last 7 Nights of Treatment | | | | |
| n | 195 | 250 | 254 | 252 |
| Mean (SD) | 63.96 (19.249) | 69.45 (16.925) | 68.19 (19.251) | 69.92 (19.098) |
| Change from Study Baseline: Last 7 Nights of Treatment | | | | |
| n | 190 | 235 | 245 | 244 |
| Mean (SD) | 8.35 (13.273) | 14.83 (15.011) | 12.92 (13.884) | 16.12 (16.3000) |
| Model-adjusted change from baseline | 8.69 | 14.82 | 13.29 | 15.87 |
| Statistical comparison with placebo (Rvalue) | — | <0.0001 | 0.0005 | <0.0001 |

TABLE 19-continued

Summary and Analysis of Change from Study Baseline for Subjective Sleep Efficiency (Full Analysis Set; with data handling rules).

| | Placebo (N = 208) | Zolpidem ER 6.25 mg (N = 263) | Lemborexant 5 mg (N = 266) | Lemborexant 10 mg (N = 269) |
|---|---|---|---|---|
| Statistical comparison with zolpidem (P value) | — | — | 0.2196 | 0.4013 |

ER = extended release.
SD = standard deviation.

As shown in Table 19, mean subjective sleep efficiency was increased for the 10 mg lemborexant treatment group, relative to baseline, placebo treatment group, and zolpidem treatment group.

TABLE 20

Summary and Analysis of Change from Study Baseline for Subjective Wake After Sleep Onset (Full Analysis Set; with data handling rules).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 206 | 259 | 264 | 266 |
| Mean (SD) | 170.89 (80.676) | 173.06 (77.212) | 166.76 (82.047) | 175.35 (83.453) |
| First 7 Nights of Treatment | | | | |
| n | 203 | 257 | 262 | 264 |
| Mean (SD) | 143.53 (80.566) | 124.83 (75.279) | 127.37 (78.303) | 119.78 (74.825) |
| Change from Study Baseline: First 7 Nights of Treatment | | | | |
| n | 202 | 253 | 261 | 262 |
| Mean (SD) | −27.92 (45.201) | −48.91 (51.761) | −39.33 (55.022) | −55.06 (66.696) |
| Model-adjusted change from baseline | −27.56 | −48.09 | −39.97 | −53.90 |
| Statistical comparison with placebo (Rvalue) | — | <0.0001 | 0.0093 | <0.0001 |
| Statistical comparison with zolpidem (P value) | — | — | 0.0706 | 0.1949 |
| Last 7 Nights of Treatment | | | | |
| n | 197 | 251 | 254 | 255 |
| Mean (SD) | 135.85 (85.009) | 109.63 (72.583) | 119.30 (81.645) | 117.08 (83.753) |
| Change from Study Baseline: Last 7 Nights of Treatment | | | | |
| n | 196 | 247 | 253 | 253 |
| Mean (SD) | −36.01 (57.584) | −63.52 (64.161) | −44.51 (58.090) | −57.96 (72.791) |
| Model-adjusted change from baseline | −36.06 | −62.00 | −47.55 | −56.64 |
| Statistical comparison with placebo (Rvalue) | — | <0.0001 | 0.0396 | 0.0002 |
| Statistical comparison with zolpidem (P value) | — | — | 0.0059 | 0.3064 |

ER = extended release.
SD = standard deviation.

As shown in Table 20, mean subjective wake after sleep onset was reduced for the 10 mg lemborexant treatment group, relative to baseline, placebo treatment group, and zolpidem treatment group.

TABLE 21

Summary and Analysis of Change from Study Baseline for Subjective Total Sleep Time (Full Analysis Set; with data handling rules).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 201 | 247 | 253 | 258 |
| Mean (SD) | 276.23 (87.649) | 273.07 (81.207) | 275.74 (83.650) | 266.10 (92.164) |
| First 7 Nights of Treatment | | | | |
| n | 201 | 254 | 260 | 263 |
| Mean (SD) | 305.35 (89.780) | 325.64 (81.845) | 322.66 (89.706) | 332.92 (91.538) |
| Change from Study Baseline: First 7 Nights of Treatment | | | | |
| n | 197 | 240 | 251 | 254 |
| Mean (SD) | 30.86 (57.437) | 56.99 (62.880) | 50.30 (60.065) | 67.80 (71.134) |
| Model-adjusted change from baseline | 32.09 | 57.71 | 51.14 | 66.59 |
| Statistical comparison with placebo (Rvalue) | — | <0.0001 | 0.0007 | <0.0001 |
| Statistical comparison with zolpidem (P value) | — | — | 0.2174 | 0.0949 |
| Last 7 Nights of Treatment | | | | |
| n | 195 | 250 | 254 | 252 |
| Mean (SD) | 312.53 (95.869) | 340.20 (83.582) | 334.22 (94.339) | 343.68 (95.785) |
| Change from Study Baseline: Last 7 Nights of Treatment | | | | |
| n | 190 | 235 | 245 | 244 |
| Mean (SD) | 38.98 (66.174) | 71.01 (76.574) | 62.41 (68.555) | 79.95 (81.211) |
| Model-adjusted change from baseline | 40.65 | 71.04 | 64.22 | 78.47 |
| Statistical comparison with placebo (Rvalue) | — | <0.0001 | 0.0003 | <0.0001 |
| Statistical comparison with zolpidem (P value) | — | — | 0.2718 | 0.2317 |

ER = extended release.
SD = standard deviation.

As shown in Table 21, mean subjective total wake time was increased for the 10 mg lemborexant treatment group, relative to baseline, placebo treatment group, and zolpidem treatment group.

TABLE 22

Summary and Analysis of Change from Study Baseline for Insomnia Severity Total Score (Items 1-7; Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 208 | 263 | 266 | 269 |
| Mean (SD) | 19.38 (3.587) | 19.22 (3.519) | 18.91 (3.494) | 18.98 (3.262) |
| Median | 19.00 | 19.00 | 19.00 | 19.00 |
| Min, Max | 9.0, 28.0 | 9.0, 28.0 | 10.0, 28.0 | 10.0, 28.0 |
| Day 31 | | | | |
| n | 198 | 244 | 257 | 253 |
| Mean (SD) | 13.31 (5.419) | 10.98 (5.452) | 11.24 (5.387) | 11.11 (5.639) |

TABLE 22-continued

Summary and Analysis of Change from Study Baseline for Insomnia Severity Total Score (Items 1-7; Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Median | 14.00 | 11.00 | 11.00 | 11.00 |
| Min, Max | 0.0, 28.0 | 0.0, 28.0 | 0.0, 26.0 | 0.0, 28.0 |
| Change from Study Baseline at Day 31 | | | | |
| n | 198 | 244 | 257 | 253 |
| Mean (SD) | −6.08 (5.547) | −8.26 (6.013) | −7.75 (5.474) | −7.92 (5.894) |
| Median | −5.50 | −8.00 | −7.00 | −7.00 |
| Min, Max | −27.0, 6.0 | −25.0, 15.0 | −23.0, 6.0 | −23.0, 4.0 |
| LSM treatment difference: Active-Placebo (SE) | — | −2.30 (0.509) | −1.94 (0.503) | −2.08 (0.505) |
| P value | — | <0.0001 | 0.0001 | <0.0001 |
| LSM treatment difference: Lemborexant-Zolpidem (SE) | — | — | 0.36 (0.475) | 0.22 (0.477) |
| P value | — | — | 0.4466 | 0.6412 |

SE = standard error.
LSM = least squares mean.

As shown in Table 22, mean insomnia severity index total score was reduced for the lemborexant treatment groups, relative to baseline and the placebo treatment group.

TABLE 23

Summary and Analysis of Change from Study Baseline for Insomnia Severity Daytime Functioning (Items 4-7; Full Analysis Set).

| | Placebo (N = 208) | Zolpidem ER 6.25 mg (N = 263) | Lemborexant 5 mg (N = 266) | Lemborexant 10 mg (N = 269) |
|---|---|---|---|---|
| Study Baseline | | | | |
| n | 208 | 263 | 266 | 269 |
| Mean (SD) | 11.21 (2.436) | 11.06 (2.508) | 10.91 (2.419) | 10.84 (2.334) |
| Median | 11.00 | 11.00 | 11.00 | 11.00 |
| Min, Max | 4.0, 16.0 | 4.0, 16.0 | 4.0, 16.0 | 4.0, 16.0 |
| Day 31 | | | | |
| n | 198 | 244 | 257 | 253 |
| Mean (SD) | 7.30 (3.557) | 5.87 (3.417) | 6.12 (3.488) | 6.10 (3.617) |
| Median | 8.00 | 6.00 | 6.00 | 6.00 |
| Min, Max | 0.0, 16.0 | 0.0, 16.0 | 0.0, 16.0 | 0.0, 16.0 |
| Change from Study Baseline at Day 31 | | | | |
| n | 198 | 244 | 257 | 253 |
| Mean (SD) | −3.88 (3.559) | −5.24 (3.764) | −4.83 (3.593) | −4.77 (3.735) |
| Median | −4.00 | −5.00 | −4.00 | −4.00 |
| Min, Max | −16.0, 3.0 | −16.0, 3.0 | −15.0, 4.0 | −14.0, 4.0 |
| LSM treatment difference: Lemborexant-Placebo (SE) | — | −1.42 (0.322) | −1.10 (0.319) | −1.08 (0.320) |
| P value | — | <0.0001 | 0.0006 | 0.0007 |
| LSM treatment difference: Active-Zolpidem (SE) | — | — | 0.32 (0.301) | 0.33 (0.303) |
| P value | — | — | 0.2951 | 0.2744 |

SD = standard deviation.
SE = standard error.
LSM = least squares mean.

As shown in Table 23, mean insomnia severity index daytime score was reduced for the lemborexant treatment groups, relative to baseline and the placebo treatment group.

TABLE 24

Summary and Analysis of Change from Study Baseline for Body Sway Upon Awakening in Morning (extreme values removed; Full Analysis Set).

| | Placebo (N = 208) | Zolpidem ER 6.25 mg (N = 262) | Lemborexant 5 mg (N = 266) | Lemborexant 10 mg (N = 268) |
|---|---|---|---|---|
| Study Baseline | | | | |
| n | 199 | 238 | 245 | 242 |
| Mean (SD) | 23.08 (17.506) | 26.01 (22.130) | 26.40 (20.781) | 23.69 (19.515) |
| Median | 19.00 | 22.00 | 21.50 | 19.00 |
| Min, Max | 0.0, 110.5 | 1.0, 173.0 | 1.0, 142.5 | 1.0, 128.0 |
| Days 2/3 | | | | |
| n | 192 | 237 | 240 | 237 |
| Mean (SD) | 20.81 (14.587) | 29.86 (25.252) | 25.73 (23.424) | 24.36 (20.105) |
| Median | 18.00 | 25.00 | 21.00 | 20.00 |
| Min, Max | 0.0, 77.0 | 0.0, 189.5 | 0.0, 199.5 | 0.5, 119.0 |
| Change from Study Baseline at Days 2/3 | | | | |
| n | 190 | 233 | 237 | 233 |
| Mean (SD) | −2.02 (13.660) | 4.07 (18.919) | −0.82 (20.383) | 0.56 (17.081) |
| Median | −0.25 | 2.50 | −0.50 | 0.50 |
| Min, Max | −79.5, 35.0 | −107.0, 99.0 | −90.5, 144.5 | −80.5, 78.5 |
| LSM treatment difference: Active-Placebo (SE) | — | 7.20 (1.629) | 2.49 (1.624) | 2.91 (1.627) |
| P value | — | <0.0001 | 0.1258 | 0.0741 |
| LSM treatment difference: Active-Zolpidem (SE) | — | — | −4.71 (1.536) | −4.29 (1.544) |
| P value | — | — | 0.0022 | 0.0055 |
| Days 30/31 | | | | |
| n | 160 | 195 | 210 | 204 |
| Mean (SD) | 22.19 (18.143) | 27.65 (21.849) | 25.10 (19.635) | 22.76 (20.054) |
| Median | 17.25 | 22.50 | 20.50 | 18.00 |
| Min, Max | 0.0, 114.5 | 1.0, 143.5 | 0.5, 144.5 | 0.5, 154.5 |
| Change from Baseline at Days 30/31 | | | | |
| n | 160 | 192 | 208 | 201 |
| Mean (SD) | 1.68 (16.577) | 2.12 (18.359) | −0.85 (16.202) | 0.48 (14.853) |
| Median | 0.50 | 2.50 | −0.50 | 0.50 |
| Min, Max | −61.0, 107.0 | −126.5, 53.0 | −102.5, 57.0 | −88.0, 45.0 |
| LSM treatment difference: Active-Placebo (SE) | — | 1.99 (1.601) | −0.72 (1.576) | −0.58 (1.583) |
| P value | — | 0.2136 | 0.6528 | 0.7161 |
| LSM treatment difference: Active-Zolpidem (SE) | — | — | −2.70 (1.496) | −2.57 (1.509) |
| P value | — | — | 0.0716 | 0.0890 |

SD = standard deviation.
SE = standard error.
LSM = least squares mean.
Body sway is reported in units of ⅓ degree angle of arc.

As shown in Table 24, body sway was reduced for all lemborexant treatment groups, relative to baseline, placebo treatment group, and zolpidem treatment group. Lemborexant had no significant effects on postural stability compared to placebo.

TABLE 25

Summary of Plasma Concentrations of Lemborexant (5 mg dose) and Lemborexant Metabolites (Safety Analysis Set, N = 257).

| | Plasma Concentrations (ng/mL) | | | |
|---|---|---|---|---|
| | | Metabolites | | |
| Statistic | Lemborexant | M4 | M9 | M10 |
| Day 2 Pre-Dose | | | | |
| n | 257 | 257 | 257 | 257 |
| BLQ (<0.0500 ng/mL), n (%) | 10 (3.9) | 10 (3.9) | 10 (3.9) | 10 (3.9) |
| Mean (SD) | 2.1 (1.48) | 1.0 (0.62) | 0.5 (0.29) | 1.3 (0.65) |
| Median | 1.8 | 0.9 | 0.5 | 1.2 |
| Min, Max | 0.0, 12.8 | 0.0, 4.0 | 0.0, 1.9 | 0.0, 5.6 |
| Day 2 Post-Dose | | | | |
| n | 256 | 256 | 256 | 256 |
| BLQ (<0.0500 ng/mL), n (%) | 6 (2.3) | 6 (2.3) | 6 (2.3) | 6 (2.3) |
| Mean (SD) | 5.3 (2.55) | 2.7 (0.97) | 1.3 (0.54) | 2.8 (1.08) |
| Median | 5.0 | 2.6 | 1.3 | 2.9 |
| Min, Max | 0.0, 15.9 | 0.0, 6.0 | 0.0, 4.2 | 0.0, 6.6 |
| Day 29 Pre-Dose | | | | |
| n | 254 | 254 | 254 | 254 |
| BLQ (<0.0500 ng/mL), n (%) | 8 (3.1) | 8 (3.1) | 8 (3.1) | 8 (3.1) |
| Mean (SD) | 7.3 (5.60) | 2.2 (1.32) | 1.4 (0.79) | 4.5 (2.60) |
| Median | 6.1 | 1.9 | 1.3 | 3.9 |
| Min, Max | 0.0, 56.3 | 0.0, 8.0 | 0.0, 4.8 | 0.0, 13.7 |
| Day 29 Post-Dose | | | | |
| n | 254 | 254 | 254 | 254 |
| BLQ (<0.0500 ng/mL), n (%) | 6 (2.4) | 6 (2.4) | 6 (2.4) | 6 (2.4) |
| Mean (SD) | 10.7 (6.66) | 3.8 (1.52) | 2.1 (0.96) | 5.9 (2.91) |
| Median | 9.1 | 3.6 | 1.9 | 5.5 |
| Min, Max | 0.0, 64.0 | 0.0, 8.7 | 0.0, 6.5 | 0.0, 15.8 |

Lower limit of quantification for Lemborexant and its metabolites: 0.0500 ng/mL.
BLQ = below limit of quantification.

TABLE 26

Summary of Plasma Concentrations of Lemborexant (10 mg dose) and Lemborexant Metabolites (Safety Analysis Set, N = 258).

| | Plasma Concentrations (ng/mL) | | | |
|---|---|---|---|---|
| | | Metabolites | | |
| Statistic | Lemborexant | M4 | M9 | M10 |
| Day 2 Pre-Dose | | | | |
| n | 258 | 258 | 258 | 258 |
| BLQ (<0.0500 ng/mL), n (%) | 15 (5.8) | 15 (5.8) | 15 (5.8) | 15 (5.8) |
| Mean (SD) | 4.4 (3.00) | 2.0 (1.21) | 1.0 (0.56) | 2.6 (1.38) |
| Median | 3.7 | 1.8 | 0.9 | 2.5 |
| Min, Max | 0.0, 21.6 | 0.0, 6.7 | 0.0, 3.7 | 0.0, 13.4 |
| Day 2 Post-Dose | | | | |
| n | 252 | 252 | 252 | 252 |
| BLQ (<0.0500 ng/mL), n (%) | 5 (2.0) | 5 (2.0) | 5 (2.0) | 5 (2.0) |
| Mean (SD) | 11.5 (5.76) | 5.4 (1.90) | 2.6 (1.11) | 5.6 (2.11) |
| Median | 10.4 | 5.6 | 2.5 | 5.5 |
| Min, Max | 0.0, 37.9 | 0.0, 10.5 | 0.0, 6.8 | 0.0, 14.9 |
| Day 29 Pre-Dose | | | | |
| n | 247 | 247 | 247 | 247 |
| BLQ (<0.0500 ng/mL), n (%) | 6 (2.4) | 8 (3.2) | 8 (3.2) | 6 (2.4) |
| Mean (SD) | 15.1 (9.23) | 4.7 (2.60) | 2.8 (1.52) | 9.3 (5.08) |
| Median | 13.7 | 4.2 | 2.6 | 8.9 |
| Min, Max | 0.0, 64.8 | 0.0, 15.9 | 0.0, 8.1 | 0.0, 30.2 |
| Day 29 Post-Dose | | | | |
| n | 253 | 253 | 253 | 253 |
| BLQ (<0.0500 ng/mL), n (%) | 6 (2.4) | 8 (3.2) | 8 (3.2) | 6 (2.4) |
| Mean (SD) | 21.1 (10.81) | 7.8 (3.09) | 4.3 (1.88) | 12.3 (5.62) |
| Median | 19.6 | 7.6 | 4.1 | 11.8 |
| Min, Max | 0.0, 73.2 | 0.0, 20.0 | 0.0, 10.3 | 0.0, 34.4 |

Lower limit of quantification for Lemborexant and its metabolites: 0.0500 ng/mL.
BLQ = below limit of quantification.

TABLE 27

Overview of Auditory Awakening Threshold Treatment Differences.

| | n[a] | Mean (SD) | Median | LSM (SE) | LSM - Difference vs. Placebo | P-value vs. Placebo | P-value vs. Zolpidem ER |
|---|---|---|---|---|---|---|---|
| Placebo | 42 | 50.0 (26.0) | 45.0 | 49.9 (4.2) | — | — | — |
| Zolpidem 6.25 mg | 50 | 58.4 (28.9) | 55.0 | 57.1 (3.9) | 7.2 | NS | — |

TABLE 27-continued

Overview of Auditory Awakening Threshold Treatment Differences.

| | n[a] | Mean (SD) | Median | LSM (SE) | LSM - Difference vs. Placebo | P-value vs. Placebo | P-value vs. Zolpidem ER |
|---|---|---|---|---|---|---|---|
| Lemborexant 5 mg | 47 | 51.8 (23.7) | 50.0 | 51.6 (3.3) | 1.7 | NS | NS |
| Lemborexant 10 mg | 50 | 51.7 (24.4) | 52.5 | 49.0 (3.7) | −0.9 | NS | NS |

LSM = least squares mean
NS = not significant
SD = standard deviation
SE = standard error
[a]= varying number of subjects due either to subject already awake or technical issues.

As shown in Table 27, administration of lemborexant did not interfere with a subject's ability to be awakened by an external stimulus.

TABLE 28

Overview of Return to Sleep Latency.

| | n | Baseline | Postdose | Mean (SD) change from baseline | LSM - Difference vs. Placebo | P-value vs. Placebo | P-value vs. Zolpidem ER |
|---|---|---|---|---|---|---|---|
| Placebo | 51 | 40.9 (28.9) | 40.9 (34.8) | 0.0 (25.9) | — | — | — |
| Zolpidem 6.25 mg | 51 | | 19.6 (19.0) | −21.2 (24.7) | −21.0 | **** | — |
| Lemborexant 5 mg | 51 | | 18.1 (22.8) | −22.8 (26.5) | −22.5 | **** | NS |
| Lemborexant 10 mg | 51 | | 12.1 (17.2) | −28.7 (30.9) | −28.7 | **** | — |

Return to seep latency measured in minutes.
LSM = least squares mean
NS = not significant
SD = standard deviation As shown in Table 28, treatment with lemborexant (both doses) resulted in a greater reduction in return to sleep latency than treatment with placebo and zolpidem.

TABLE 29

Overview of Treatment-Emergent Adverse Events (Safety Analysis Set).

| Category | Placebo (N = 209) n (%) | Zolpidem ER 6.25 mg (N = 263) n (%) | Lemborexant 5 mg (N = 266) n (%) | Lemborexant 10 mg (N = 268) n (%) |
|---|---|---|---|---|
| TEAEs | 53 (25.4) | 93 (35.4) | 74 (27.8) | 82 (30.6) |
| Treatment-related TEAEs | 16 (7.7) | 40 (15.2) | 30 (11.3) | 39 (14.6) |
| Severe TEAEs | 3 (1.4) | 8 (3.0) | 1 (0.4) | 2 (0.7) |
| Serious TEAEs | 0 | 4 (1.5) | 2 (0.8) | 0 |
| Deaths | 0 | 0 | 0 | 0 |
| Other SAEs | 0 | 4 (1.5) | 2 (0.8) | 0 |
| Life threatening | 0 | 0 | 0 | 0 |
| Requires inpatient hospitalization or prolongation of existing hospitalization | 0 | 4 (1.5) | 2 (0.8) | 0 |
| Persistent or significant disability or incapacity | 0 | 0 | 0 | 0 |

TABLE 29-continued

| Overview of Treatment-Emergent Adverse Events (Safety Analysis Set). | | | | |
|---|---|---|---|---|
| Category | Placebo (N = 209) n (%) | Zolpidem ER 6.25 mg (N = 263) n (%) | Lemborexant 5 mg (N = 266) n (%) | Lemborexant 10 mg (N = 268) n (%) |
| Congenital anomaly/birth defect | 0 | 0 | 0 | 0 |
| Important medical events | 0 | | 1 (0.3) | 0 |
| TEAEs leading to study drug dose adjustment | 2 (1.0) | 8 (3.0) | 3 (1.1) | 3 (1.1) |
| TEAEs leading to study drug withdrawal | 2 (1.0) | 7 (2.7) | 2 (0.8) | 3 (1.1) |
| TEAEs leading to study dose reduced | 0 | 0 | 0 | 0 |
| TEAEs leading to study drug interrupted | 1 (0.5) | 2 (0.8) | 1 (0.4) | 0 |

TEAE = treatment-emergent adverse event.
SAE = serious adverse event

Table 29 shows that lemborexant is a safe and well-tolerated drug, as indicated by the low incidence of adverse events. There were no deaths reported during this study.

FIGS. 11A-11D show that, after the first 2 nights of treatment, treatment with zolpidem ER resulted in significantly worse performance than placebo and 5 mg of treatment on 3 of the 4 domains of the Cognitive Performance Assessment Battery, and on 2 of the 4 domains versus 10 mg lemborexant. In contrast, neither dose of lemborexant differed from placebo on cognitive tests at either point.

Figure 12:
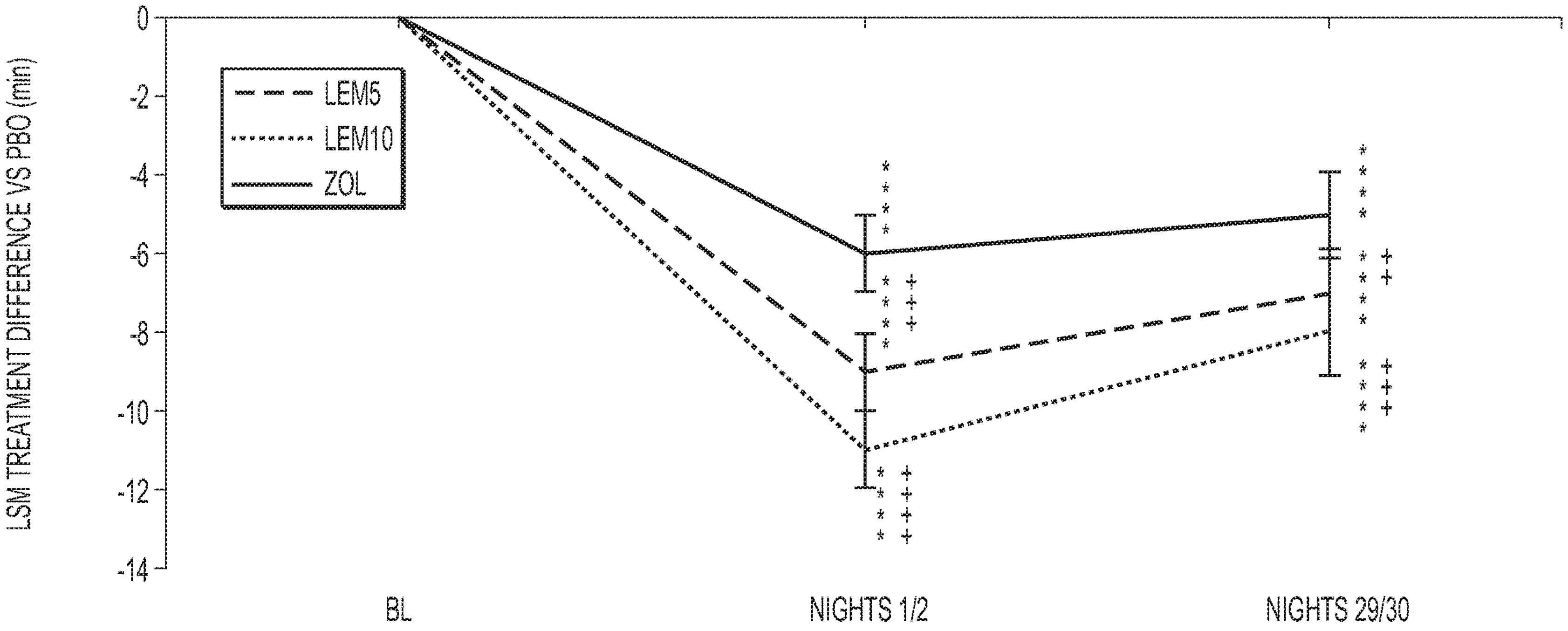
FIG. 12 shows the change from baseline (least squares mean) in minutes of duration of long awakenings (defined as a period of wakefulness lasting 5 or more minutes, while trying to sleep) at Days 2/3 and Days 30/31 in patients treated with placebo, 6.25 mg of zolpidem, 5 mg of lemborexant, or 10 mg of lemborexant.
Figure 13A:
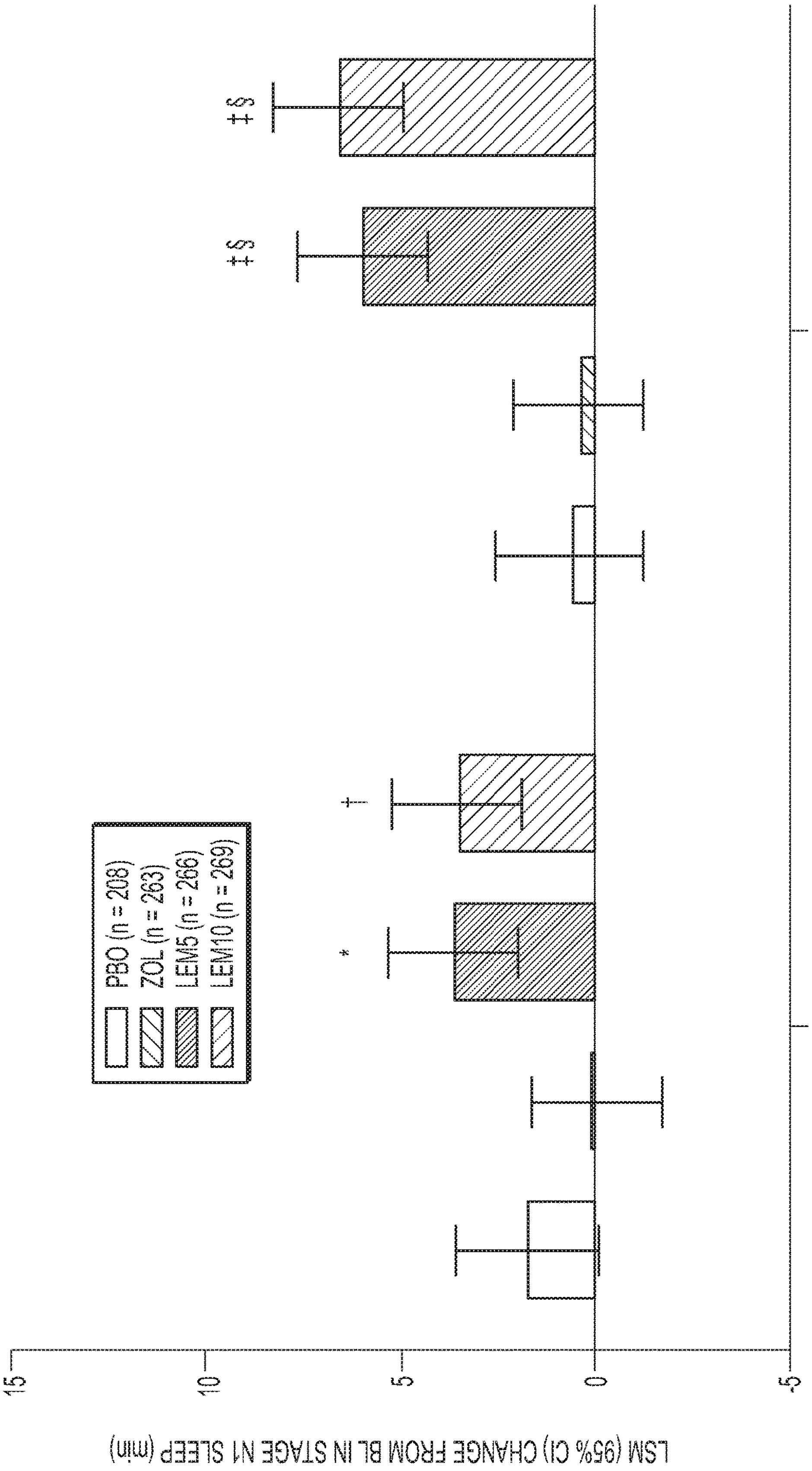
FIG. 13A, FIG. 13B, and FIG. 13C show the change from baseline (least squares mean) in the minutes asleep during Stage N1, Stage N2, and Stage N3 sleep, respectively, at Nights 1/2 and Nights 29/30 in patients treated with placebo, 6.25 mg of zolpidem, 5 mg of lemborexant, or 10 mg of lemborexant.
Figure 13B:
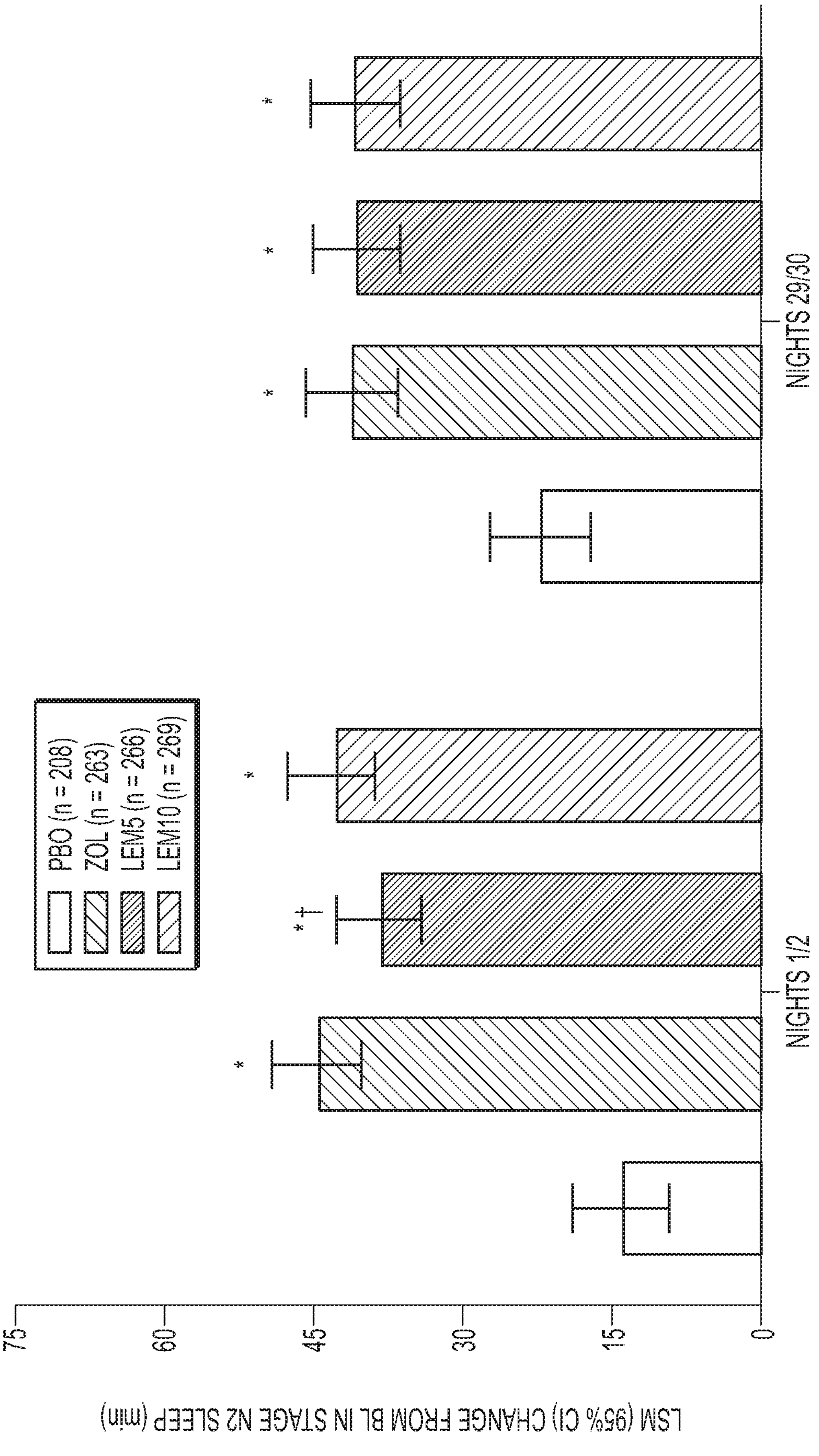
Figure 13C:
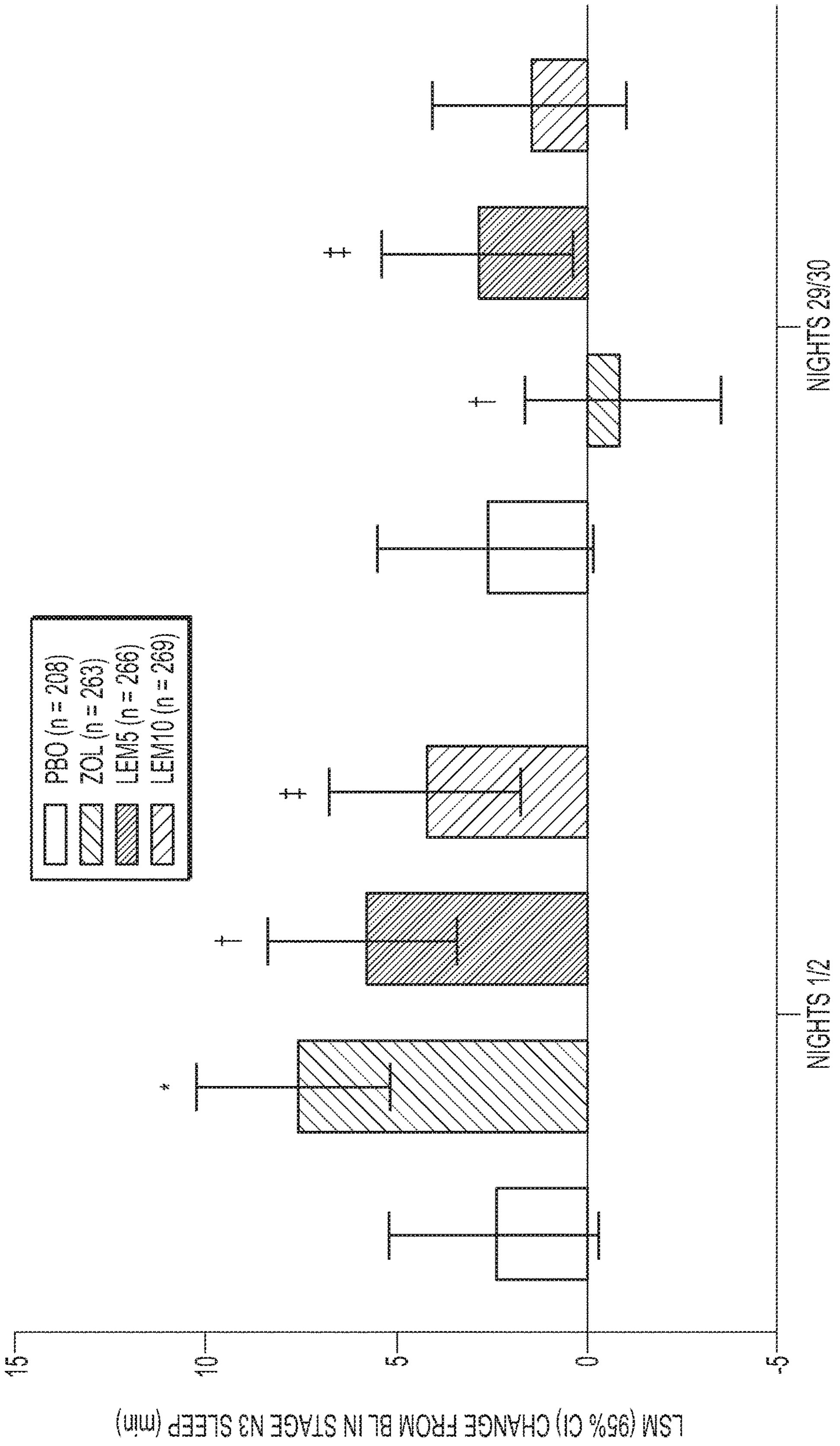
Figure 14:
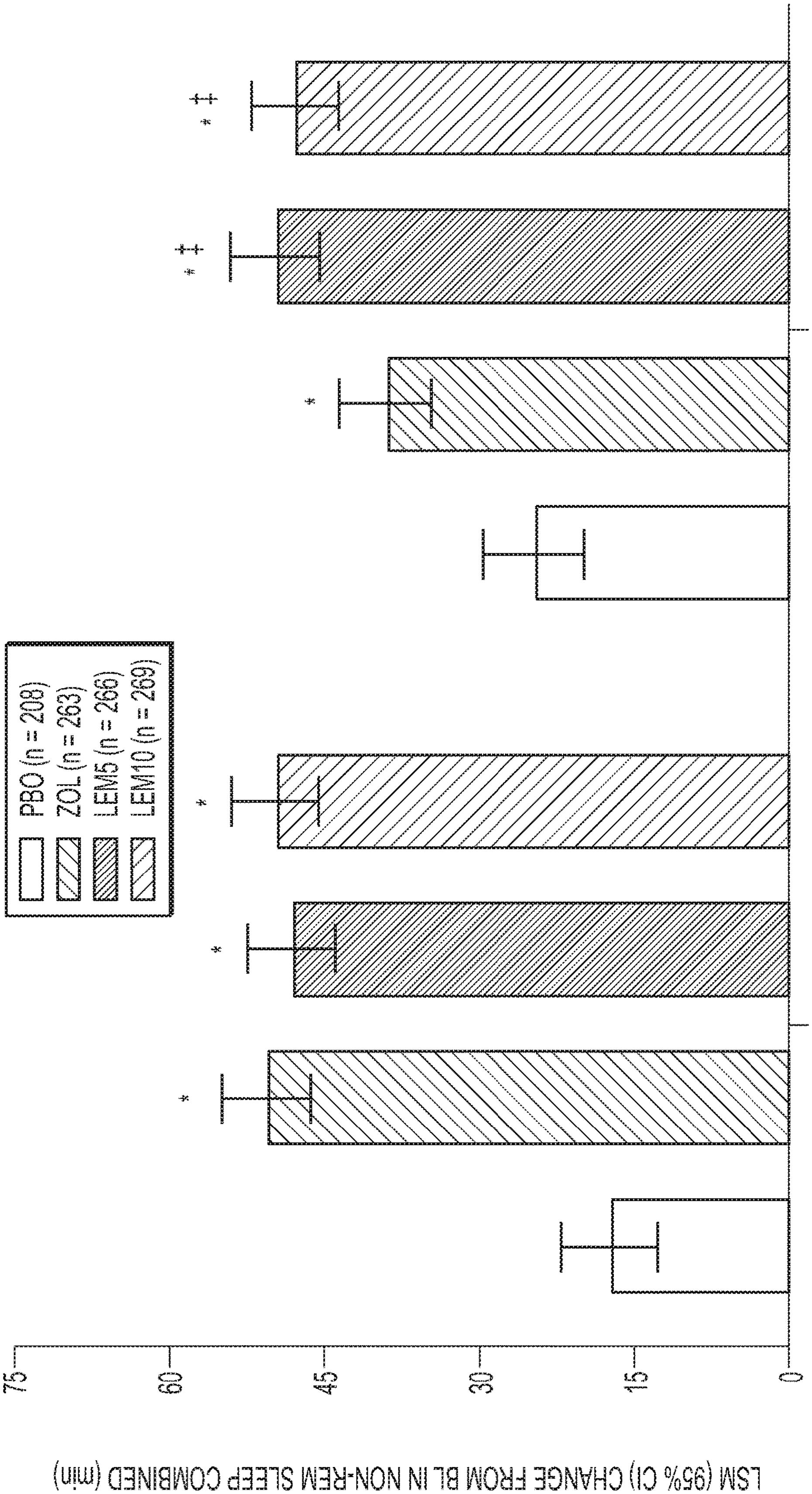
FIG. 14 shows the change from baseline (least squares mean) in the minutes asleep during non-rapid eye movement (REM) sleep at Nights 1/2 and Nights 29/30 in patients treated with placebo, 6.25 mg of zolpidem, 5 mg of lemborexant, or 10 mg of lemborexant.

FIG. 12 shows that treatment with lemborexant (both doses) resulted in a greater reduction in the length of long awakenings than treatment with zolpidem ER, relative to placebo.

Figure 15:
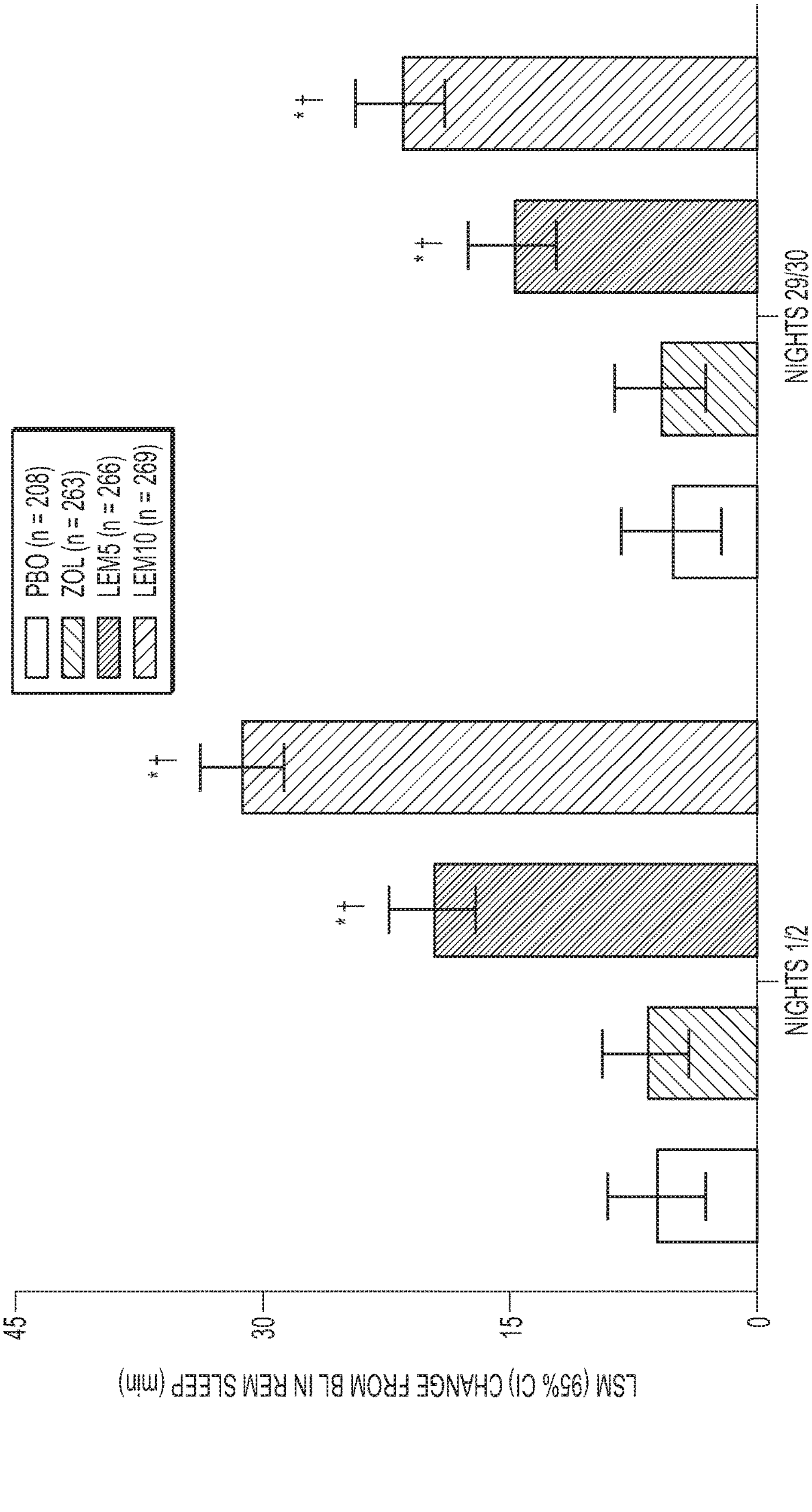
FIG. 15 shows the change from baseline (least squares mean) in the minutes asleep during non-REM sleep at Nights 1/2 and Nights 29/30 in patients treated with placebo, 6.25 mg of zolpidem, 5 mg of lemborexant, or 10 mg of lemborexant.

FIG. 15 shows that treatment with lemborexant (both doses) resulted in a greater increase in non-REM sleep compared to treatment with placebo and zolpidem ER.

Figure 16:
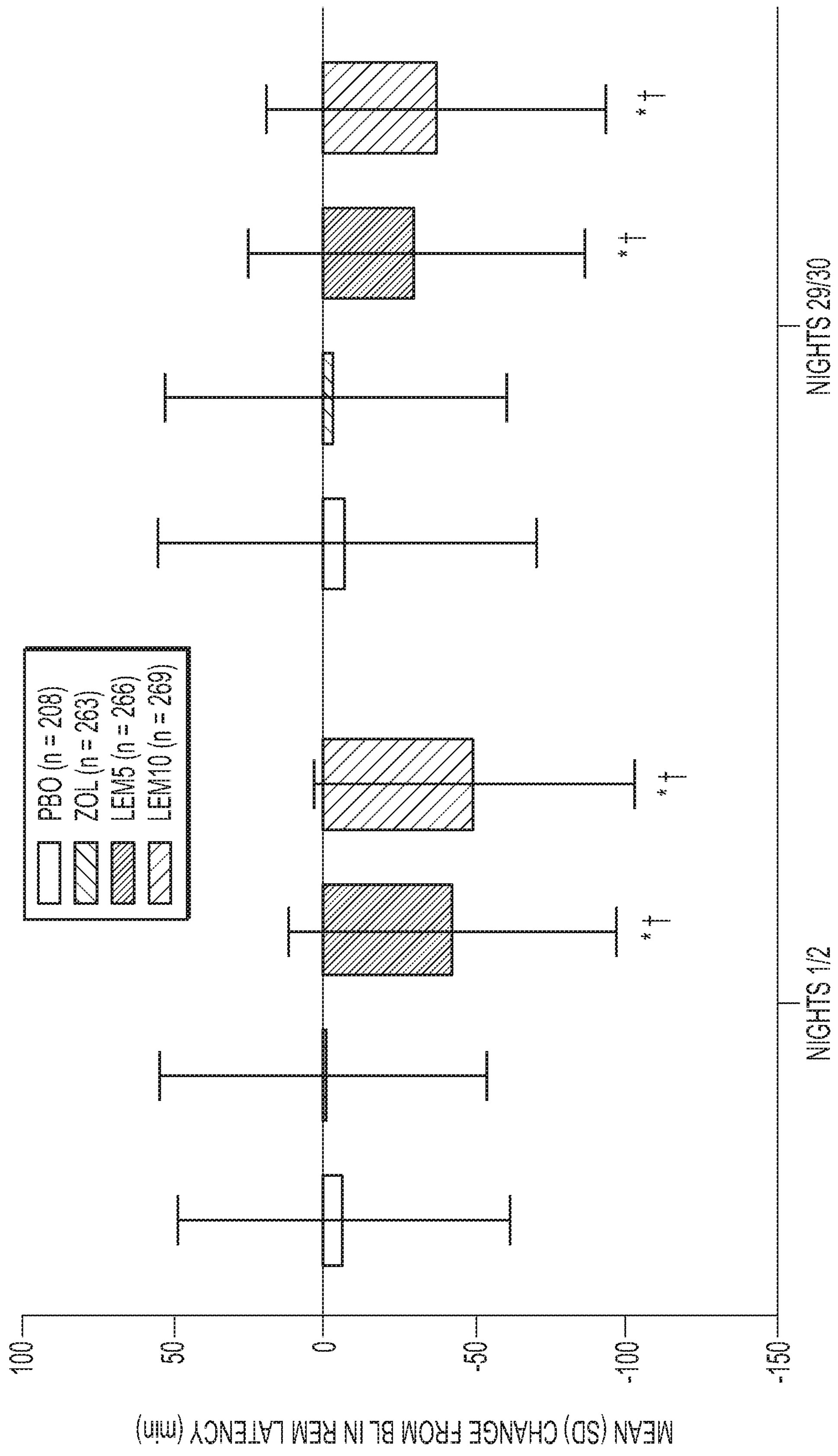
FIG. 16 shows the mean change from baseline in minutes of REM latency at Nights 1/2 and Nights 29/30 in patients treated with placebo, 6.25 mg of zolpidem, 5 mg of lemborexant, or 10 mg of lemborexant.

FIG. 16 shows that treatment with lemborexant (both doses) resulted in a greater mean decrease in REM latency compared to treatment with placebo and zolpidem ER.

Example 3. Responder Analysis of Treatment of Subjects Having Insomnia Disorder The data collected in studies described in Example 1 and Example 2 were pooled and the response of each subject was analyzed.

Subjective Sleep Onset Latency

TABLE 30

| Summary and Analysis of Proportion of Subjective Sleep Onset Latency Responders with Data Handling Rules (Full Analysis Set, Examples 1 and 2) | | | |
|---|---|---|---|
| Statistic | Placebo (N = 527) | Lemborexant 5 mg (N = 582) | Lemborexant 10 mg (N = 584) |
| First 7 Days | | | |
| Responder, n (%) | | | |
| n[a] | 405 | 461 | 443 |
| Yes | 19 (4.7) | 57 (12.4) | 56 (12.6) |
| No | 382 (94.3) | 398 (86.3) | 382 (86.2) |
| Missing[b] | 4 (1.0) | 6 (1.3) | 5 (1.1) |
| 95% CI for proportion of responders | (2.6, 6.8) | (9.4, 15.4) | (9.5, 15.7) |
| Difference of proportion vs. Placebo (95% CI) P-value by CMH test | | 7.80 (4.14, 11.46) <0.0001 | 7.80 (4.11, 11.50) <0.0001 |
| Month 1 | | | |
| Responder, n (%) | | | |
| n[a] | 405 | 461 | 443 |
| Yes | 41 (10.1) | 85 (18.4) | 93 (21.0) |
| No | 341 (84.2) | 354 (76.8) | 336 (75.8) |
| Missing[b] | 23 (5.7) | 22 (4.8) | 14 (3.2) |
| 95% CI for proportion of responders | (7.2, 13.1) | (14.9, 22.0) | (17.2, 24.8) |
| Difference of proportion vs. Placebo (95% CI) P-value by CMH test | | 8.28 (3.66, 12.89) 0.0006 | 11.14 (6.33, 15.96) <0.0001 |

CI = confidence interval
CMH = Cochran-Mantel-Haenszel
[a]= number of subjects with sSOL >30 minutes at baseline
P-value is based on Cochran-Mantel-Haenszel test stratified by study, region, and age group.
[b]= subjects with missing information due to early withdrawal or other reasons are considered as non-responders in this analysis.

At the beginning of treatment (first 7 days) and at the end of month 1, the proportion of responders (defined as those subjects with sSOL of 20 or less minutes provided their baseline sSOL was at least 30 minutes) was statistically significantly superior for both lemborexant doses compared with treatment with placebo, as shown in Table 30.

Subjective Wake After Sleep Onset

TABLE 31

Summary and Analysis of Proportion of Subjective Wake After Sleep Onset Responders with Data Handling Rules (Full Analysis Set, Examples 1 and 2)

| Statistic | Placebo (N = 527) | Lemborexant 5 mg (N = 582) | Lemborexant 10 mg (N = 584) |
|---|---|---|---|
| First 7 Days | | | |
| Responder, n (%) | | | |
| n[a] | 447 | 518 | 517 |
| Yes | 51 (11.4) | 91 (17.6) | 100 (19.3) |
| No | 390 (87.2) | 420 (81.1) | 411 (79.5) |
| Missing[b] | 6 (1.3) | 7 (1.4) | 6 (1.2) |
| 95% CI for proportion of responders | (8.5, 14.4) | (14.3, 20.8) | (15.9, 22.7) |
| Difference of proportion vs. Placebo (95% CI) P-value by CMH test | | 6.15 (1.73, 10.57) 0.0072 | 7.84 (3.33, 12.35) 0.0009 |
| Month 1 | | | |
| Responder, n (%) | | | |
| n[a] | 447 | 518 | 517 |
| Yes | 79 (17.7) | 121 (23.4) | 122 (23.6) |
| No | 345 (77.2) | 372 (71.8) | 368 (71.2) |
| Missing[b] | 23 (5.1) | 25 (4.8) | 27 (5.2) |
| 95% CI for proportion of responders | (14.1, 21.2) | (19.7, 27.0) | (19.9, 27.3) |
| Difference of proportion vs. Placebo (95% CI) P-value by CMH test | | 5.61 (0.51, 10.71) 0.0325 | 5.96 (0.85, 11.07) 0.0238 |

CI = confidence interval
CMH = Cochran-Mantel-Haenszel
[a]= number of subjects with sSOL >30 minutes at baseline
[b]= subjects with missing information due to early withdrawal or other reasons are considered as non-responders in this analysis.
P-value is based on Cochran-Mantel-Haenszel test stratified by study, region, and age group.

At the beginning of treatment (first 7 days) and at the end of month 1, the proportion of responders (defined as those with sWASO of 60 or less minutes and a reduction from baseline of at least 10 minutes provided baseline sWASO was greater than 60 minutes) was statistically significantly superior for treatment with both lemborexant doses compared to treatment with placebo, as shown in Table 31.

Insomnia Severity Index

TABLE 32

Summary and Analysis of Proportion of Subjects Whose Total Insomnia Severity Index Score Decreased from Baseline to Month 1 by ≥7 Points (Full Analysis Set, Examples 1 and 2)

| Statistic | Placebo (N = 527) | Lemborexant 5 mg (N = 582) | Lemborexant 10 mg (N = 584) |
|---|---|---|---|
| Responder, n (%) | | | |
| n[a] | 527 | 582 | 584 |
| Yes | 177 (33.6) | 275 (47.3) | 279 (47.8) |
| No | 317 (60.2) | 283 (48.6) | 261 (44.7) |
| Missing[b] | 33 (6.3) | 24 (4.1) | 44 (7.5) |
| 95% CI for proportion of responders | (29.6, 37.6) | (43.2, 51.3) | (43.7, 51.8) |
| Difference of proportion vs. Placebo (95% CI) P-value by CMH test | | 13.12 (7.39, 18.84) <0.0001 | 13.61 (7.92, 19.30) <0.0001 |

CI = confidence interval
CMH = Cochran-Mantel-Haenszel
[a]= number of subjects with sSOL >30 minutes at baseline
[b]= subjects with missing information due to early withdrawal or other reasons are considered as non-responders in this analysis.
P-value is based on Cochran-Mantel-Haenszel test stratified by study, region, and age group.

TABLE 33

Summary and Analysis of Proportion of Subjects Whose Insomnia Severity Index Total Score Decreased from Baseline to Month 1 and Was <10 (Full Analysis Set, Examples 1 and 2)

| Statistic | Placebo (N = 527) | Lemborexant 5 mg (N = 582) | Lemborexant 10 mg (N = 584) |
|---|---|---|---|
| Responder, n (%) | | | |
| n[a] | 527 | 582 | 584 |
| Yes | 107 (20.3) | 192 (33.0) | 195 (33.4) |
| No | 387 (73.4) | 366 (62.9) | 345 (59.1) |
| Missing[b] | 33 (6.3) | 24 (4.1) | 44 (7.5) |
| 95% CI for proportion of responders | (16.9, 23.7) | (29.2, 36.8) | (29.6, 37.2) |
| Difference of proportion vs. Placebo (95% CI) P-value by CMH test | | 12.44 (7.29, 17.59) <0.0001 | 12.71 (7.58, 17.84) <0.0001 |

CI = confidence interval
CMH = Cochran-Mantel-Haenszel
[a]= number of subjects with sSOL >30 minutes at baseline
[b]= subjects with missing information due to early withdrawal or other reasons are considered as non-responders in this analysis.
P-value is based on Cochran-Mantel-Haenszel test stratified by study, region, and age group.

Table 32 provides the summary and analysis of responders, defined as those subjects whose Total ISI Score decreased at the end of month 1 by 7 or more points compared to baseline. Table 33 provides the summary and analysis of responders, defined as those subjects whose ISI Total Score decreased compared to baseline and was less than 10 at month 1. For both doses of lemborexant, the difference of proportion of responders in the lemborexant group versus the placebo group was statistically significant.

At the end of month 1, the percentage of subjects whose ISI Total Score decreased by 7 or more points was 33.6% in the placebo group versus 47.3% in the 5 mg lemborexant treatment group and 47.8% in the 10 mg lemborexant treatment group, as shown in Table 32.

At the end of month 1, the percentage of subjects whose ISI Total Score decreased at month 1 and was less than 10 was 20.3% of the placebo treatment group versus 33.0% in the 5 mg lemborexant treatment group and 33.4% in the 10 mg lemborexant treatment group, as shown in Table 33.

What is claimed:

1. A method for treating insomnia in a patient, comprising administering orally a dosage form comprising lemborexant or a pharmaceutically acceptable salt thereof at a single daily dose ranging from about 5 to 10 mg of lemborexant or an equivalent dose of a pharmaceutically acceptable salt thereof for at least six months, wherein the Subjective Sleep Onset Latency (sSOL) is reduced by at least 20 minutes relative to baseline.

2. The method according to claim 1, wherein the method comprises comprising administering orally the dosage form comprising 5 mg of lemborexant to the patient no more than once per night, immediately before going to bed, with at least 7 hours remaining before the planned time of awakening.

3. The method according to claim 1, wherein the method comprises first administering orally the dosage form comprising 5 mg of lemborexant to the patient no more than once per night, immediately before going to bed, with at least 7 hours remaining before the planned time of awakening, monitoring the response of the patient to lemborexant, and increasing wherein the dose of lemborexant may be increased to 10 mg once daily if the 5 mg dose does not reduce the subjective Sleep Onset Latency (sSOL) by at least 15 minutes relative to baseline for at least one month.

4. The method according to claim 1, wherein the method comprises administering orally the dosage form comprising 10 mg of lemborexant to the patient no more than once per night, immediately before going to bed, with at least 7 hours remaining before the planned time of awakening.

5. The method according to claim 1, wherein the single dose is 5 mg or 10 mg of lemborexant.

6. The method according to claim 1, wherein the sSOL is reduced by at least 22 minutes relative to baseline.

7. A method for treating insomnia in a patient, comprising administering orally a dosage form comprising lemborexant or a pharmaceutically acceptable salt thereof at a single daily dose ranging from about 5 to 10 mg of lemborexant or an equivalent dose of a pharmaceutically acceptable salt thereof, wherein the subjective Wake After Sleep Onset (sWASO) is reduced by at least 29 minutes relative to baseline.

8. The method according to claim 7, wherein the dosage form is administered no more than once per night, immediately before going to bed, with at least 7 hours remaining before the planned time of awakening.

9. The method according to claim 8, wherein the single dose is 5 mg or 10 mg of lemborexant.

10. The method according to claim 7, wherein the sWASO is reduced by at least 40 minutes relative to baseline.

11. The method according to claim 7, wherein the method comprises first comprising administering orally the dosage form comprising 5 mg of lemborexant to the patient no more than once per night, immediately before going to bed, with at least 7 hours remaining before the planned time of awakening, monitoring the response of the patient to lemborexant, and increasing the dose of lemborexant to 10 mg once daily if the 5 mg dose does not reduce the subjective Wake After Sleep Onset (sWASO) by at least 29 minutes relative to baseline for at least one month.

12. The method according to claim 7, wherein the method comprises comprising administering orally the dosage form comprising 5 mg of lemborexant to the patient no more than once per night, immediately before going to bed, with at least 7 hours remaining before the planned time of awakening.

13. A method for treating insomnia in a patient, comprising administering orally a dosage form comprising lemborexant or a pharmaceutically acceptable salt thereof at a single daily dose ranging from about 5 to 10 mg of lemborexant or an equivalent dose of a pharmaceutically acceptable salt thereof, for at least six months, wherein the Subjective Sleep Efficiency (sSE) is improved by at least 11% relative to baseline.

14. The method according to claim 13, wherein the dosage form is administered no more than once per night, immediately before going to bed, with at least 7 hours remaining before the planned time of awakening.

15. The method according to claim 13, wherein the single dose is 5 mg or 10 mg of lemborexant.

16. The method according to claim 13, wherein the sSE is improved by at least 12% relative to baseline.

17. The method according to claim 13, wherein the method comprises first administering orally the dosage form comprising 5 mg of lemborexant to the patient no more than once per night , immediately before going to bed, with at least 7 hours remaining before the planned time of awakening, monitoring the response of the patient to lemborexant, and increasing the dose of lemborexant to 10 mg once daily if the 5 mg dose does not improve the subjective Sleep Efficiency (sSE) at least 4% relative to baseline for at least one month.

18. The method according to claim 13, wherein the method comprises administering orally the dosage form comprising 5 mg of lemborexant to the patient no more than once per night, immediately before going to bed, with at least 7 hours remaining before the planned time of awakening.

19. The method according to claim 1, wherein the dosage form is administered to the patient no more than once per night, immediately before going to bed, with at least 7 hours remaining before the planned time of awakening.

20. The method according to claim 7, wherein the method comprises administering orally the dosage form comprising 10 mg of lemborexant to the patient no more than once per night, immediately before going to bed, with at least 7 hours remaining before the planned time of awakening.

21. The method according to claim 13, wherein the method comprises administering orally the dosage form comprising 10 mg of lemborexant to the patient no more than once per night, immediately before going to bed, with at least 7 hours remaining before the planned time of awakening.

* * * * *